United States Patent
Hudson et al.

(10) Patent No.: US 10,183,039 B2
(45) Date of Patent: Jan. 22, 2019

(54) METHODS FOR THE PRODUCTION OF COLLAGEN IV

(71) Applicant: Vanderbilt University, Nashville, TN (US)

(72) Inventors: Billy G. Hudson, Brentwood, TN (US); Christopher F. Cummings, Brentwood, TN (US); Gautam Bhave, Nashville, TN (US); A. Scott McCall, Nashville, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 0 days.

(21) Appl. No.: 14/905,457

(22) PCT Filed: Jul. 14, 2014

(86) PCT No.: PCT/US2014/046507
§ 371 (c)(1),
(2) Date: Jan. 15, 2016

(87) PCT Pub. No.: WO2015/009615
PCT Pub. Date: Jan. 22, 2015

(65) Prior Publication Data
US 2016/0175347 A1 Jun. 23, 2016

Related U.S. Application Data

(60) Provisional application No. 61/846,140, filed on Jul. 15, 2013.

(51) Int. Cl.
| | |
|---|---|
| *A61K 33/00* | (2006.01) |
| *A61K 45/06* | (2006.01) |
| *A61K 31/708* | (2006.01) |
| *A61K 31/7084* | (2006.01) |
| *A61K 33/40* | (2006.01) |
| *G01N 33/49* | (2006.01) |

(52) U.S. Cl.
CPC ............ *A61K 33/00* (2013.01); *A61K 31/708* (2013.01); *A61K 31/7084* (2013.01); *A61K 33/40* (2013.01); *A61K 45/06* (2013.01); *G01N 33/49* (2013.01)

(58) Field of Classification Search
CPC .............................. A61K 33/00; A61K 31/708
See application file for complete search history.

(56) References Cited

U.S. PATENT DOCUMENTS

| | | | |
|---|---|---|---|
| 3,558,778 A | 1/1971 | Klingbail | |
| 6,125,297 A | 9/2000 | Siconolfi | |
| 6,365,616 B1 | 4/2002 | Kohn et al. | |
| 6,410,599 B1 | 6/2002 | Johnson | |
| 6,537,823 B1 | 3/2003 | Smith | |
| 7,393,522 B2 * | 7/2008 | Najafi | A01N 59/00 |
| | | | 424/613 |
| 8,017,623 B2 * | 9/2011 | Singh | A61K 31/439 |
| | | | 514/286 |
| 9,289,417 B2 | 3/2016 | Hudson et al. | |
| 2002/0188015 A1 | 12/2002 | Ulrich et al. | |
| 2004/0043075 A1 | 3/2004 | Ritter et al. | |
| 2005/0118216 A1 * | 6/2005 | Senee | A61K 8/0208 |
| | | | 424/401 |
| 2008/0292709 A1 | 11/2008 | Nyce | |
| 2009/0285890 A1 | 11/2009 | Van Den Plas et al. | |
| 2010/0304412 A1 | 12/2010 | Cuckle et al. | |

FOREIGN PATENT DOCUMENTS

| | | | | |
|---|---|---|---|---|
| EP | 1516639 | | 7/2007 | |
| EP | 2347753 B1 * | | 12/2016 | ............. A61K 8/416 |
| WO | WO 2010/144822 | | 12/2010 | |
| WO | WO 2012/134965 | | 10/2012 | |

OTHER PUBLICATIONS

"*Homo sapiens* peroxidasin homolog (*Drosophila*) (PXDN), mRNA," NCBI Reference Sequence: NM_012293.1, 1994.
"Peroxidasin homolog precursor [*Homo sapiens*]" NCBI Reference Sequence: NP_036425.1, 1999.
Aceves et al., "Is iodine a gatekeeper of the integrity of the mammary gland?", *J Mammary Gland Biol Neoplasia.* 10(2): 189-96, 2005.
Beal et al., "Hypochlorous acid reacts with the N-terminal methionines of proteins to give dehydromethionine, a potential biomarker for neutrophil-induced oxidative stress", *Biochemistry* 48, 11142-11148, 2009.
Bhave et al., "Peroxodasin forms sulfilimine chemical bonds usind hypohalous acids in tissue genesis", *Nature Chemical Biology* 8: 784-790, 2012.
Bignon, et al., "Lysyl oxidase-like protein-2 regulates sprouting angiogenesis and type IV collagen assembly in the endothelial basement membrane", *Blood*, 118(14): 3979-89, 2011.
Borchiellini et al., "The function of type IV collagen during *Drosophila* muscle development", *Mech Dev.* 58(1-2): 179-91, 1996.
Borza et al., "Goodpasture autoantibodies unmask cryptic epitopes by selectively dissociating autoantigen complexes lacking structural reinforcement: novel mechanisms for immune privilege and autoimmune pathogenesis," *J. Biol. Chem.*, 280(29):27147-27154, 2005.
Burnier, et. al., "Type IV collagen-initiated signals provide survival and growth cues required for liver metastasis", *Oncogene*, 30(35): 3766-83, 2011.
Cooper et al., "Pathogenesis, prevention, and treatment of diabetic nephropathy", *Lancet*, 352: 213-219, 1998.
Donkó et al., "Detection of hydrogen peroxide by lactoperoxidase-mediated dityrosine formation", *Free Radic Res.*, 43(5): 440-5, 2009.

(Continued)

*Primary Examiner* — Gina C Justice
(74) *Attorney, Agent, or Firm* — Parker Highlander PLLC

(57) ABSTRACT

The method of the current disclosure provides for methods of increasing sulfilimine bonds in collagen IV using bromide containing agents and conditions that either promote peroxidasin cross-linking of collagen IV.

16 Claims, 36 Drawing Sheets

(56) References Cited

OTHER PUBLICATIONS

Elgawish et al., "Involvement of hydrogen peroxide in collagen cross-linking by high glucose in vitro and in vivo," *J. Biol. Chem.*, 271(22): 12964-12971, 1996.
Fan et al., "Novel investigations of sulfimide systems", Loughborough University's Institutional Repository, Chapter 2, 2011.
Fidler et al., "A unique covalent bond in basement membrane is a primordial innovation for tissue evolution", *Proc. Natl. Acad. Sci. USA* 111, 331-336, 2014.
Gotenstein et. al., "The *C. elegans* peroxidasin PXN-2 is essential for embryonic morphogenesis and inhibits adult axon regeneration", *Development* 137(21):3603-13, 2010.
Gupta et al., "Characterization of $\alpha 1$(IV) collagen mutations in *Caenorhabditis elegans* and the effects of $\alpha 1$ and $\alpha 2$(IV) mutations on type IV collagen distribution", *J Cell Biol.*, 137(5): 1185-96, 1997.
Hallum et al., "Congenital paralytic ileus in a premature baby as a complication of hexamethonium bromide therapy for toxaemia of pregnancy", *Archives of Disease in Childhood*, 31(160): 354-356, 1954.
Hermanns, et. al., "The collagenous wound healing scar in the injured central nervous system inhibits axonal regeneration", *Adv Exp Med Biol.* 557: 177-90, 2006.
Hudson et al., "Alport's syndrome, Goodpasture's syndrome, and type IV collagen," *N. Engl. J. Med.*, 348:2543, 2003.
International Preliminary Report on Patentability issued in PCT/US2010/038341, dated Dec. 22, 2011.
International Search Report and Written Opinion issued in International Application No. PCT/US2014/046507, dated Oct. 10, 2014.
International Preliminary Report on Patentability issued in PCT/US2014/046507, dated Jan. 28, 2016.
International Search Report and Written Opinion issued in PCT/US2010/038341, dated Nov. 8, 2010.
Kruegel and Miosge, "Basement membrane components are key players in specialized extracellular matrices", *Cell Mol Life Sci.* 67(17): 2879-95, 2010.
Larios et al., "Oxidative protein cross-linking reactions involving L-tyrosine in transforming growth factor-$\beta 1$-stimulated fibroblasts," *J. Biol. Chem.*, 276(20): 17437-17441, 2001.
Liu, et. al., "Genomic instability in laminopathy-based premature aging", *Nat Med*, 11(7): 780-5, 2005.
Marcinkiewicz, "Taurine bromamine (TauBr)—its role in immunity and new perspectives for clinical use", *J Biomedical Science.* 17(Suppl 1): S3, 2010.
Mayeno et al., "Eosinophils preferentially use bromide to generate halogenating agents", *J. of Biological Chemistry*, 264(10): 5660-5668, 1989.
Peskin et al., "Oxidation of methionine to dehydromethionine by reactive halogen species generated by neutrophils", *Biochemistry* 48: 10175-10182, 2009.
Péterfi et. al., "Peroxidasin is secreted and incorporated into the extracellular matrix of myofibroblasts and fibrotic kidney", *Am J Pathol.* 175(2): 725-35, 2009.
Pöschl et. al., "Collagen IV is essential for basement membrane stability but dispensable for initiation of its assembly during early development", *Development*, 131(7): 1619-28, 2004.
Siebold et al., "The arrangement of intra- and intermolecular disulfide bonds in the carboxyterminal, non-collagenous aggregation and cross-linking domain of basement-membrane type IV collagen," *Eur. J. Biochem.*, 176(3):617-624, 1988.
Sundaramoorthy et al., "Crystal structure of NC1 domains. Structural basis for type IV collagen assembly in basement membranes," *J. Biol. Chem.*, 277:31142, 2002.
Than et al., "The 1.9-A crystal structure of the noncollagenous (NC1) domain of human placenta collagen IV shows stabilization via a novel type of covalent Met-Lys cross-link," *Proc Natl Acad Sci USA*, 99(10):6607-6612, 2002.
Than et al., "The NC1 dimer of human placental basement membrane collagen IV: does a covalent crosslink exist?" *Biological Chemistry*, 386:759, 2005.
Vanacore et al., "A role for collagen IV cross-links in conferring immune privilege to the Goodpasture autoantigen: structural basis for the crypticity of B cell epitopes," *J Biol Chem.*, 283(33):22737-22748, 2008.
Vanacore et al., "A sulfilimine bond identified in collagen IV", *Science* 325, 1230-1234, 2009.
Vanacore et al., "Identification of S-hydroxylysyl-methionine as the covalent cross-link of the noncollagenous (NC1) hexamer of the alpha1alpha1alpha2 collagen IV network: a role for the post-translational modification of lysine 211 to hydroxylysine 211 in hexamer assembly," *J Biol Chem.*, 280(32): 29300-29310, 2005.
Vanacore et al., "The $\alpha 1.\alpha 2$ network of collagen IV. Reinforced stabilization of the noncollagenous domain-1 by noncovalent forces and the absence of Met-Lys cross-links," *J. Biol Chem.*, 279(43): 44723-44730, 2004.
Weiss, "Tying the collagen-sulfilimine knot", *Nature Chemical Biology*, 8: 740-741, 2012.

\* cited by examiner

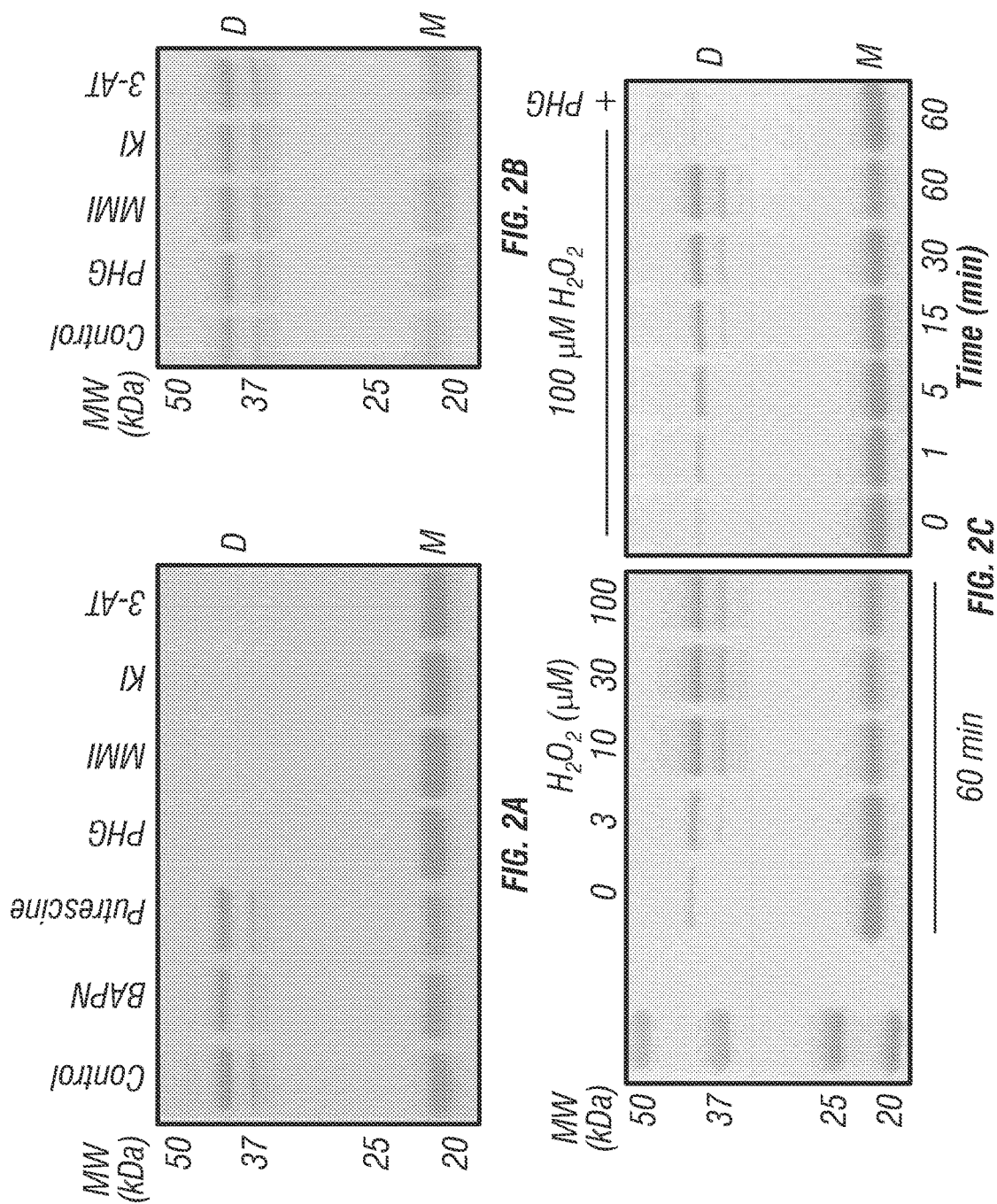

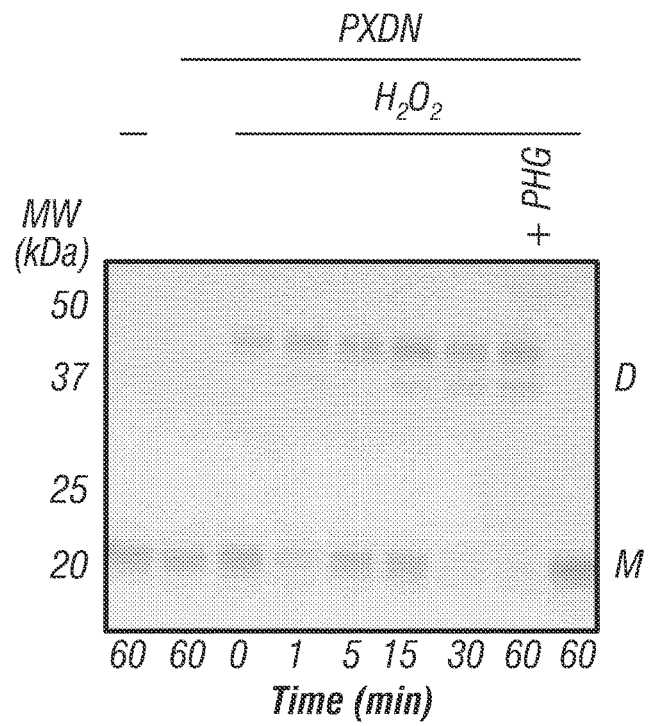
FIG. 3A
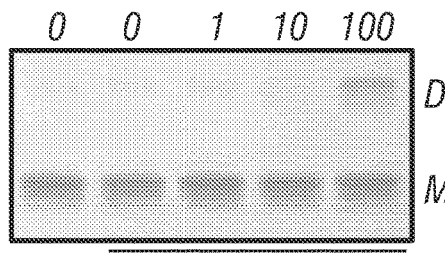
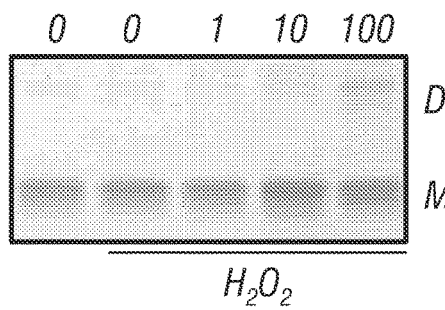
FIG. 3B
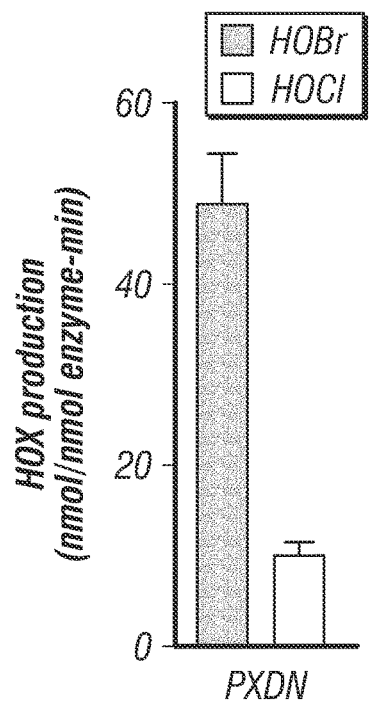
FIG. 3C

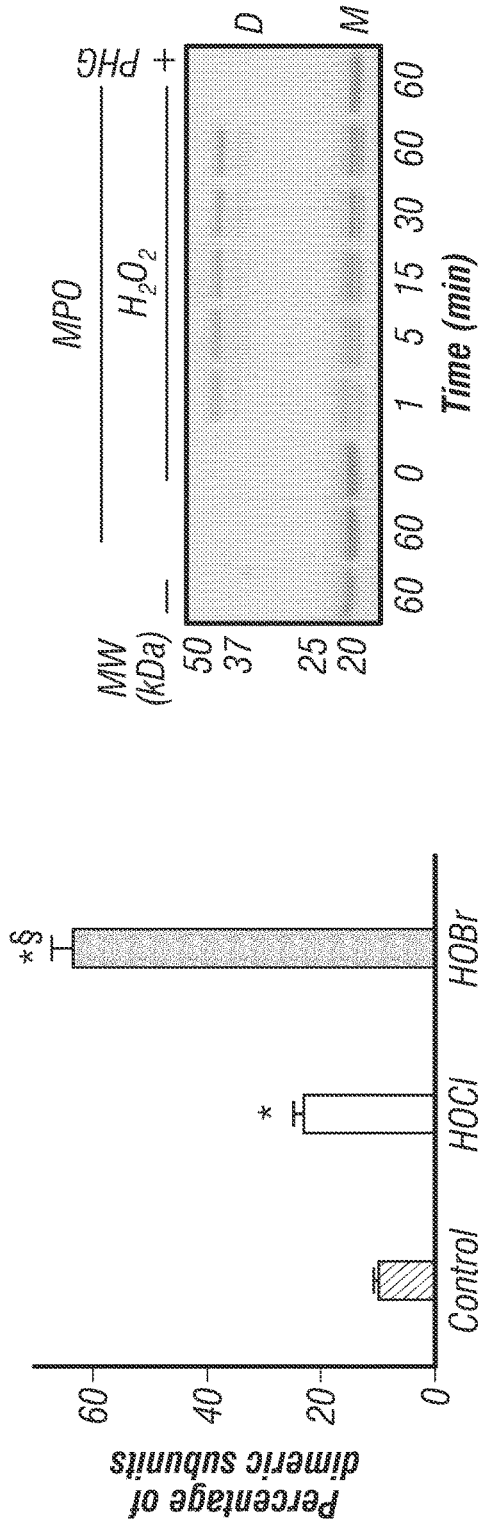
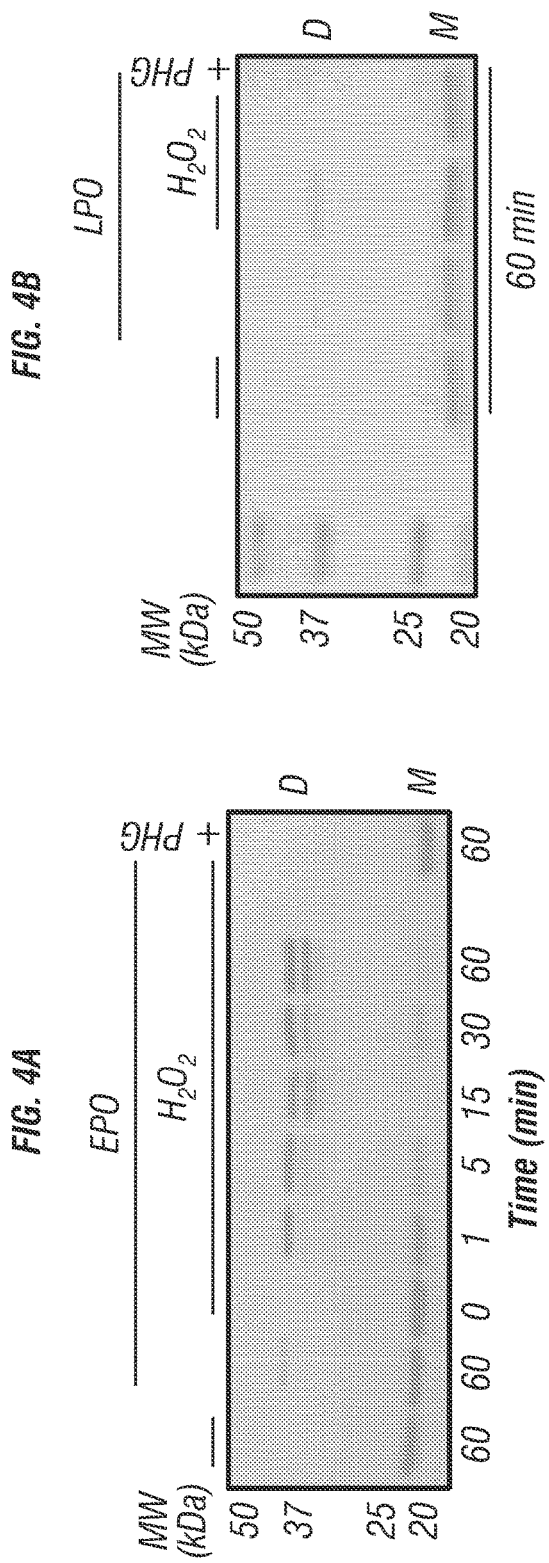
FIG. 4A
FIG. 4B
FIG. 4C
FIG. 4D

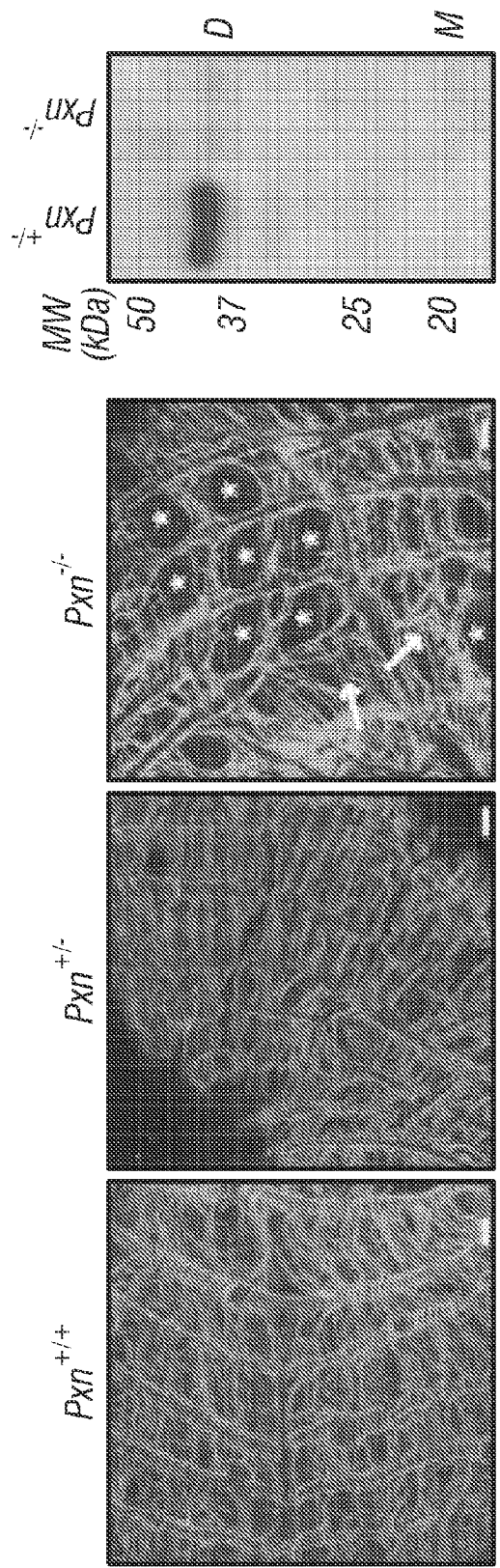
FIG. 6A
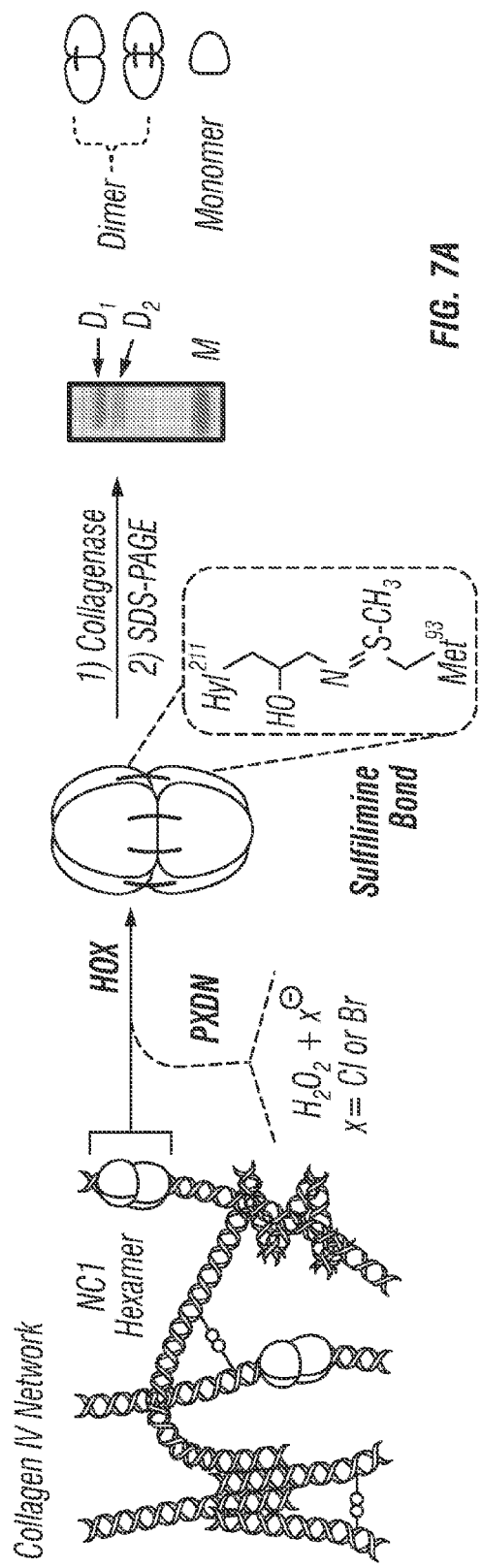
FIG. 6B
FIG. 7A

| Chloride Source (100 mM) | Bromide μM |
|---|---|
| Reagent KCl | 5.91 |
| Br-Free KCl | <0.011 |

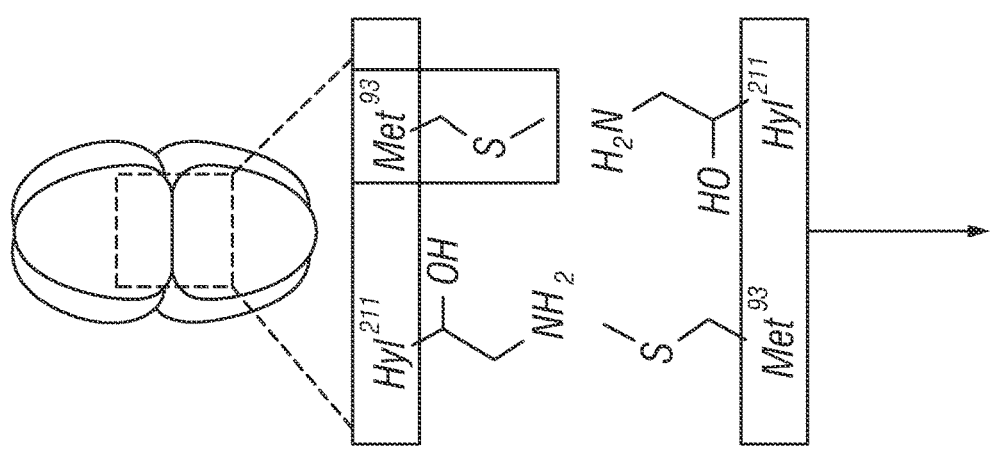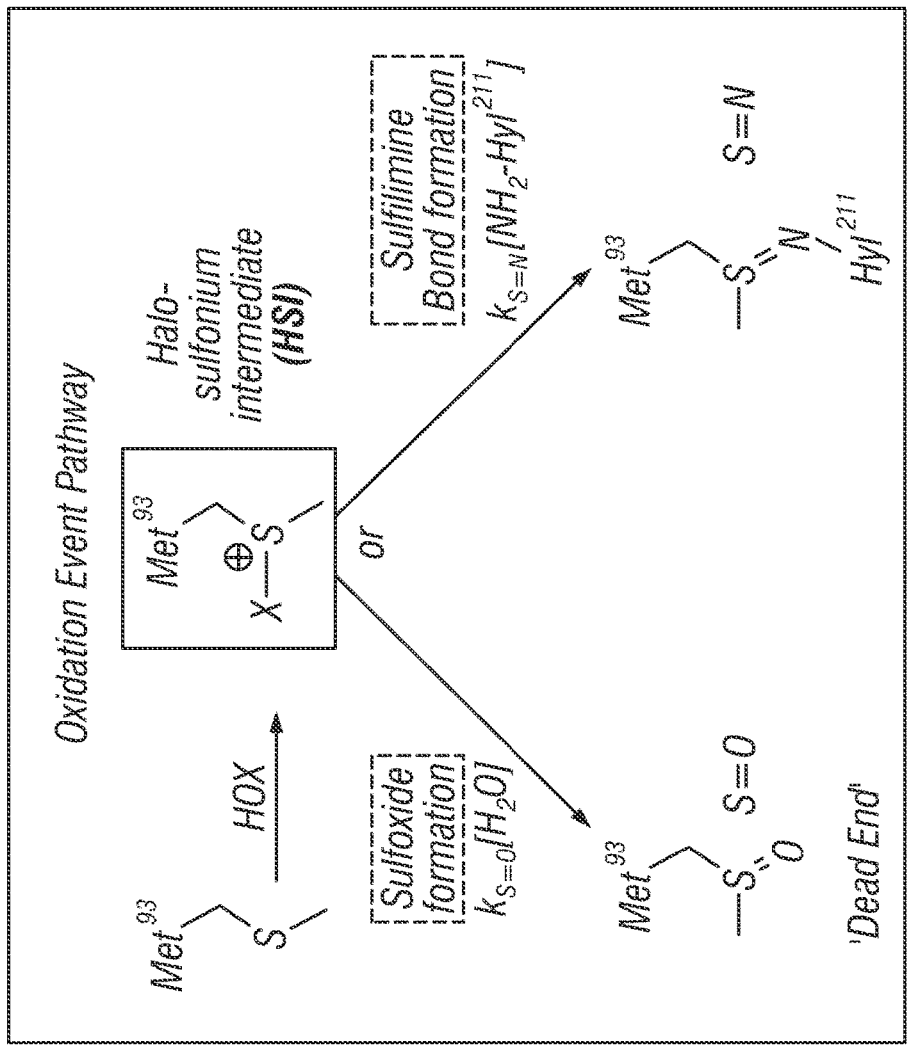
FIG. 9D

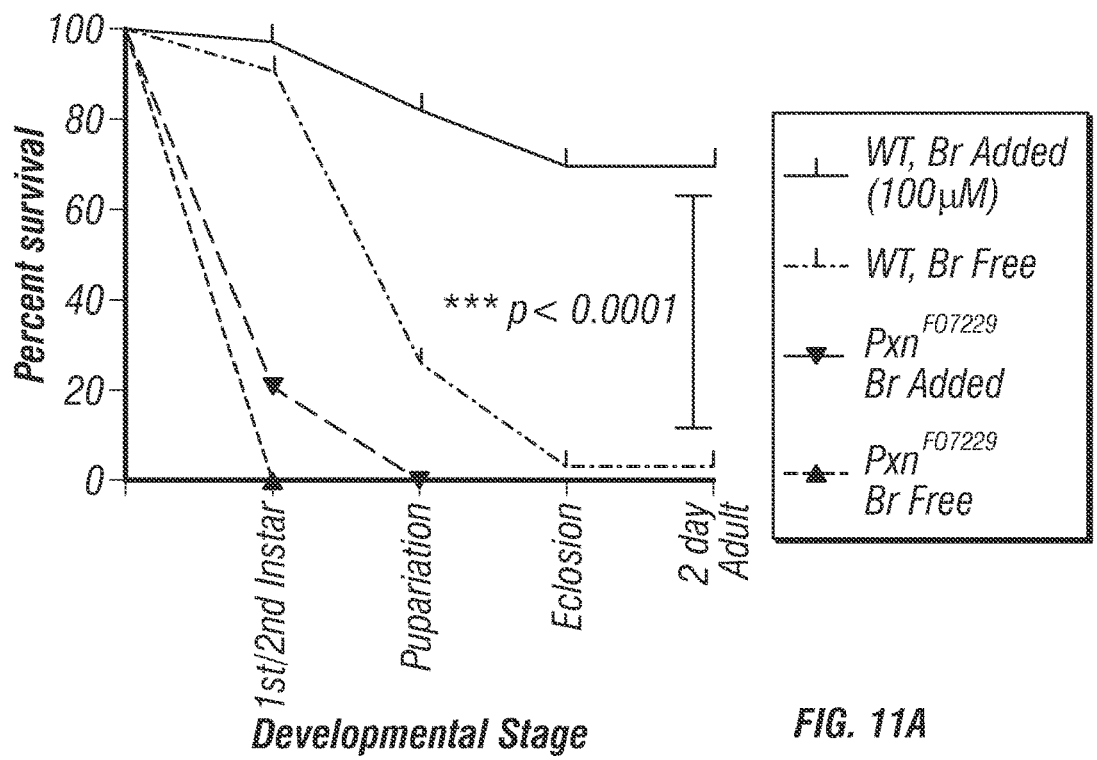
FIG. 11A
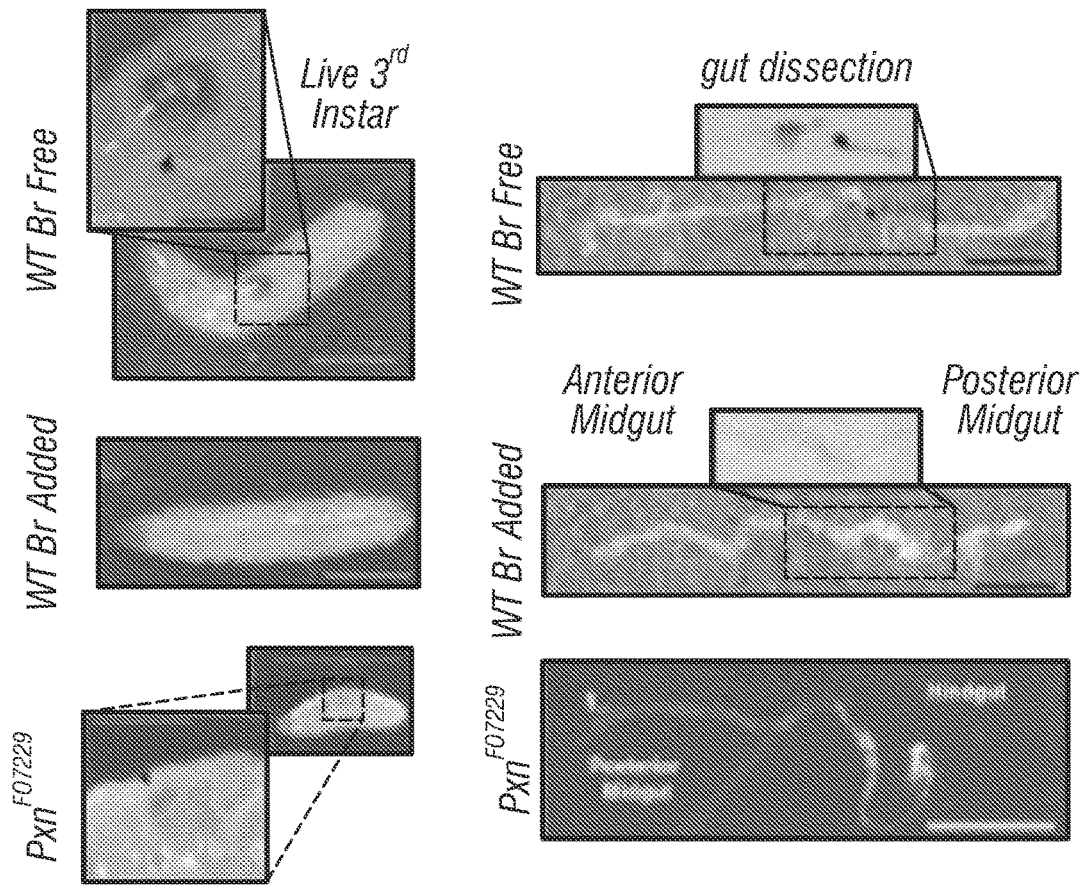
FIG. 11B
FIG. 11C

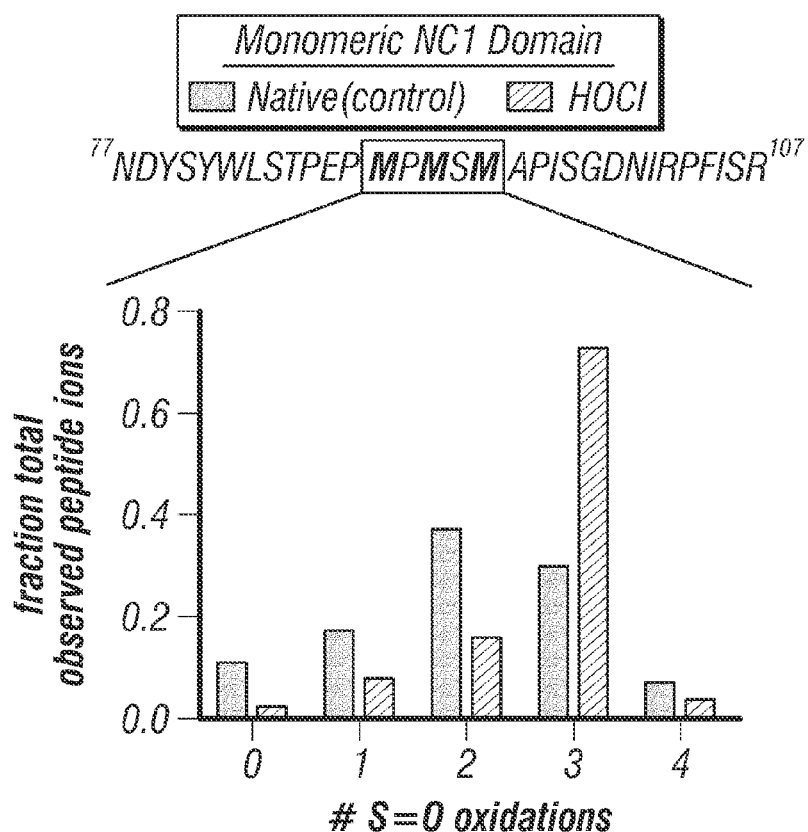
FIG. 15C
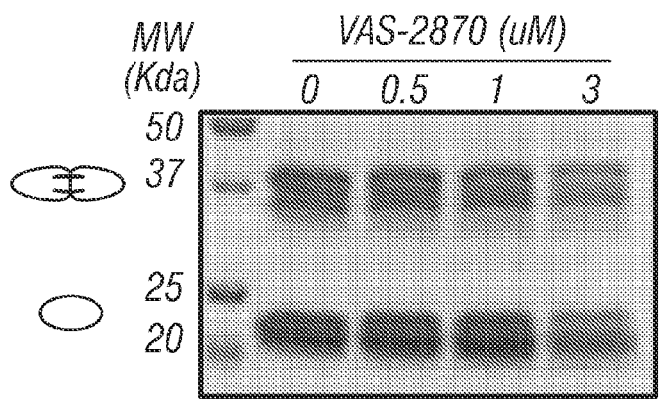
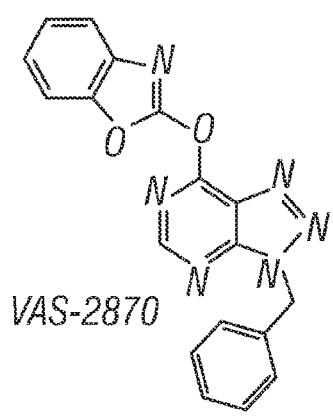
FIG. 16A

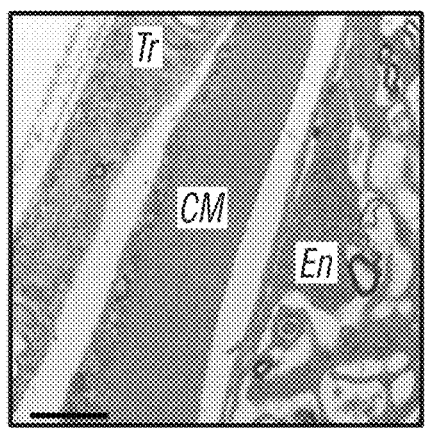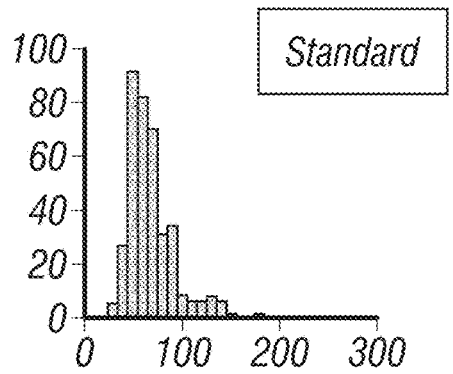
FIG. 17J
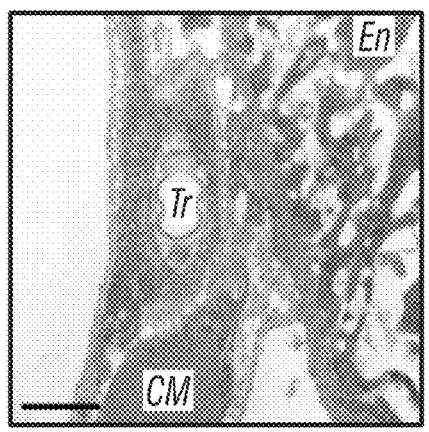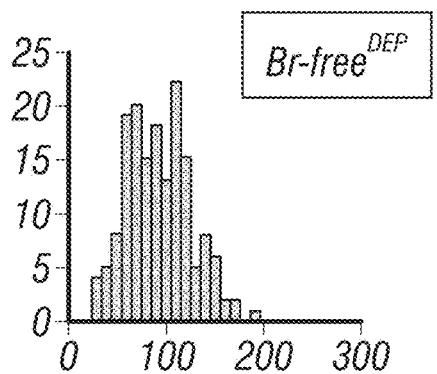
FIG. 17K
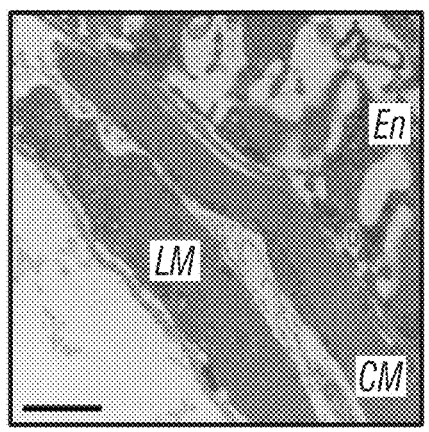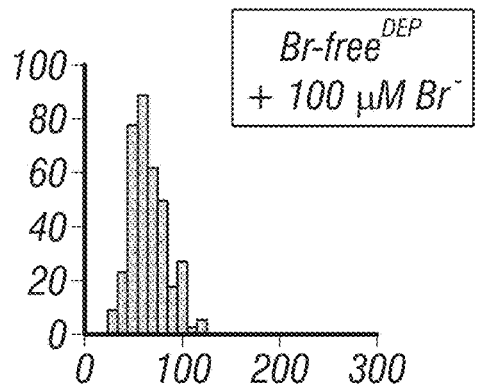
FIG. 17L

METHODS FOR THE PRODUCTION OF COLLAGEN IV

The present application is a national phase application under 35 U.S.C. § 371 of International Application No. PCT/US2014/046507, filed Jul. 14, 2014, which claims benefit of priority to U.S. Provisional Application Ser. No. 61/846,140, filed Jul. 15, 2013, the entire contents of each of which are hereby incorporated by reference.

This invention was made with government support under grant numbers RO1 DK18381, DK18381-3851 and 2PO1 DK065123 awarded by the National Institutes of Health. The government has certain rights in the invention.

BACKGROUND OF THE INVENTION

1. Field of the Invention

The present invention relates generally to the fields of biology and medicine. In particular, the invention relates to methods of producing collagen IV.

2. Description of Related Art

Collagen IV scaffolds are critical components of basement membranes (BM), a specialized form of extracellular matrix that underlies all epithelia in metazoa from sponge to human. Collagen IV molecules are assembled into networks that support the assemblage of BM components (Hudson et al., 2003). The scaffolds confer structural integrity to tissues, provide a foundation for the assembly of other macromolecular components, and serve as ligands for integrin cell-surface receptors that mediate cell adhesion, migration, growth and differentiation (Moser et al., 2009; Hynes, 2002; Yurchenco and Furthmayr, 1984). The networks also participate in signaling events in *Drosophila* development, in the clustering of receptors in the development of mammalian neuromuscular junction (Fox et al., 2007), and they are involved in autoimmune and genetic diseases (Gould et al., 2006; Gould et al., 2005; Hudson et al., 2003).

The collagen IV networks are assembled by oligomerization of triple-helical protomers by end-to-end associations and by intertwining of triple helices through their N- and C-terminal domains (Khoshnoodi et al., 2008; Khoshnoodi et al., 2006). At the C-terminus, two protomers associate through their trimeric non-collagenous (NC1) domains forming a hexamer structure. The protomer-protomer interface is covalently crosslinked, a key reinforcement that strengthens the structural integrity of networks. In the case of humans, the crosslink also confers immune privilege to the collagen IV antigen of Goodpasture autoimmune disease (Vanacore et al., 2008; Borza et al., 2005).

The inventors previously identified a sulfilimine bond ($Met^{93}$-S=N-$Hyl^{211}$) that stabilizes the NC1 trimer-NC1 trimer interaction in which the sulfur atom of methionine-93 ($Met^{93}$) residue from one NC1 domain connects to the ε-nitrogen atom of hydroxylysine-211 ($Hyl^{211}$) of an interacting NC1 domain (Vanacore et al., 2009). The crystal structure of the NC1 hexamer (Sundaramoorthy et al., 2002) demonstrates that this bond plays a critical role in not only stabilizing the quaternary structure of the NC1 hexameric complex but also as reinforcement to the entire collagen IV network. The inventors have also determined that the enzyme responsible for this bond formation is human peroxidasin (PXDN).

The sulfilimine bond likely occurs in diverse metazoan species. NC1 dimer subunits, a signature structural feature indicative of crosslinks, have been identified in collagenase digests of basement membranes including human (Weber et al., 1984), bovine (Weber et al., 1984), dog (Thorner et al., 1996), and mouse (Weber et al., 1984). Furthermore, a phylogenetic analysis of the $Lys^{211}$ and $Met^{93}$ residues, based on a multiple sequence alignment of the NC1 domain across the metazoan phylum (Vanacore et al., 2009; Aouacheria et al., 2006), revealed that the sulfilimine bond may occur in many metazoans, except in hydra, flatworm, sponge, and placozoa. A further comparison of the sequence motif (X-K-A/S/G) that confers hydroxylation of lysyl residues by lysyl hydroxylase (Kivirikko and Pihlajaniemi, 1998) occurs in the NC1 domains of all metazoa except hydra, sponge and placozoa. The motif is also absent in the α4 NC1 domain of human, mouse, bovine and chick, which in the case of bovine $Lys^{211}$ does not undergo hydroxylation and leads to the formation of s-lysyl-methionine crosslink (Vanacore et al., 2008). Phylogenetic analysis suggest that the sulfilimine crosslink is a key biologic feature for tissue organization, development, and maintenance.

Though a great deal has been learned about collagen IV formation and crosslinking, including key enzymes in its regulation, further insights into how to exploit this molecule and the machinery that forms it in therapy remain to be uncovered.

SUMMARY OF THE INVENTION

Thus, in accordance with the present invention, there is provided a method for promoting tissue stability in a target tissue site in a subject in need thereof comprising (a) identifying a subject in need of tissue stabilization; and (b) administering to the subject a bromide salt. The subject may be a non-human animal or a human. The bromide salt may be administered as a sole active ingredient or in combination with a second active agent, such as peroxide, molecular oxygen, electron-accepting compound such as flavin adenine dinucleotide (FAD), hypobromous acid, nicotinamide adenine dinucelotide ($NAD^+$ or NADH), nicotinamide adenine dinucelotide phosphate ($NADP^+$ or NADPH), inosine monophosphate (IMP), guanosine monophosphate (GMP) or a combination thereof. The target concentration of bromide at the target tissue site may be between 1 μM and 1 mM following treatment, such as 5 μm, 10 μm, 15 μm, 20 μm, 25 μm, 30 μm, 50 μm, 75 μm, 100 μm, 150 μm, 200 μm, 250 μm, 300 μm, 400 μm, 500 μm, 600 μm, 700 μm, 800 μm, or 900 μm. In some applications, the said target concentration of bromide may be between 30 μM and 100 μM following treatment, such as 35 μM, 40 μM, 45 μM, 50 μM, 55 μM, 60 μM, 65 μM, 70 μM, 75 μM, 80 μM, 85 μM, 90 μM, or 95 μM.

The subject may suffer from loss, removal, weakening or injury of collagen containing tissues, such as where the loss, removal, weakening or injury involves a medical operation, a trauma, a disease, natural aging, or exposure to an environmental factor. The disease may be periodontal disease or cataracts. The second active agent may be administered such as an antimicrobial agent, such as a hypohalous acid or hypohalite compound. Bromide may be applied in the form of hypobromous acid to the target tissue. The method may further comprise reducing the amount of chloride, iodide, and/or thiocyanate levels in the blood or at the target tissue site in the subject. Administering may comprise oral, intravenous, intra-arterial, subcutaneous, transdermal or topical administration, or systemic administration or administration to or local/regional to a site of healing.

In another embodiment, there is provided a method for predicting the ability of a subject's tissue to recover or heal comprising measuring the concentration of ionic bromide in a sample from the subject, wherein a bromide blood concentration between 1 µM and 1 mM indicates normal healing and recovery as compared to a normal subject, and a bromide blood concentration above or below 1 µM and 1 mM indicates reduced or delayed healing or recovery as compared to a normal subject. The blood concentration is measured directly from blood or serum, or measured indirectly from a sample such as hair, fingernail, toenail, urine, and/or tissue from a site of healing.

The subject may have incurred a medical operation, traumatic wound, chronic wound, natural aging, exposure to an environmental factor or disease. The bromide may be measured through mass spectroscopy, column chromatography, inductively coupled plasma mass spectrometry, neutron activation analysis, energy dispersive x-ray fluorescence, and particle induced x-ray emission. The subject may be a non-human animal or a human. The method may further comprise treating the subject with a bromide salt when the bromide concentration is below 100 µM or when the bromide concentration is below 1 µM. Administering may comprise oral, intravenous, intra-arterial, subcutaneous, transdermal or topical administration, or systemic administration or administration to or local/regional to a site of healing.

In yet another embodiment, there is provided a method for promoting sulfilimine bond formation in tissue or in culture comprising contacting a collagen-containing tissue with a bromide salt. The collagen-containing tissue may be collagen IV-containing tissue. The bromide may be provided as a sole active ingredient or in combination with a second active agent, such as peroxide, molecular oxygen, electron-accepting compound such as flavin adenine dinucleotide (FAD), hypobromous acid, or a combination thereof. The target concentration of bromide in the tissue may be between 1 µM and 1 mM following treatment, such as 5 µm, 10 µm, 15 µm, 20 µm, 25 µm, 30 µm, 50 µm, 75 µm, 100 µm, 150 µm, 200 µm, 250 µm, 300 µm, 400 µm, 500 µm, 600 µm, 700 µm, 800 µm, or 900 µm. The method may further comprise reducing the amount of chloride, iodide, and/or thiocyanate in the tissue. The tissue may have been removed from a subject prior to contacting with the bromide salt, or the tissue may have been generated from a cell line prior to contacting with the bromide salt. The method may further comprise introducing the tissue into a subject after treatment.

In still a further embodiment, there is provided a method of improving tissue development in pre-natal or post-natal infant comprising administering to the infant a bromide salt. The mother of the pre-natal infant may be a smoker, or the mother of the post-natal infant may have been a smoker during pregnancy. Administering may comprise oral, intravenous, intra-arterial, subcutaneous, transdermal or topical administration. The bromide salt may be administered as a sole active ingredient, or in combination with a second active agent, such as peroxide, molecular oxygen, electron-accepting compound such as flavin adenine dinucleotide (FAD), hypobromous acid, nicotinamide adenine dinucelotide ($NAD^+$ or NADH), nicotinamide adenine dinucelotide phosphate ($NADP^+$ or NADPH), inosine monophosphate (IMP), guanosine monophosphate (GMP) or a combination thereof.

The method may further comprise measuring bromide levels in the mother of the infant and providing bromide salt to the mother when the bromide blood concentration is less than 1 µM. The bromide blood concentration may be measured directly in blood or serum, or is estimated from a non-blood/serum sample such as breast milk, hair, fingernail, toenail, or urine. Measuring may comprise mass spectroscopy, column chromatography, inductively coupled plasma mass spectrometry, neutron activation analysis, energy dispersive x-ray fluorescence, and particle induced x-ray emission. The method may further comprise reducing the amount of chloride, iodide, and/or thiocyanate in the infant. The method may further comprise reducing the amount of chloride, iodide, and/or thiocyanate in the mother. The target concentration of bromide in blood of the infant may be between 1 µM and 1 mM following treatment, such as 5 µm, 10 µm, 15 µm, 20 µm, 25 µm, 30 µm, 50 µm, 75 µm, 100 nm, 150 µm, 200 µm, 250 µm, 300 µm, 400 µm, 500 µm, 600 µm, 700 µm, 800 µm, or 900 nm. Alternatively, the target concentration of bromide in blood of the infant may be between 30 µM and 100 µM following treatment, such as 35 µM, 40 µM, 45 µM, 50 µM, 55 µM, 60 nM, 65 µM, 70 µM, 75 µM, 80 µM, 85 µM, 90 µM, or 95 µM. The target concentration of bromide in blood of the mother may be between 1 µM and 1 mM following treatment, such as 5 µm, 10 µm, 15 µm, 20 µm, 25 µm, 30 µm, 50 µm, 75 µm, 100 µm, 150 µm, 200 µm, 250 µm, 300 µm, 400 µm, 500 µm, 600 µm, 700 µm, 800 µm, or 900 µm. Alternatively, the target concentration of bromide in blood of the mother may be between 30 µM and 100 µM following treatment, such as 35 µM, 40 µM, 45 µM, 50 µM, 55 µM, 60 µM, 65 µM, 70 µM, 75 µM, 80 µM, 85 µM, 90 µM, or 95 µM. It is contemplated that any embodiment discussed in this specification can be implemented with respect to any method or composition of the invention, and vice versa. Furthermore, compositions of the invention can be used to achieve methods of the invention.

The use of the word "a" or "an" in the claims and/or the specification may mean "one," but it is also consistent with the meaning of "one or more," "at least one," and "one or more than one."

Throughout this application, the terms "about" and "approximately" indicate that a value includes the inherent variation of error for the device, the method being employed to determine the value, or the variation that exists among the study subjects. In one non-limiting embodiment the terms are defined to be within 10%, preferably within 5%, more preferably within 1%, and most preferably within 0.5%.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The invention may be better understood by reference to one or more of these drawings in combination with the detailed description of specific embodiments presented herein.

(FIG. 1A) Schematic of collagen IVNC1 hexamer with sulfilimine crosslinks bridging the trimer-trimer interface. Upon addition of SDS, the hexamer dissociates into crosslinked dimeric subunits (D) and uncrosslinked monomeric subunits (M). (FIG. 1B) Gel filtration chromatography elution profile of PFHR-9 collagen IVNC1 hexamer (blue) and native, purified placental basement membrane NC1 hexamer (red) run successively. (FIG. 1C) SDS-PAGE of the purified NC1 hexamer with crosslinked dimeric (D) and uncrosslinked monomeric subunits (M). As seen in placental and Engelbreth-Holm-Swarm mouse tumor collagen IV, at least two and occasionally three dimeric subunit bands and one or two monomeric subunit bands were observed[47]. (FIG. 1D) MS of purified PFHR-9 NC1 hexamer revealed a tryptic peptide with a mean observed mass of 5,014.4524. The mass of the Met93-containing peptide added to the Hyl211-containing peptide provides a 'theoretical' mass of 5,016.4460. The difference between the theoretical and observed mass of 1.994 represents the loss of two hydrogens upon sulfilimine bond formation in collagen IV[4]. MOX, methionine sulfoxide, a common oxidation product of methionine. Highlighted M and K residues represent Met93 and Hyl211, respectively, the sulfilimine-crosslinked residues of collagen IV.

FIGS. 2A-C—A basement membrane peroxidase forms the collagen IV sulfilimine bond. (FIG. 2A) Coomassie blue-stained gel after SDS-PAGE of NC1 hexamers isolated from PFHR-9 cells grown in the presence of β-aminopropionitrile (BAPN; 500 μM), putrescine (2.5 mM), phloroglucinol (PHG; 50 μM), methimazole (MMI; 1 mM), potassium iodide (KI; 10 mM) or 3-aminotriazole (3-AT; 10 mM). Collagen IV NC1 hexamer from untreated cells (control) is shown for comparison. Gel is representative of five independent experiments. MW, molecular weight. (FIG. 2B) PFHR-9 basement membrane was allowed to form normally, isolated and treated with PHG (50 μM), MMI (1 mM), KI (10 mM) or 3-AT (10 mM) for 24 h at 37° C. Collagen IV NC1 hexamer was isolated and underwent SDS-PAGE and Coomassie blue staining to visualize sulfilimine crosslink content. (FIG. 2C) Coomassie blue-stained gel after SDS-PAGE of NC1 hexamers after reacting uncrosslinked PFHR-9 basement membrane with H2O2 at varying concentrations for 1 h (left) or for varying durations with 100 μM $H_2O_2$ (right) in 1×PBS. The gel is representative of eight independent experiments. D represents NC1 crosslinked dimeric subunits, and M denotes uncrosslinked monomeric subunits.

FIGS. 3A-E—Peroxidasin forms hypohalous acids and sulfilimine bonds in collagen IV. (FIG. 3A) SDS-PAGE of reactions consisting of 16 nM purified human peroxidasin (PXDN), 500 nM monomeric NC1 hexamer (3 μM potential crosslinks) and 10 μM $H_2O_2$ in 1×PBS. Control reactions without H2O2 or in the presence of the peroxidase inhibitor phloroglucinol (PHG; 50 μM) were also conducted. D represents crosslinked dimeric NC1 subunits, and M denotes uncrosslinked monomeric subunits. MW, molecular weight. (FIG. 3B) Coomassie blue-stained gel after SDS-PAGE of collagen IVNC1 hexamer is shown to illustrate relative amounts of sulfilimine-crosslinked dimeric (D) and uncrosslinked monomeric (M) subunits after incubation of uncrosslinked PFHR-9 basement membranes in varying buffer halide concentrations (Br— or Cl— as K+ salt) with or without 1 mM $H_2O_2$. (FIG. 3C) PXDN-mediated hypohalous acid (HOX) production expressed as nmol hypohalous acid generated per nmol enzyme per min, measured in 1×PBS plus 100 μM NaBr. Values represent mean±s.e.m. (n=3). (FIG. 3D) HOCl production measured directly in 1×PBS without added Br—. Values denote mean±s.e.m. (n=4). PXDN-mediated HOCl generation was significantly greater than that mediated by lactoperoxidase (LPO; *P<0.05, unpaired two-tailed t-test), whereas LPO-mediated generation was not statistically different from zero (§ represents P=0.32; one sample t-test). (FIG. 3E) HOX production, measured in nmol HOX generated per nmol enzyme per min for myeloperoxidase (MPO), eosinophil peroxidase (EPO) or LPO in 1×PBS plus 100 μM NaBr. Values represent mean±s.e.m. (n=3).

FIGS. 4A-D—Hypohalous acids form collagen IV sulfilimine bonds. (FIG. 4A) Five hundred nanomolar collagen IV NC1 hexamer (3 μM potential crosslinks) was incubated alone (control) or with 5 μM hypochlorous (HOCl) or hypobromous acid (HOBr) for 30 min at 37° C. Percentage of dimeric subunit (mean±s.e.m.) as quantified with densitometry of Coomassie blue-stained SDS-PAGE gels (data not shown) increased significantly with HOCl and HOBr treatment (control: n=10, HOCl: n=9, HOBr: n=6; analysis of variance with Tukey's post hoc comparison between groups; *P<0.05 compared to control, and § represents P<0.05 HOCl versus HOBr). (FIGS. 4B-D) 16 nM myeloperoxidase (MPO) (FIG. 4B), eosinophil peroxidase (EPO) (FIG. 4C) or lactoperoxidase (LPO) (FIG. 4D) were reacted with 500 nM NC1 hexamer (3 μM potential crosslinks) for varying time points in 1×PBS with or without 10 μM $H_2O_2$. In the case of LPO, all reactions proceeded for 60 min. Collagen IV-sulfilimine crosslink content was visualized after SDS-PAGE and Coomassie blue staining of the reactions. Each gel is representative of three independent experiments. PHG, phloroglucinol; MW, molecular weight.

(FIG. 5A) Experimental design of 'overlay' experiments. PFHR-9 cells were grown in the presence of phloroglucinol (PHG; 50 μM) to deposit uncrosslinked collagen IV (Col IV) networks. The cells were then removed, and the basement membrane was extracted with 4 M guanidine (Gdn) to inactivate endogenous peroxidasin. Cells stably transfected with human peroxidasin (PXDN) or untransfected HEK293 cells (WT HEK) were plated on top of the PFHR9 basement membrane, which was subsequently analyzed for collagen IV crosslink content. (FIG. 5B) Collagen IV-sulfilimine bond formation in the indicated experimental conditions as shown by stained SDS-PAGE gel. Two (WT HEK cells) or three (PXDN, with or without PHG) out of five independent experiments are shown. MW, molecular weight. (FIG. 5C) Coomassie blue-stained gel of collagen IVNC1 hexamers isolated from uncrosslinked PFHR-9 basement membrane overlaid with HEK293T cells transiently transfected with human peroxidasin cDNA, mouse myeloperoxidase cDNA (MPO), mouse lactoperoxidase cDNA (LPO) or empty vector (Mock). (FIG. 5D) Media from PXDN, MPO, LPO and mock-transfected cells were assayed for peroxidase activity using a tetramethylbenzidine-based colorimetric assay. Activity was expressed relative to peroxidasin (A650 of given peroxidase divided by A650 for peroxidasin).

FIGS. 6A-B—Peroxidasin is critical for collagen IV and basement membrane integrity. (FIG. 6A) Confocal fluorescence microscopy images of *Drosophila* anterior midgut using a collagen IV-GFP protein trap line (vikingG454) to delineate collagen IV distribution. Representative sections from wild-type Pxn+/+, heterozygote Pxn+/− (Pxn+/f07229) and mutant Pxn−/− (Pxnf07229/f07229) flies are shown. Distorted and torn collagen IV networks (arrows) with gross defects ('holes') in the circumferential muscle layer (asterisks) typified Pxn−/− sections. Scale bars, 10 μm. (FIG. 6B) Immunoblot of collagenase-solubilized basement membrane isolated from Drosophila Pxn+/− and Pxn−/− larvae. Pxn−/− mutants show grossly reduced collagen IV immunoreactivity at 20.4% that of the wild-type, whereas Pxn+/− flies maintained collagen IVNC1 content at 82% that of the wild-type (data not shown). Pxn−/− mutants also show a shift in the percentage immunoreactivity, with 42% of total band density in the uncrosslinked form compared to <9% total band density in Pxn+/− flies (data not shown). MW, molecular weight.

FIGS. 7A-C. Sulfilimine bond (S=N) content within the collagen IV network. (FIG. 7A) Diagram of the NC1 domain within the broader collagen IV network, sulfilimine bond, peroxidasin (PXDN) driven production of hypohalous acid (HOX) of either Cl or Br, and analysis of the NC1 domain by SDS-PAGE. Dimeric NC1 (D1 and D2) and monomer (M) are depicted next to their schematic representation. Comparison varying sources of NC1 domains from bovine placental basement membrane (PBM) and glomerular basement membrane (GBM), PFHR-9 murine cell-culture model of matrix, PFHR-9 cells grown in the presence of PHG (phloroglucinol-an irreversible PXDN antagonist) (50 μM), and PHG derived hexamer (1.7 μmol) treated with HOBr and HOCl. (FIG. 7B) Extracted ion current (XIC) based quantitation of S=N cross-linked peptides from D1 and D2 after band exision and in-gel trypsin digest of purified PFHR-9 heaxamer. S=N crosslinked peptides theoretical mass calculated with loss of two hydrogens as a result of the S=N bond (6). Data represents the sum across all observed methionine oxidations and cleavage products or the target peptides after correction to nominalize TIC (total ion counts). (FIG. 7C) Dose-response analysis of PFHR9 matrix grown for 5-8 days in the presence of potassium halide salts and 50 ng/ml ascorbic acid. NC1 domains were solubilized by collagenase, and analyzed by 12% non-reducing SDS-PAGE. S=N content change calculated based on D2 and D1 weighting of change from replicate-controlled dimer content. Points represent mean±S.D. (n=3).

(FIG. 8A) Matrix pellets isolated from KI-treated PFHR9 cell culture were extensively washed into 10 mM phosphate buffer (pH 7.4) supplemented with 100 mM KF to maintain ionic strength. Potassium salts of Cl— or Br— were added in indicated amounts. 1 hr reactions at 37° C. were initiated by addition of $H_2O_2$ to 1 mM and stopped by freezing at −20° C. Coomassie blue-stained gels after collagenase digestion of the samples and SDS-PAGE (FIG. 8B) Schematic of Br-Free chloride salt purification apparatus and setup. Resulting salt was analyzed by ICP-MS for bromide content. Reagent KCl was commercially obtained and unaltered prior to analysis. 100 mM solutions were made with 18MΩ deionized water. (FIG. 8C) Coomassie blue stained gel of collagenase digested PFHR-9 matrix reaction assay. Reaction buffered contained 10 mM phosphate buffer (pH 7.4), 100 mM Br-Free or Commercially obtained reagent grade KCl, as well as 1 mM $H_2O_2$ and 200 μM PHG where appropriate. (FIG. 8D) SDS-PAGE and coomassie blue stain of hPXDN (27.25 nM) and NC1 domain (1.3 μM) reaction and subsequent densiometric quantitation of S=N bond formation stiochiometry in response to NaBr addition. hPXDN and PFHR-9 NC1 domain were prepared and purified as described (5), except with all buffers for all purification steps (dialysis, chromatography, gradient ultracentrifugation) made with Br-Free chloride salts. Reactions were run for 10 minutes at 37° C. with 10 μM $H_2O_2$ as the terminal oxidant. Dose-response curve run in the presence of 1× Br-Free PBS. Reactions were quenched with 0.2 mg/ml Catalase, 20 mM Methionine, and 1 mM PHG. $EC_{50}$ value±95% C.I. from two independent experiments with each data point plotted and fit.

(FIG. 9A) Purified uncrosslinked NC1 hexamer (5 μM) was reacted for 5 minutes at 37° with the indicated amounts of hypohalous acids and analyzed by SDS-PAGE. HOBr was synthesized through a 1 minute reaction with hypochlorite at high pH, with bromide added in 1.1-fold molar excess, followed by dilution to the working concentration at pH 7.4. Values represent mean±S.D. (n=3). (FIG. 7B) Uncrosslinked NC1 hexamer (1.3 μM) in Br-Free PBS was preoxidzed with indicated amounts of HOCl for 1 min at 37 C, followed by post-oxidation with the addition of 8 mol eq. HOBr (or HOCl as a control) which was reacted for an additional minute at 37° C., then quenched with 20 mM methionine. Gel is representative of two experiments (FIG. 9C) XIC analysis of the residual monomeric NC1 subunit following HOCl oxidation (10 mol eq) compared to input NC1 monomer after SDS-PAGE and in-gel trypsin digestion. $^{16}O$ addition to the methionine residues was confirmed by MS3 analysis. (FIG. 9D) Met93 oxidation pathway consistent with experimental data and the resultant enthalphic landscape for S=N bond formation within the NC1 hexamer.

(FIG. 10A) The murine PFHR-9 cell-culture model of basement membranes was cultured for 7 days in the presence of either commercial DMEM+5% FBS or adapted Br-Free DMEM +5% FBS dialyzed against Br-Free HBSS. Media was changed every 24 hours with the addition of 50 μg/ml ascorbic acid and NaBr added where noted. The cell deposited matrix was harvested, collagenase digested, and subjected to SDS-PAGE. NC1 crosslinking content is graphed as the mean±95% C.I. (n=3) with a representative gel depicted. (FIG. 10B) Proposed cyclic model for bromide function based on enzymatic, chemical, and mammalian cell culture data. (FIG. 10C) Mechanism of HOBr driven S=N bond formation within the NC1 hexamer.

FIGS. 11A-C. Bromide is essential for development in Drosophila. (FIG. 11A) Survival curve for Drosophila of WT or peroxidasin hypomorphic allele PxnF07229 in bromide controlled conditions. WT Eggs from 3 day Br-depleted and Br-Added females were collected and transferred to new 35 mm culture dishes filled with 3 ml of vitamin and mineral spiked phytagel as the semi-solid support. 100 μL of Yeast paste±100 μM Br—(200 mg yeast/500 μL $ddH_2O$) was added to the center of each dish. Larvae were transferred to fresh dishes and counted every 24-36 hours. WT flies were reared in the presence of 80 mM total Br-Free NaCl. For Br-Added conditions, both the phytagel and yeast paste were spiked with 100 μM NaBr to ensure constant and consistent exposure. Adults were fed identical food as part of the depletion regime. PxnF07229 homozygous larvae were separated from heterozygous larvae and collected 48 hours after hatching on a Br-Free vs Br-Added plates from parents fed a standard diet. After transfer to these fresh Br-experimental diet plates, they were transferred and counted similarly to the WT larvae under normal 20 mM NaCl conditions. The experimental cohorts [Br-Free (n=34), Br-Added (n=40), Br-Free PxnF07229 (n=14), and Br-Added PxnF07229 (n=19)] were followed until death or 2-days after eclosion of the last fly in the cohort. By Log rank test, the survival difference between WT Br-Free and WT Br-added was highly significant. (FIG. 11B) Representative pictures of live larvae highlight melanotic lesions. Scale bars in the insets represent 200 µm, and in the whole pictures 500 µm. The image of PxnF07229 larvae is from a Br-Added experimental diet. (FIG. 11C) Representative pictures of the corresponding gut dissections to FIG. 11B. Scale bars are 500 µm.

(FIG. 12A) Aspect ratio (arbitrary units) of experimental diets. All eggs deposited in a quadrant of a 55 mm laying cage were moved to a fresh phytagel surface and oriented with dorsal appendages facing the surface for quantitation of the aspect ratio which is calculated by dividing the anterior-posterior axis length by the egg's diameter. Eggs were collected after 168 hours of exposure to standard or experimental diets. Dotted line indicates literature value for egg aspect ratio in Drosophila (24 Differences calculated by Mann Whitney U test $p<0.01$ *$p<0.001$. Mean±95% C.I. is plotted for each group. Scale bar is 500 µm. (FIG. 12B) Percentage of eggs hatching after exposure to experimental diet for 125 hours. All eggs from 1/6 segments of the laying cage were selected and moved to a fresh dish. Segments were sequentially collected until at least 100 total eggs were counted. Data represents Mean±95% C.I. for hatching rate from each segment analyzed. Hatching was assessed 48 hours after counting. Data was analyzed by the Mann-Whitney U test.

(FIG. 13A) Dimer analysis of PFHR9 matrix grown for 5-8 days in the presence of potassium halide salts and 50 µg/ml ascorbic acid. NC1 domains were solubilized by collagenase, resolved by SDS-PAGE using 12% gels under non-reducing conditions, and analyzed via densitometry measurements with ImageJ software and Excel. (FIGS. 13B-D) SDS-PAGE analysis revealed dimer inhibition by KI (FIG. 13B) and KSCN (FIG. 13C), while dimer enhancement was observed with KBr treatment (FIG. 13D).

(FIGS. 14A-B) Titration of KI into the uncrosslinking matrix (FIGS. 14A-B) did not faciliate crosslinking at nano—(FIG. 14A) and micro-molar concentrations (FIG. 14B). Samples were digested with collagenase at 37° C. overnight and visualized by SDS-PAGE using 12% gels under non-reducing conditions with Coomassie staining.

FIGS. 15A-C. Hypobromous Acid is Superior Chemical Catalyst of Collagen IV Sulfilimine Bond Formation. (FIG. 15) Fifty micromolar of hypohalous oxidants were added to 5 µM uncrosslinked NC1 domains, and reacted for 5 minutes at 37° C. before quenching by adding L-methionine to 1 mM final concentration. HOBr, HOI, and HOSCN were each synthesized through a 1 minute reaction at room temperature with hypochlorite at pH>10 where the starting (pseudo) halide anion concentration was present in small excess, followed by dilution to the working concentration at pH 7.4. Experiments were run in triplicate and analyzed by 12% non-reducing SDS-PAGE and ImageJ.

FIGS. 16A-D. Nucleotides Are Sufficient Oxidant Source During Sulfilimine Bond Formation by Peroxidasin. (FIG. 16A) VAS2870 treatment of PFHR-9 cells. Matrix deposited by the cells was collagenase digested and subjected to non-reducing SDS-PAGE and stained with coomassie blue. (FIG. 16B) Cofactor permutation on whole matrix. Uncrosslinked PFHR-9 matrix was incubated with different cofactors for 1 hour with light excluded at 37° C. Digest and staining as in FIG. 16A. DPI=Diphenyleneiodonium (30 µM) a NOX inhibitor. (FIG. 16C) Inosine monophosphate (IMP) and cofactors with purified recombinant peroxidasin and uncross-linked NC1 hexamer. Reactions run at 37° C. for 1 hr with light excluded and FAD (20 µM), NAD/NADH/IMP (100 µM). PHG=Phlouroglucinol (50 µM), an irreversible inhibitor of peroxidasin. Quantification made from SYPRO-Ruby stain. (FIG. 16D) Guanosine monophosphate (GMP) and cofactors reacted as in FIG. 16C. NADP/NADPH/GMP (100 µM).

FIGS. 17A-L. Bromide is essential for development and BM architecture in Drosophila. (FIG. 17A) Generational Br-depletion scheme (FIG. 17B). Generation 1 survival and time-to-development curves for $w^{1118}$ flies on the standard diet vs experimental diets. Embryos from mothers fed a standard diet were placed on the indicated diet, and progeny were scored every 24 hours. The Br-added diet supported the same timing of development as the standard diet, whereas the Br-free diet caused a significant delay (p<0.001 compared to both standard diet and Br-added) prior to pupariation (8 days) and eclosion (14 days). Data plotted as the group median±interquartile range. N=30 for each group. 2 way ANOVA test showed a significant difference for pupariation and eclosion (p<0.001) §=different from standard, ‡=different from Br-added. (FIG. 17C) Generation 2 developmental survival on experimental diets. n>40 for each cohort. Tested by Log-Rank test. (FIG. 17D) Percentage of eggs (mean+/−95% C.I.) completing embryogenesis from mothers reared on Br-free$^{DEP}$ or Br-added$^{DEP}$ diets for 5 days. In the Br-free$^{DEP}$ experimental group, mothers were fed Br-free synthetic diet containing 80 mM total NaCl (Br-free$^{DEP}$) for 3 days prior to egg collection. The Br-added$^{DEP}$ was treated in the same manner except that 100 µM NaBr was added to all food components of the Br-free$^{DEP}$ synthetic diet. Hatching rate differences were observed for eggs collected 3-7 days after maternal diet implementation. Analyzed by the Mann-Whitney U test. (FIG. 17E) Survival curve for $w^{1118}$ flies under Br-free$^{DEP}$ or Br-added$^{DEP}$ dietary conditions. The survival difference between groups was highly significant (log rank test, n=40). (FIG. 17F) Western blot of isolated NC1 domain from larvae treated as in (E), probed with an anti-Drosophila NC1 polyclonal antibody (Extended Experimental Methods). Associated larval Br-content was measured by EINAA. Bonds/hexamer were calculated from the Western blot. (FIGS. 17G-I) Representative images of vkg$^{454}$-GFP$^{+/+}$ larvae reared under the conditions tested in (FIG. 17E) demonstrating holes in the BM (indicated by orange arrows) in the distal posterior midgut of Br-free$^{DEP}$ larvae. Optical sections of mid-lateral gut plane visualizing the circular muscles in cross-section (f-actin stained with phalloidin) surrounded by a collagen IV (vkg$^{454}$-GFP) scaffold and the enterocyte BM. Gut lumen is oriented at the top of the image, anterior-posterior axis is horizontal. *=BM defect. Whole gut images, scale bar=20µ, mid-lateral plane optical sections, scale bar=10µ. (MENTION ASTERICS & ARROWS). (FIGS. 17J-L) Electron micrographs of circular sections through the posterior midgut, focusing on the BM (magenta psuedocolor) beneath the enterocyte (En) near a longitudinal muscle belly (LM). Trachioles (Tr) are occasionally visualized. Standard diet control (FIG. 17J) has thin normal BM. BMs are thickened and irregular in Br-free$^{DEP}$ (FIG. 17K), yet BM thickness is similar to control in Br-added$^{DEP}$ treatments (FIG. 17L). BMs from 15 independent sections for each group were evaluated for thickness and the histograms plotted. Scale bar=0.5μ.

(FIG. 18A) Schematic overview of polarized collagen IV scaffolds (molecular corset, green) which determines aspect ratio in *Drosophila* eggs. (FIG. 18B) Br⁻ concentration effect on egg aspect ratio, in single age-matched cohort of w$^{1118}$ flies, over time. Vertical axis represents mean aspect ratio (±S.E.M). At 192 hours (inset), egg aspect ratio had increased proportionally to Br⁻ concentration, with similar aspect ratios in 15 μM added NaBr and standard diet (measured as 15 μM Br⁻ by NAA). Inset plotted as mean±95% C.I. and significance calculated with the Kruskall-Wallis test. Dotted line indicates egg aspect ratio reported by (Haigo and Bilder, 2011). (FIG. 18C) An irreversible peroxidasin inhibitor, PHG, causes a dose-dependent reduction in the exaggerated egg elongation caused by excess dietary (100 μM) Br⁻. PHG was administered in the food. All wild-type (w$^{1118}$) mothers were from the same cohort and reared identically, then divided into sub-cohorts for exposure to the indicated experimental diet. Significance among the conditions calculated using the Kruskal-Wallis test. Data plotted as mean as mean±95% C.I. (image; scale bar=500 μm). Dotted line indicates reported value for egg aspect ratio (Haigo and Bilder, 2011). All groups also differed significantly when compared individually using Dunn's multiple Comparison testing (p<0.05). (FIG. 18D) Egg aspect ratio on standard diet and synthetic Br-free$^{DEP}$ and Br-added$^{DEP}$ diets. Eggs were collected after mothers were fed indicated diet for 7 days. Differences in egg aspect ratio were observed in eggs collected after 5-7 days of experimental diets. Representative pictures of eggs are shown (scale bar=500 μm). Aspect ratio plotted as mean+/−95% C.I. (graph; Mann Whitney U Test p<0.01 *p<0.001). Dotted line indicates reported value for egg aspect ratio (Haigo and Bilder, 2011). (FIG. 18E) Collagen IV density appears normal in eggs from Br-depleted mothers. BM of stage 8 egg chambers from mothers expressing Vkg-GFP and fed the indicated diet (confocal images). Stage 8 egg chambers on standard and experimental diets. For quantitation, z-stack projections were obtained with 0.580μ slice thickness and identical imaging settings for all diets; fluorescence intensity was summed in areas where the whole thickness of the BM had been observed and normalized to the observational area. n=9 for each group, There was no difference in the medians between the groups by the Kruskal-Wallis test. Data plotted as mean±95% C.I., (image; scale bar=20 μm).

DETAILED DESCRIPTION OF ILLUSTRATIVE EMBODIMENTS

Figure 1A:
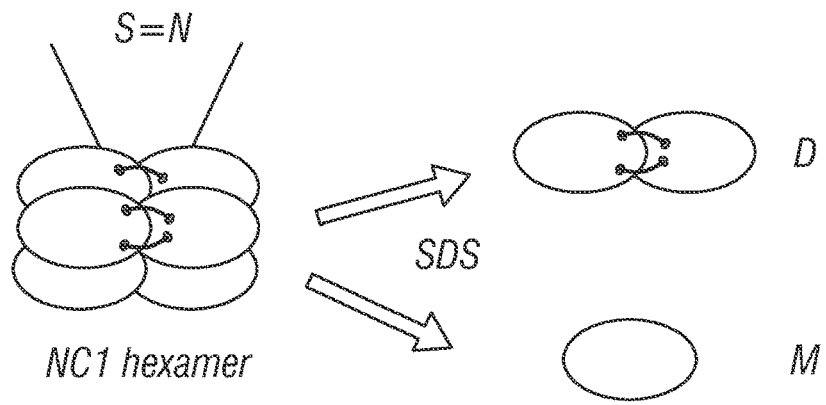
FIGS. 1A-D—PFHR-9 cells produce a basement membrane collagen IV network with sulfilimine crosslinks.

Biologic matrices are essential and decisive factors in tissue development and function. The function of these extracellular surfaces is dependent on their biologic composition, structural organization, and stabilization via chemical crosslinks. Recent discoveries described below allow the control of these matrix characteristics, affecting a range of physiological processes including cellular proliferation and differentiation, tissue growth, vascularization, and disease pathology.

A key structural requirement of these matrices is an embedded collagen IV network that provides critical stability to the matrix (Poschl et al., *Development*, 2004; Gupta et al., *J Cell Biol*, 1997; Borchiellini, Coulon, LeParco, *Mech Dev.*, 1996). The establishment of these networks hinges on the activity of peroxidasin (PXDN), an enzyme that is embedded within matrices and crosslinks the C-termini of collagen IV heterotrimeric protomers. Recent discoveries now allow this enzyme to be functionally inhibited or activated through pharmacologic agents, enabling the fine-tuned control of collagen IV network assembly for the purpose of engineering biologic matrices with specific functional properties.

PXDN is a heme peroxidase that has been recently discovered to promote network assembly by forming sulfilimine bonds between the C-termini of adjoining collagen IV protomers. This catalytic activity is inhibited by pharmacologic treatment with either iodide or thiocyanate ions or with small molecules such as phloroglucinol or methimazole. The enzyme is upregulated during tissue growth, and also guides axon regrowth following neurologic injury (Gotenstein et. al., *Development* 137(21):3603-13, 2010). Its cofactor requirements during sulfilimine bond formation include ionic bromide and an oxidizing source such as peroxide or molecular oxygen in combination with an electron-accepting compound such as flavin adenine dinucleotide. Enzymatic activity can be synthetically enhanced through the administration of one or more of these cofactors. A potential use for these cofactors may be to stimulate PXDN activity to promote wound healing, tissue regeneration, and neurologic growth due to injury or developmental defect. Additionally, stimulating PXDN activity via these cofactors may be used to prevent tissue degeneration due to disease, aging, medical treatment, medical operation, or environmental exposure.

Given the critical role of collagen IV sulfilimine bond in development and human disease, the inventors endeavored to delineate the molecular mechanism of bond formation. Here, they show that PXDN catalyzes sulfilimine bonds directly within basement membranes using hypohalous acid intermediates. These findings represent what is believed to be the first known function for PXDN and highlight a biosynthetic role for conventionally toxic hypohalous oxidants. In addition, a key role for bromide in this reaction is established, providing a previously unknown connection between this chemical entity and tissue stability and repair.

A. Human Peroxidasin and Sulfilimine Crosslinks

1. Human Peroxidasin

Mammalian peroxidases are heme-containing enzymes that serve diverse biological roles, such as host defense and hormone biosynthesis. A mammalian homolog of *Drosophila* peroxidasin belongs to the peroxidase family. Studies have shown that human peroxidasin is present in the endoplasmic reticulum of human primary pulmonary and dermal fibroblasts, and the expression of this protein is increased during transforming growth factor-β1-induced myofibroblast differentiation (Donkó et al., 2009). Myofibroblasts secrete peroxidasin into the extracellular space where it becomes organized into a fibril-like network and colocalizes with fibronectin, thus helping to form the extracellular matrix. Peroxidasin expression has been shown to be increased in a murine model of kidney fibrosis and that peroxidasin localizes to the peritubular space in fibrotic kidneys (Péterfi et al., 2009). The accession nos. for human peroxidasin precursor protein and mRNA are NP_036425.1 and NM_012293.1, respectively, which are hereby incorporated by reference.

2. Sulfilimine Crosslinks

The sulfilimine crosslinks are unique to collagen IV scaffolds, being unknown elsewhere in biology. Their presence is critical to sufficiently stabilizing the scaffold so as to support the diverse biologic functions of collagen IV.

Using mass spectrometry (MS) analyses of crosslinked tryptic (Tp) peptides and a smaller crosslinked post-proline endopeptidase (PPE) peptides, both derived from the α1α2α1 collagen IV network of placenta, it was found that $Lys^{211}$ is modified to hydroxylysine ($Hyl^{211}$) and that $Hyl^{211}$ is covalently linked to $Met^{93}$ forming a sulfilimine crosslink (Vanacore et al. 2009). In the α3α4α5 network, it was found that the sulfilimine crosslink connects the α3 and α5 NC1 domains, but the α4 NC1 domains are crosslinked at $Lys^{211}$ instead of $Hyl^{211}$, indicating that this post-translational hydroxylation modification is not a requirement for crosslink formation.

Up to 6 sulfilimine bonds fasten the interface of the trimeric NC1 domains of two adjoining protomers, reinforcing the quaternary structure of the networks. Furthermore, the sulfilimine bond also occurs in the α3α4α5 collagen IV network because fragmentation pattern of its crosslinked tryptic peptides (Vanacore et al., 2008) is identical to that of the α1α2α1 network described herein. This sulfilimine linkage between Met and Lys/Hyl may not occur only in collagen IV but in other proteins as well.

B. Synthesis of the Collagen IV

In some embodiments, the sulfilimine crosslinks may be synthesized, either chemically or enzymatically, to increase stability of a protein or polymerize a protein. This process may be useful, for example, to network peptides and proteins, or to create a supramolecular complex.

In one embodiment, the sulfilimine crosslink is generated by PXDN enzyme, described above. The enzyme may be admixed with target proteins, or the enzyme may be introduced into a cell by virtue of an expression vector encoding the PXDN gene, where the cell further expresses a target protein for crosslinking.

PXDN forms hypohalous acids during an essential step of its catalytic mechanism, resulting in the production of hypobromous acid (HOBr) which is directly responsible for sulfilimine bond formation. Collagen IV sulfilimine bonds can be formed chemically via treatment with the hypohalous reagent, HOBr. This biosynthetic function for hypohalous acids stands in contrast to their common destructive roles within immune inflammation. Their controlled production within biologic matrices, via pharmacologic regulation of PXDN activity, allows the design of synthetic matrices that inhibit microbial growth as well as promote tissue growth and function through properly assembled collagen IV networks. This biomaterial could be used as a topical treatment for wound healing and/or non-systemic infections in patients.

The composition of assembled matrices may be altered in culture, using traditional methods for forming collagen IV matrices such as via the murine cell line PHFR9. Established collagen IV matrices have been supplemented with additional PXDN by culturing enzyme-expressing cells overtop the existing matrix, so that exogenous enzyme was deposited into the matrix with preservation of enzymatic activity. This may be particularly useful in designing matrices with enhanced anti-microbial properties.

C. Modulation of Collagen IV and Crosslinking by Bromide

A bromide is a chemical compound containing a bromide ion or ligand. This is a bromine atom with an ionic charge of 1 ($Br^-$); for example, in cesium bromide, cesium cations ($Cs^+$) are electrically attracted to bromide anions ($Br^-$) to form the electrically neutral ionic compound CsBr. The term "bromide" can also refer to a bromine atom with an oxidation number of −1 in covalent compounds such as sulfur dibromide ($SBr_2$).

Bromide compounds, especially potassium bromide, were frequently used as sedatives in the 19th and early 20th century. Their use in over-the-counter sedatives and headache remedies (such as Bromo-Seltzer) in the United States extended to 1975, when bromides were withdrawn as ingredients, due to chronic toxicity. Indeed, chronic toxicity from bromide occurs when bromide levels in serum approach 12 mM (van Leeuwen and Sangster, 1987) can result in bromism, a syndrome with multiple neurological symptoms. Bromide toxicity can also cause a type of skin eruption.

The bromide ion displays antiepileptic activity when administered at high concentrations, yet their medical use as antiepileptic therapeutics are rare. Bromide is occasionally used in veterinary medicine, sometimes in the form of potassium bromide (KBr). Bromide ion is excreted by the kidneys. The half-life of bromide in the human body (12 days) is long compared with many pharmaceuticals, making dosing difficult to adjust (a new dose may require several months to reach equilibrium). Bromide ions are occasionally used as counter ions in modern pharmaceutical treatments for pain or other neurologic indications, but no prior art is known that demonstrates or suggests that bromide may be therapeutically used to promote tissue stabilization. Bromide ion concentrations in the cerebrospinal fluid are about 30% of those in blood, and are strongly influenced by the body's chloride intake and metabolism.

Since bromide is still used in veterinary medicine (particularly to treat seizures in dogs) and as a counter ion in modern pharmaceuticals in the United States, certain specialized diagnostic labs can routinely measure blood bromide levels. However, this is not a conventional test in human medicine in the U.S., since (as noted) it is no longer available in over-the-counter sedatives. Therapeutic bromide levels are measured in European countries like Germany, where bromide is still used therapeutically in human epilepsy.

Lithium bromide was used as a sedative beginning in the early 1900s, but it fell into disfavor in the 1940s, possibly when some heart patients died after using a salt substitute (see lithium chloride). Like lithium carbonate and lithium chloride it was used as treatment for bipolar disorder.

Bromide is needed by eosinophils, which use it to generate antiparasitic brominating compounds such as hypobromite, by the action of eosinophil peroxidase, a haloperoxidase enzyme which is able to use chloride, but preferentially uses bromide when available. Despite this use by the body and prior to the invention presented herein, bromide was not been known to be strictly necessary for animal life, as its known functions were generally understood to be replaced (though in some cases not as well) by chloride which is present in humans at much higher concentrations than bromide.

Bromide ions are required for collagen IV sulfilimine bond formation, being oxidized by PXDN into its catalytic form of HOBr, and carries out a critical function in the stabilization of tissue architecture. This function is necessary for animal life and represents the first essential function for the bromide ion in mammalian biology. The magnitude of this finding is only truly appreciated by independently considering the requirement for this specific halogen as well as the biosynthetic activity of the oxidant. On the one hand, the element bromine has lacked any essential function within animals prior to this discovered sulfilmine activity, with resulting ambiguity regarding its role in biology. Furthermore, its biologic relevance is often overshadowed by the significantly greater serum chloride concentration and the chemical reactivity of thiocyanate. On the other hand, hypohalous acids are commonly described for their capacity as destructive oxidants; useful within the immunologic toolkit but pathologic when unregulated as seen in atherosclerosis and other diseases associated with oxidative stress. The anabolic activity of HOBr during sulfilimine catalysis is partially analogous to the activity of oxidized iodide during thyroid hormone synthesis. Yet structural analysis of the products reveals an iodinated hormone that contrasts with the non-halogenated sulfilimine bond, strongly suggesting the utilization of distinct chemistry. In sufilimine bond formation, Br⁻ acts as a chemical catalyst and hypobromous acid the reactive intermediate.

The average concentration of bromide in human blood (e.g., Queensland, Australia) is 5.3±1.4 mg/L and varies with age and gender. Much higher levels may indicate exposure to brominated chemicals (e.g., methyl bromide). However, since bromide occurs in relatively high concentration in seawater and many types of seafood, bromide concentrations in the blood are heavily influenced by seafood contributions to the diet.

Target concentrations following treatment are anywhere from 1 μM and 1 mM in either blood or the tissue being treated. Particular values include 5 μm, 10 μm, 15 μm, 20 μm, 25 μm, 30 μm, 50 μm, 75 μm, 100 μm, 150 μm, 200 μm, 250 μm, 300 μm, 400 μm, 500 lam, 600 μm, 700 μm, 800 μm, or 900 μm.

D. Tissue Disease States and Disorders

In general, the present disclosure deals with wound healing, wound repair, or tissue stabilization. The following is a general discussion of such disorders.

Wound healing is an intricate process in which the skin (or another organ-tissue) repairs itself after injury. In normal skin, the epidermis (outermost layer) and dermis (inner or deeper layer) exists in a steady-state equilibrium, forming a protective barrier against the external environment. Once the protective barrier is broken, the normal (physiologic) process of wound healing is immediately set in motion. The classic model of wound healing is divided into three or four sequential yet overlapping phases: (1) hemostasis, (2) inflammatory, (3) proliferative and (4) remodeling. Upon injury to the skin, a set of complex biochemical events takes place in a closely orchestrated cascade to repair the damage. Within minutes post-injury, platelets (thrombocytes) aggregate at the injury site to form a fibrin clot. This clot acts to control active bleeding (hemostasis). Wounds may be acute, such as from trauma or surgery, or chronic.

In accordance with the present invention, one can treat wounds by regulating peroxidasin using modulators disclosed herein. Treatment of wounds depends on how severe the wound is, its location, and whether other areas are affected. If another condition is causing problems with wound healing, it is important to treat or control this problem. A caregiver may prescribe antibiotics to fight infection, either orally, i.v., or applied directly on the wound area. Palliative care such as for pain, swelling and fever are often prescribed. Wound care is essential as well and includes cleansing, debridement and wound dressing. Dressings are particularly important to protect the wound from further injury and infection. These may also help give pressure to decrease swelling. Dressings may be in the form of bandages, films, or foams. They may contain certain substances that may help promote faster healing. Sometimes, skin taken from another part of the body may be used to close a large wound. The skin may also be man-made, which contains special cells needed to repair damaged tissues. Additional treatments include hyperbaric oxygen therapy (HBO), negative pressure therapy (also called vacuum-assisted closure or "VAC"), or creams, ointments, or medicines with special solutions which help in wound healing may be applied to the wound.

Other conditions are contemplated as well, including developmental conditions that result in reduced tissue stability. Genetic or acquired diseases resulting in loss of tissue integrity, natural aging, or exposure to an environmental factor that affect tissue integrity and stability are all disorders amenable to treatment with bromide and the secondary agent discussed herein.

Alport syndrome or hereditary nephritis is a genetic disorder characterized by glomerulonephritis, endstage kidney disease, and hearing loss. Alport syndrome can also affect the eyes (lenticonus). The presence of blood in the urine (hematuria) is almost always found in this condition. It is associated with defects in collagen (type IV).

E. Pharmaceutical Formulations and Routes and Modes of Administration

The agents of the present disclosure may be administered by a variety of methods, e.g., orally or by injection (e.g. subcutaneous, intravenous, intraperitoneal, etc.). Depending on the route of administration, the active compounds may be coated in a material to protect the compound from the action of acids and other natural conditions which may inactivate the compound. They may also be administered by continuous perfusion/infusion of a disease or wound site.

To administer the agents by other than parenteral administration, it may be necessary to coat the compound with, or co-administer the compound with, a material to prevent its inactivation. For example, the therapeutic compound may be administered to a patient in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al., 1984).

The agents may also be administered parenterally, intraperitoneally, intraspinally, or intracerebrally. Dispersions can be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (such as, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating the therapeutic compound in the required amount in an appropriate solvent with one or a combination of ingredients enumerated above, as required, followed by filtered sterilization. Generally, dispersions are prepared by incorporating the therapeutic compound into a sterile carrier which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (i.e., the therapeutic compound) plus any additional desired ingredient from a previously sterile-filtered solution thereof.

The agents can be orally administered, for example, with an inert diluent or an assimilable edible carrier. The therapeutic compound and other ingredients may also be enclosed in a hard or soft shell gelatin capsule, compressed into tablets, or incorporated directly into the subject's diet. For oral therapeutic administration, the therapeutic compound may be incorporated with excipients and used in the form of ingestible tablets, buccal tablets, troches, capsules, elixirs, suspensions, syrups, wafers, and the like. The percentage of the therapeutic compound in the compositions and preparations may, of course, be varied. The amount of the therapeutic compound in such therapeutically useful compositions is such that a suitable dosage will be obtained.

It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical carrier. The specification for the dosage unit forms of the invention are dictated by and directly dependent on (a) the unique characteristics of the therapeutic compound and the particular therapeutic effect to be achieved, and (b) the limitations inherent in the art of compounding such a therapeutic compound for the treatment of a selected condition in a patient.

Active compounds are administered at a therapeutically effective dosage sufficient to treat a condition associated with a condition in a patient. A "therapeutically effective amount" preferably reduces the amount of symptoms of the condition in the infected patient by at least about 20%, more preferably by at least about 40%, even more preferably by at least about 60%, and still more preferably by at least about 80% relative to untreated subjects. For example, the efficacy of a compound can be evaluated in an animal model system that may be predictive of efficacy in treating the disease in humans, such as the model systems shown in the examples and drawings.

The actual dosage amount of an agent of the present disclosure or composition comprising an inhibitor of the present disclosure administered to a subject may be determined by physical and physiological factors such as age, sex, body weight, severity of condition, the type of disease being treated, previous or concurrent therapeutic interventions, idiopathy of the subject and on the route of administration. These factors may be determined by a skilled artisan. The practitioner responsible for administration will typically determine the concentration of active ingredient(s) in a composition and appropriate dose(s) for the individual subject. The dosage may be adjusted by the individual physician in the event of any complication.

In certain embodiments, a pharmaceutical composition of the present disclosure may comprise, for example, at least about 0.1% of a compound of the present disclosure. In other embodiments, the compound of the present disclosure may comprise between about 2% to about 75% of the weight of the unit, or between about 25% to about 60%, for example, and any range derivable therein.

Single or multiple doses of the agents are contemplated. Desired time intervals for delivery of multiple doses can be determined by one of ordinary skill in the art employing no more than routine experimentation. As an example, subjects may be administered two doses daily at approximately 12 hour intervals. In some embodiments, the agent is administered once a day.

The agent(s) may be administered on a routine schedule. As used herein a routine schedule refers to a predetermined designated period of time. The routine schedule may encompass periods of time which are identical or which differ in length, as long as the schedule is predetermined. For instance, the routine schedule may involve administration twice a day, every day, every two days, every three days, every four days, every five days, every six days, a weekly basis, a monthly basis or any set number of days or weeks there-between. Alternatively, the predetermined routine schedule may involve administration on a twice daily basis for the first week, followed by a daily basis for several months, etc.

A. Devices for Delivery of Therapeutic Compounds

The present invention involves, in some aspects, the provision of devices for delivery of bromide to wounds. In general, it is contemplated that any device or material that is brought into contact with a wound is a suitable vehicle for delivering bromide. The following devices/materials are exemplary in nature and are not meant to be limiting.

1. Wound Dressings

The present invention in one aspect, provides for various wound dressings that incorporate or have applied thereto the bromide compounds of the present invention. Dressings have a number of purposes, depending on the type, severity and position of the wound, although all purposes are focused towards promoting recovery and preventing further harm from the wound. Key purposes of are dressing are to seal the wound and expedite the clotting process, to soak up blood, plasma and other fluids exuded from the wound, to provide pain relieving effect (including a placebo effect), to debride the wound, to protect the wound from infection and mechanical damage, and to promote healing through granulation and epithelialization.

The following list of commercial dressings includes those that may be employed in accordance with the present invention: Acticoat, Acticoat 7, Actisorb Silver 220, Algisite M, Allevyn, Allevyn Adhesive, Allevyn Cavity, Allevyn Compression, Allevyn Heel, Allevyn Sacrum, Allevyn cavity wound dressing, Aquacel, Aquacel AG, Aquacel ribbon, Bactigras, Biatain Adhesive, Bioclusive, Biofilm, Blenderm, Blue line webbing, Bordered Granuflex, Calaband, Carbonet, Cavi-care, Cellacast Xtra, Cellamin, Cellona Xtra, Cellona elastic, Chlorhexitulle, Cica-Care, Cliniflex odour control dressing, Clinisorb odour control dressing, Coban, Coltapaste, Comfeel Plus, Comfeel Plus pressure relieving dressing, Comfeel Plus transparent dressing, Comfeel Plus ulcer dressing, Comfeel seasorb dressing, Comfeel ulcer dressing, Contreet Non-Adhesive, Crevic, Cutinova Hydro, Cutinova Hydro Border, Debrisan absorbent pad, Debrisan beads, Debrisan paste, Delta-Cast Black Label, Delta-Cast conformable, Delta-Lite S, Duoderm extra thin, Durapore, Elastocrepe, Elset/Elset 'S', Flamazine, Fucidin Intertulle, Geliperm granulated gel, Geliperm sheet, Granuflex (Improved formulation), Granuflex extra thin, Granugel, Gypsona, Gypsona S, Hypafix, Icthaband, Icthopaste, Inadine, Intrasite Gel, Iodoflex, Iodosorb, Iodosorb ointment, Jelonet, K-Band, K-Lite, K-PLUS, Kaltocarb, Kaltostat, Kaltostat Fortex, Kaltostat cavity dressing, LarvE (Sterile Maggots), Lestreflex, Lyofoam, Lyofoam 'A', Lyofoam C, Mefix, Melolin, Mepiform, Mepilex, Mepilex AG, Mepilex Border, Mepilex Border Lite, Mepilex Border Sacrum, Mepilex Heel, Mepilex Lite, Mepilex Transfer, Mepitac, Mepitel, Mepore, Mepore Pro, Mesitran, Mesorb, Metrotop, Microfoam, Micropore, Opsite Flexigrid, Opsite IV 3000, Orthoflex, Oxyzyme, Paratulle, Polymem, Polymem Island & Shapes, Polymem Max, Polymem Silver, ProGuide, Profore, Promogran, Quinaband, Release, Scotchcast Plus, Scotchcast Softcast, Serotulle, Setopress, Silastic foam, Silicone N-A, Sofra-Tulle, Sorbsan, Sorbsan Plus, Sorbsan SA, Sorbsan Silver, Sorbsan Silver Plus Self Adhesive, Spenco 2nd Skin, Spyroflex, Spyrosorb, Tarband, Tegaderm, Tegaderm Plus, Tegagel, Tegapore, Tegasorb, Telfa, Tensopress, Tielle, Tielle Lite, Tielle Plus, Tielle Plus Borderless, Transpore, Unitulle, Veinoplast, Veinopress, Versiva, Vigilon, Viscopaste PB7, Xelma, and Zincaband.

A typical (sterile) dressing is one made of a film, foam, semi-solid gel, pad, gauze, or fabric. More particularly, sterile dressings are made of silicone, a fibrin/fibrinogen matrix, polyacrylamide, PTFE, PGA, PLA, PLGA, a polycaprolactone or a hyaluronic acid, although the number and type of materials useful in making dressings is quite large. Dressing may further be described as compression dressings, adherent dressing and non-adherent dressings.

Dressings may advantageously include other materials active or inert. Such materials include gelatin, silver, cellulose, an alginate, collagen, a hydrocolloid, a hydrogel, a skin substitute, a wound filler, a growth factor, an antibody, a protease, a protease inhibitor, an antibacterial peptide, an adhesive peptide, a hemostatic agent, living cells, honey, nitric oxide, a corticosteroid, a cytotoxic drug, an antibiotic, an antimicrobial, an antifungal, an antiseptic, nicotine, an anti-platelet drug, an NSAID, colchicine, an anti-coagulant, a vasoconstricting drug or an immunosuppressive.

Wound dressings may also be part of a larger device, such as one that permits fixation of the dressing to a wound, such as an adhesive or a bandage. Dressings/devices may also include other features such as a lubricant, to avoid adhesion of the dressing to the wound, an absorber to remove seepage from the wound, padding to protect the wound, a sponge for absorbance or protection, a wound veil, an odor control agent, and/or a cover.

The bromide agent, or any other agent, may be applied to a dressing, or disposed in a dressing, by virtue of its introduction into or onto the dressing in a liquid, a salve, an ointment, a gel or a powder. Alternatively, the bromide agent or other agent may be added to a discrete element of a dressing (a sheet or film) that is included in the dressing during its manufacture.

Devices may also include a port, such as one providing operable connection between said sterile dressing and a tube, as well as a cover providing an airtight seal to or around a wound surface. Such embodiments are particularly useful in negative pressure wound therapy methods and devices.

2. Sutures

A surgical suture is a medical device used to hold body tissues together after an injury or surgery. It generally a length of thread, and it attached to a needle. A number of different shapes, sizes, and thread materials have been developed over time. The present invention envisions the coating or impregnating of sutures with bromide compounds.

The first synthetic absorbable was based on polyvinyl alcohol in 1931. Polyesters were developed in the 1950s, and later the process of radiation sterilization was established for catgut and polyester. Polyglycolic acid was discovered in the 1960s and implemented in the 1970s. Today, most sutures are made of synthetic polymer fibers, including the absorbables polyglycolic acid, polylactic acid, and polydioxanone as well as the non-absorbables nylon and polypropylene. More recently, coated sutures with antimicrobial substances to reduce the chances of wound infection have been developed. Sutures come in very specific sizes and may be either absorbable (naturally biodegradable in the body) or non-absorbable. Sutures must be strong enough to hold tissue securely but flexible enough to be knotted. They must be hypoallergenic and avoid the "wick effect" that would allow fluids and thus infection to penetrate the body along the suture tract.

All sutures are classified as either absorbable or non-absorbable depending on whether the body will naturally degrade and absorb the suture material over time. Absorbable suture materials include the original catgut as well as the newer synthetics polyglycolic acid (Biovek), polylactic acid, polydioxanone, and caprolactone. They are broken down by various processes including hydrolysis (polyglycolic acid) and proteolytic enzymatic degradation. Depending on the material, the process can be from ten days to eight weeks. They are used in patients who cannot return for suture removal, or in internal body tissues. In both cases, they will hold the body tissues together long enough to allow healing, but will disintegrate so that they do not leave foreign material or require further procedures. Occasionally, absorbable sutures can cause inflammation and be rejected by the body rather than absorbed.

Non-absorbable sutures are made of special silk or the synthetics polypropylene, polyester or nylon. Stainless steel wires are commonly used in orthopedic surgery and for sternal closure in cardiac surgery. These may or may not have coatings to enhance their performance characteristics. Non-absorbable sutures are used either on skin wound closure, where the sutures can be removed after a few weeks, or in stressful internal environments where absorbable sutures will not suffice. Examples include the heart (with its constant pressure and movement) or the bladder (with adverse chemical conditions). Non-absorbable sutures often cause less scarring because they provoke less immune response, and thus are used where cosmetic outcome is important. They must be removed after a certain time, or left permanently.

In recent years, topical cyanoacrylate adhesives ("liquid stitches") have been used in combination with, or as an alternative to, sutures in wound closure. The adhesive remains liquid until exposed to water or water-containing substances/tissue, after which it cures (polymerizes) and forms a flexible film that bonds to the underlying surface. The tissue adhesive has been shown to act as a barrier to microbial penetration as long as the adhesive film remains intact. Limitations of tissue adhesives include contraindications to use near the eyes and a mild learning curve on correct usage.

Cyanoacrylate is the generic name for cyanoacrylate based fast-acting glues such as methyl-2-cyanoacrylate, ethyl-2-cyanoacrylate (commonly sold under trade names like Superglue™ and Krazy Glue™) and n-butyl-cyanoacrylate. Skin glues like Indermil® and Histoacryl® were the first medical grade tissue adhesives to be used, and these are composed of n-butyl cyanoacrylate. These worked well but had the disadvantage of having to be stored in the refrigerator, were exothermic so they stung the patient, and the bond was brittle. Nowadays, the longer chain polymer, 2-octyl cyanoacrylate, is the preferred medical grade glue. It is available under various trade names, such as LiquiBand®, SurgiSeal®, FloraSeal®, and Dermabond®. These have the advantages of being more flexible, making a stronger bond, and being easier to use. The longer side chain types, for example octyl and butyl forms, also reduce tissue reaction.

3. Negative Pressure Wound Therapy

Negative pressure wound therapy (NPWT), also known as topical negative pressure, sub-atmospheric pressure dressings or vacuum sealing technique, is a therapeutic technique used to promote healing in acute or chronic wounds, fight infection and enhance healing of burns. A vacuum source is used to create sub-atmospheric pressure in the local wound environment. The wound is sealed to prevent dehiscence with a gauze or foam filler dressing, and a drape and a vacuum source applies negative pressure to the wound bed with a tube threaded through the dressing. The vacuum may be applied continuously or intermittently, depending on the type of wound being treated and the clinical objectives. Intermittent removal of used instillation fluid supports the cleaning and drainage of the wound bed and the removal of infectious material.

NPWT has multiple forms which mainly differ in the type of dressing used to transfer NPWT to the wound surface, and include both gauze and foam. Gauze has been found to effect less tissue ingrowth than foam. The dressing type depends on the type of wound, clinical objectives and patient. For pain sensitive patients with shallow or irregular wounds, wounds with undermining or explored tracts or tunnels, and for facilitating wound healing, gauze may be a better choice for the wound bed, while foam may be cut easily to fit a patient's wound that has a regular contour and perform better when aggressive granulation formation and wound contraction is the desired goal. The technique is often used with chronic wounds or wounds that are expected to present difficulties while healing (such as those associated with diabetes or when the veins and arteries are unable to provide or remove blood adequately).

4. Transdermal Delivery

Certain embodiments of the present invention pertain to transdermal or transcutaneous delivery devices for delivery of bromide comprising a patch. The therapeutic agent is embedded in or in contact with a surface of the patch. The patch can be composed of any material known to those of ordinary skill in the art. Further, the patch can be designed for delivery of the therapeutic agent by application of the patch to a body surface of a subject, such as a skin surface, the surface of the oral mucosa, a wound surface, or the surface of a tumor bed. The patch can be designed to be of any shape or configuration, and can include, for example, a strip, a bandage, a tape, a dressing (such as a wound dressing), or a synthetic skin. Formulations pertaining to transdermal or transcutaneous patches are discussed in detail, for example, in U.S. Pat. Nos. 5,770,219, 6,348,450, 5,783,208, 6,280,766 and 6,555,131, each of which is herein specifically incorporated by reference into this section and all other sections of the specification.

In some embodiments, the device may be designed with a membrane to control the rate at which a liquid or semi-solid formulation of the therapeutic agent can pass through the skin and into the bloodstream. Components of the device may include, for example, the therapeutic agent dissolved or dispersed in a reservoir or inert polymer matrix; an outer backing film of paper, plastic, or foil; and a pressure-sensitive adhesive that anchors the patch to the skin. The adhesive may or may not be covered by a release liner, which needs to be peeled off before applying the patch to the skin. In some embodiments, the therapeutic agent is contained in a hydrogel matrix.

In some embodiments, it is desirable to transport the bromide through the skin. Accordingly, topical patch formulations may include a skin permeability mechanism such as: a hydroxide-releasing agent and a lipophilic co-enhancer; a percutaneous sorbefacient for electroporation; a penetration enhancer and aqueous adjuvant; a skin permeation enhancer comprising monoglyceride and ethyl palmitate; stinging cells from cnidaria, dinoflagellata and myxozoa; and/or the like. Formulations pertaining to skin permeability mechanisms are discussed in detail, for example, in U.S. Pat. Nos. 6,835,392, 6,721,595, 6,946,144, 6,267,984 and 6,923,976, each of which is specifically incorporated by reference into this section of the specification and all other sections of the specification. Also contemplated is microporation of skin through the use of tiny resistive elements to the skin followed by applying a patch containing adenoviral vectors as referenced by Bramson et al. (2003), and a method of increasing permeability of skin through cryogen spray cooling as referenced by Tuqan et al. (2005), and jet-induced skin puncture as referenced by Baxter et al. (2005), and heat treatment of the skin as referenced by Akomeah et al. (2004), and scraping of the skin to increase permeability.

In other embodiments, the patch is designed to use a low power electric current to transport the therapeutic agent through the skin. In other embodiments, the patch is designed for passive drug transport through the skin or mucosa. In other embodiments, the device is designed to utilize iontophoresis for delivery of the therapeutic agent.

The device may include a reservoir wherein the therapeutic agent is comprised in a solution or suspension between the backing layer and a membrane that controls the rate of delivery of the therapeutic agent. In other embodiments, the device includes a matrix comprising the therapeutic agent, wherein the therapeutic agent is in a solution or suspension dispersed within a collagen matrix, polymer, or cotton pad to allow for contact of the therapeutic agent with the skin. In some embodiments, an adhesive is applied to the outside edge of the delivery system to allow for adhesion to a surface of the subject.

In some embodiments, the device is composed of a substance that can dissolve on the surface of the subject following a period of time. For example, the device may be a file or skin that can be applied to the mucosal surface of the mouth, wherein the device dissolves in the mouth after a period of time. The therapeutic agent, in these embodiments, may be either applied to a single surface of the device (i.e., the surface in contact with the subject), or impregnated into the material that composes the device.

In some embodiments, the device is designed to incorporate more than one therapeutic agent. The device may comprise separate reservoirs for each therapeutic agent, or may contain multiple therapeutic agents in a single reservoir.

Further, the device may be designed to vary the rate of delivery of the therapeutic agent based on bodily changes in the subject, such as temperature or perspiration. For example, certain agents may be comprised in a membrane covering the therapeutic agent that respond to temperature changes and allow for varying levels of drug to pass through the membrane. In other embodiments, transdermal or transcutaneous delivery of the therapeutic agent can be varied by varying the temperature of the patch through incorporation of a temperature-control device into the device.

In preparing a transdermal patch according to the teachings of the specification and the knowledge of those skilled in the art, the bromide, an adhesive, and a permeation enhancer may be mixed together and dispensed onto a siliconized polyester release liner (Release Technologies, Inc., W. Chicago, Ill.). For example the transdermal patch formulation may consist of approximately 88% by composition of an acrylic copolymer adhesive, 2% of a nucleic acid expression construct, and 10% of a sorbitan monooleate permeation enhancer such as ARACEL 80® (ICI Americas, Wilmington, Del.). The mixture may then be dried and stored for treatment of a subject.

F. Combination Therapy

In addition to being used as a monotherapy, the compounds of the present disclosure may also find use in combination therapies. Effective combination therapy may be achieved with a single composition or pharmacological formulation that includes both agents, or with two distinct compositions or formulations, at the same time, wherein one composition includes a compound of this invention, and the other includes the second agent(s). Alternatively, the therapy may precede or follow the other agent treatment by intervals ranging from minutes to months.

Various combinations may be employed, such as where bromide or a salt thereof is "A" and "B" represents a secondary agent, non-limiting examples of which are described below:

| | | | | | | |
|---|---|---|---|---|---|---|
| A/B/A | B/A/B | B/B/A | A/A/B | A/B/B | B/A/A | A/B/B/B | B/A/B/B |
| B/B/B/A | B/B/A/B | | A/A/B/B | A/B/A/B | B/A/A/B | A/B/B/A | B/B/A/A |
| B/A/B/A | B/A/A/B | | A/A/A/B | B/A/A/A | A/B/A/A | A/A/B/A |

Administration of the agents of the present disclosure to a patient will follow general protocols for the administration of pharmaceuticals, taking into account the toxicity, if any, of the drug. It is expected that the treatment cycles would be repeated as necessary.

Secondary agents include peroxide, molecular oxygen, electron-accepting compound such as flavin adenine dinucleotide (FAD), hypobromous acid, nicotinamide adenine dinucelotide (NAD & NADH), nicotinamide adenine dinucelotide phosphate (NADP & NADPH), inosine monophosphate (IMP), guanosine monophosphate (GMP) or a combination thereof.

G. Examples

The following examples are included to demonstrate certain non-limiting aspects of the invention. It should be appreciated by those of skill in the art that the techniques disclosed in the examples which follow represent techniques discovered by the inventor to function well in the practice of the invention. However, those of skill in the art should, in light of the present disclosure, appreciate that many changes can be made in the specific embodiments which are disclosed and still obtain a like or similar result without departing from the spirit and scope of the invention.

Example 1—Materials & Methods

Chemicals.

Phloroglucinol, methimazole, potassium iodide and tetramethylbenzidine were >99% pure, and β-aminopropionitrile, putrescine and 3-1,2,4-aminotriazole were >98%, >97% and ~95% pure, respectively. All chemicals were obtained from Sigma Chemical Co.

Collagen IV NC1 Hexamer Isolation.

PFHR-9 cells were homogenized in 1% (w/v) deoxycholate with sonication, and the insoluble material isolated after centrifugation at 20,000 g for 15 min. The pellet was then extracted with 1 M NaCl (or 2 M urea in some experiments) plus 50 mM Tris-Cl pH 7.5 and 10 mM Tris-Cl pH 7.5 and was digested in 50 mM Tris-Cl pH 7.5, 5 mM CaCl, 5 mM benzamidine, 25 mM 6-aminocaproic acid, 0.4 mM phenylmethylsulfonyl fluoride (PMSF) and 0.1 mg ml−1 bacterial collagenase (Worthington). Collagenase-solubilized material was dialyzed against 50 mM Tris-Cl, pH 7.5. NC1 hexamers were purified using anion-exchange chromatography (DE52 Cellulose or Q Sepharose) followed by gel filtration chromatography.

In Vitro Basement Membrane Reactions.

PFHR-9 cells treated with potassium iodide (1-10 mM) to eliminate NC1 hexamer crosslinks were used for basement membrane isolation. To test halide dependency, the inventors established halide-free conditions by washing extensively (at least five times) with 10 mM sodium phosphate pH 7.4. To try to extract or inactivate endogenous basement membrane peroxidase activity, the inventors extracted the matrix preparation twice with 2M guanidine-Cl, 50 mM Tris-Cl pH 7.5 and 10 mM EDTA-Na pH 8 followed by extensive washing with 1×PBS. Basement membrane was resuspended in the desired buffer with or without cofactors and inhibitors to examine in vitro NC1 crosslinking under various conditions. Basement membranes were collagenase solubilized to delineate collagen IV NC1 sulfilimine crosslink formation with SDS-PAGE and Coomassie blue staining membrane was isolated, washed extensively and resuspended in 1×PBS. Azide (0-10 mM) and 1 mM H2O2 were added and allowed to react for 1 h at 37° C. The matrix was pelleted, washed extensively with 1×PBS and solubilized with 1×PBS plus 2% (w/v) SDS. Solubilized proteins were reacted with 100 μM Tris[(1-benzyl-1H-1,2,3-triazol-4-yl) methyl]amine (Anaspec), 1 mM Tris(2-carboxyethyl)phosphine hydrochloride (ThermoFisher Pierce), 1 mM cupric sulfate and 100 μM biotin alkyne (PEG4 carboxamidepropargyl biotin; Life Technologies) for 1 h at 37° C. Click chemistry reactions were quenched with 1 mM 3'-azido-3'-deoxythymidine (Sigma). For avidin-HRP detection, samples were electrophoresed under reducing conditions, transferred to nitrocellulose membranes and probed with streptavidin-HRP according to manufacturer instructions (ThermoFisher Pierce). To isolate biotinylated proteins, the inventors precipitated click reaction products with two volumes of cold acetone to remove reactants, washed them with 70% (v/v) acetone and then resolubilized them in 1×PBS plus 2% SDS. Biotinylated proteins were captured with streptavidin-agarose beads (GE Life Sciences) and released with boiling for 15 min in SDS-PAGE sample buffer containing 50 mM dithiothreitol.

Purification of Recombinant Human Peroxidasin.

HEK293 cells stably transfected with the human peroxidasin coding sequence27 were grown to confluency, and the medium was changed to serum-free DMEM/F12 plus 5 µM hematin plus 5 mM sodium butyrate. After 48-60 h, medium was harvested, protease inhibitors were added (0.5 mM PMSF, 1 mg ml−1 leupeptin, 1 µg ml−1 pepstatin and 10 mM EDTA-Na), and proteins were precipitated with 40% (w/v) ammonium sulfate (226 g/l). Precipitated protein was resuspended at 1/50 of the original medium volume in 0.3 M sucrose, 0.1 M NaCl and 20 mM Tris-Cl pH 8.5; dialyzed against the same buffer; and chromatographed on a Mono-Q anion exchange column (GE Life Sciences). Enzymatically active fractions were pooled, precipitated to 1/500 the original medium volume of 50 mM NaCl, 10 mM sodium phosphate pH 7.4 and 3 mM hexadecyltrimethylammonium chloride and were dialyzed against the same buffer. The dialyzed protein was further purified using ultracentrifugation on a 5-20% (w/v) sucrose gradient. Active fractions were pooled and concentrated to a final concentration of 0.25-0.5 mg ml−1 of purified human peroxidasin.

HEK293 Cell Overlay on Uncrosslinked Collagen IV Networks.

PFHR-9 cells were grown in the presence of 50 µM phloroglucinol to produce noncrosslinked collagen IV. Basement membrane was isolated on plates using a modification of a previously published protocol 46. To inactivate endogenous crosslinking activity, the basement membrane was treated with 4 M guanidine-Cl plus 50 mM Tris-Cl pH 7.5 for 15 min and then washed 5 times with 1×PBS. In the first set of experiments, HEK cells stably transfected with human peroxidasin were compared to wild-type HEK293 cells. In follow-up experiments, HEK293T cells were transiently transfected with human peroxidasin coding sequence27, mouse myeloperoxidase cDNA (Origene), mouse lactoperoxidase cDNA (Origene) or empty vector (pCDNA-V5-His-TOPO without insert) using Lipofectamine LTX per manufacturer's instructions (Life Technologies). In both sets of experiments, cells were plated on PFHR-9 basement membrane in the presence of 5 µM hematin and 5 mM sodium butyrate. Plates were incubated for 24-48 h, and collagen IV was analyzed for NC1 crosslink formation.

Preparation of HOCl and HOBr Solutions.

Standard techniques were used to pre-pare HOCl and HOBr.

Measurement of Hypohalous Acid Production by Peroxidases.

Hypohalous acids were trapped as stable taurine haloamines, which oxidize tetramethylbenzidine to yield a colorimetric measure of hypohalous acid concentration and production (Dypbukt et al., 2005).

Drosophila Biochemistry and Genetics.

Drosophila collagen IV NC1 hexamer was essentially purified as described for PFHR-9 cells.

Statistical Analysis.

Statistical analysis was conducted using GraphPad Prism version 5.04 (GraphPad Software). Comparisons between two groups used two-tailed unpaired Student's t-tests, whereas multiple group comparisons were conducted using analysis of variance followed by Tukey's post hoc comparisons between specific groups.

Example 2—Results

Figure 1B:
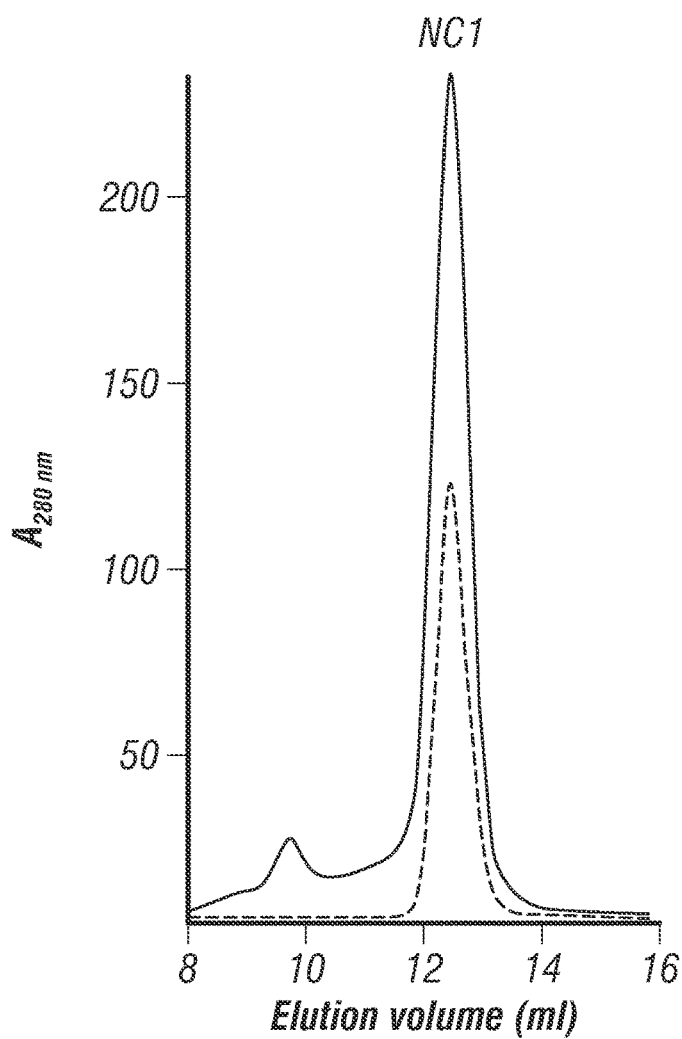
Figure 1C:
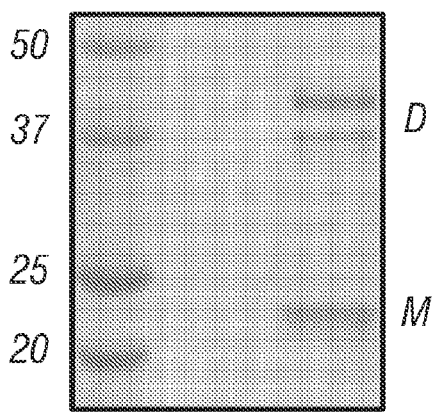
Figure 1D:
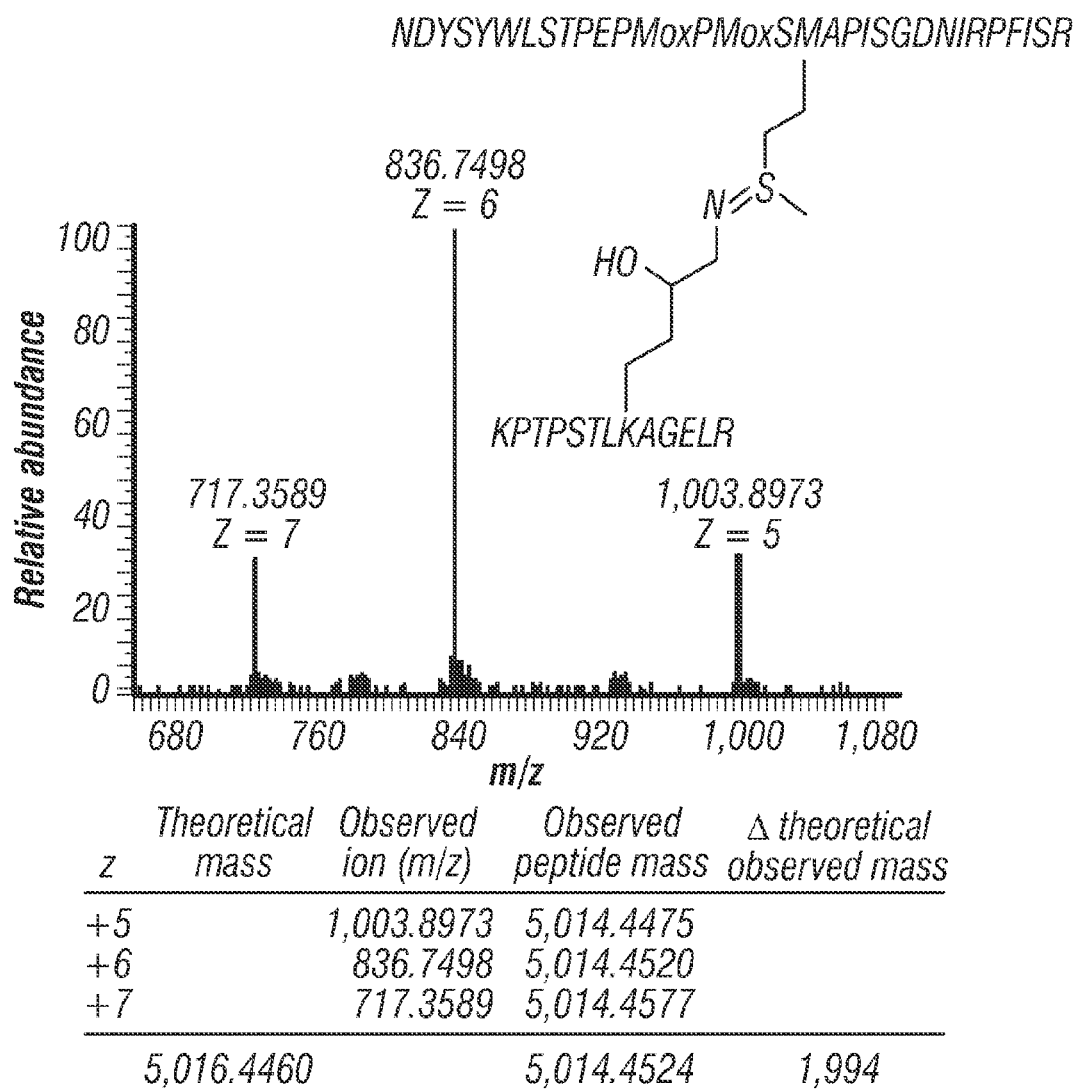

A model to study collagen TV sulfilimine bond formation. To study sulfilimine bond formation, the inventors used the PFHR-9 mouse endodermal cell line as an experimental system, as it produces biochemically tractable quantities of collagen IV (Fessler & Fessler, 1982). When grown past confluency, PFHR-9 cells progressively accumulated basement membrane, which the inventors isolated to purify collagen IV NC1 hexamers after collagenase digestion. SDS dissociation of NC1 hexamers and gel electrophoresis revealed both crosslinked NC1 dimeric and uncrosslinked monomeric subunits (FIGS. 1A-C). MS provided chemical evidence for a sulfilimine bond joining Met93 and hydroxylysine 211 (Hyl211) in adjacent protomers (FIG. 1D). The inventors initially focused on known oxidative matrix-associated enzymes as possible mediators of sulfilimine bond formation in collagen IV. When small-molecule inhibitors were used during cellular deposition of basement membrane, structurally distinct peroxidase inhibitors including phloroglucinol (half-maximum inhibitory concentration ($IC_{50}$)=0.5 µM) (Nelson et al., 1994), methimazole ($IC_{50}$=0.8 µM for thyroid peroxidase, 3 mM inhibits myeloperoxidase by 70%)[8,9] and 3-aminotriazole (near-complete inhibition of thyroid peroxidase at 2 mM and of myeloperoxidase at 10 mM) (Alexander, 1959; Weiss et al., 1982) universally prevented formation of collagen IV crosslinks. The inventors initially examined iodide as a possible peroxidase substrate to form hypoiodous acid as a reactive intermediate (more details in Discussion). Unexpectedly, potassium iodide inhibited collagen IV crosslink formation, and therefore the inventors used it as an inhibitor in subsequent experiments (FIG. 2A). Lysyl oxidase (β-aminopropionitrile; $IC_{50}$=3-8 µM) (Tang et al., 1983) and transglutaminase inhibitors (putrescine; Km 0.026-0.847 mM) (Candi et al., 1995) had no effect despite the use of concentrations exceeding published inhibitory constants (FIG. 2A). Peroxidase inhibitors did not perturb collagen IV assembly in this system, as NC1 hexamers formed quantitatively in the absence of sulfilimine crosslinks (data not shown). Peroxidase inhibitors also did not break crosslinks after formation but specifically prevented bond formation (FIG. 2B). These findings suggest that a peroxidase, embedded within basement membrane, forms sulfilimine bonds in collagen IV. If so, an isolated basement membrane preparation should recapitulate this biochemical event in vitro with the addition of hydrogen peroxide ($H_2O_2$), a required substrate for peroxidases. PFHR-9 cells were grown in the presence of a peroxidase inhibitor (10 mM potassium iodide) to deposit a collagen IV network devoid of sulfilimine crosslinks.

A basement membrane preparation was isolated and incubated without inhibitor in the absence or presence of $H_2O_2$. Sulfilimine bonds formed rapidly when peroxidase inhibitors were removed only in the presence of $H_2O_2$, pointing to a peroxidase residing within the basement membrane (FIG. 2C and data not shown). Alternatively, $H_2O_2$ may chemically form sulfilimine crosslinks in collagen IV. To investigate this possibility, the inventors extracted PFHR-9 basement membrane with 2M guanidine to inactivate and/or extract the basement membrane peroxidase without affecting collagen IV. Indeed, guanidine pretreatment of the basement membrane eliminated crosslinking activity even in the presence of $H_2O_2$, consistent with the loss of an enzymatic activity rather than direct chemical oxidation by $H_2O_2$ (data not shown).

Peroxidasin Catalyzes Formation of Sulfilimine Bonds.

To rapidly identify candidates, the inventors developed a new approach to covalently label and capture basement membranebound peroxidases. Inorganic azide (N3) is a known suicide inhibitor of peroxidases. In the presence of azide and $H_2O_2$, peroxidases generate azidyl radicals that covalently attach to the peroxidase heme moiety to form an organic azide (R-N3) and eliminate enzymatic activity (Ki=1.47 mM, kinact=0.69 min$^{-1}$ for horseradish peroxidase (HRP))[14]. PFHR-9 basement membrane was isolated and treated with azide and $H_2O_2$ to form an organic azide conjugate with matrix peroxidases. After basement membrane proteins were solubilized with SDS, azide-peroxidase conjugates were then biotinylated using alkyne biotin to react with the organic azide in a copper-catalyzed 'click' chemistry reaction[15]. Electrophoresed proteins were blotted with streptavidin-HRP to detect biotinylated proteins, revealing a single streptavidin-reactive band at about 160-200 kDa with reactivity increasing in a dose-dependent manner with azide concentration (data not shown). Streptavidin agarose affinity chromatography was used to purify the azide-labeled peroxidase, revealing a single predominant band on Coomassie bluestained protein gels at the same molecular weight as the band observed with streptavidin blotting (data not shown). The stained protein band was excised and digested with trypsin. MS of the resulting peptides revealed peroxidasin as an azide-labeled peroxidase residing within PFHR-9 basement membrane (data not shown).

Recognizing the azide labeling technique as a screening tool with limitations, the inventors next tested whether the identified candidate, peroxidasin, is truly capable of and responsible for the formation of sulfilimine crosslinks in collagen IV. To determine whether peroxidasin is biochemically able to catalyze sulfilimine bond formation, the inventors heterologously expressed and purified human peroxidasin (data not shown). When reacted with purified NC1 hexamer, which was prepared without crosslinks, peroxidasin led to robust formation of crosslinked dimeric subunits at low enzyme/substrate ratios (<1:30) only in the presence of $H_2O_2$ (FIG. 3A). MS of the peroxidasin-reacted NC1 hexamer confirmed sulfilimine bond formation at levels near that of the native PFHR-9 hexamer (data not shown). To determine whether the ability to catalyze bond formation is a universal property of animal peroxidasins, the inventors reacted *Drosophila* peroxidasin with uncrosslinked collagen IV and found similar crosslinking activity (data not shown). Taken together, peroxidasin crosslinks collagen IV NC1 hexamer in vitro.

Peroxidasin Forms Sulfilimine Bonds Via Hypohalous Acids.

Figure 3D:
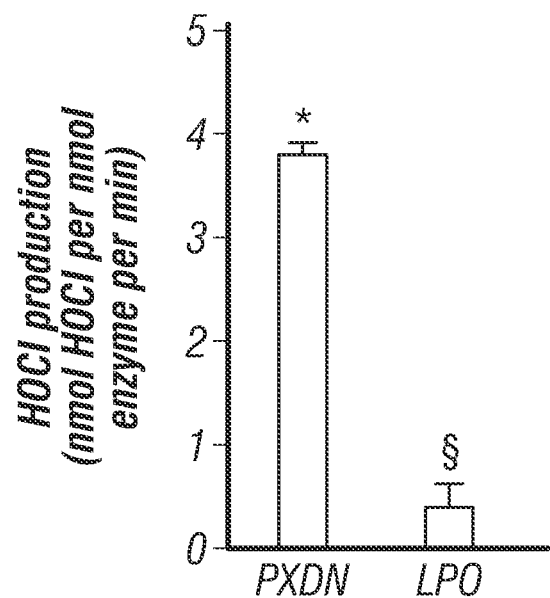
Figure 3E:
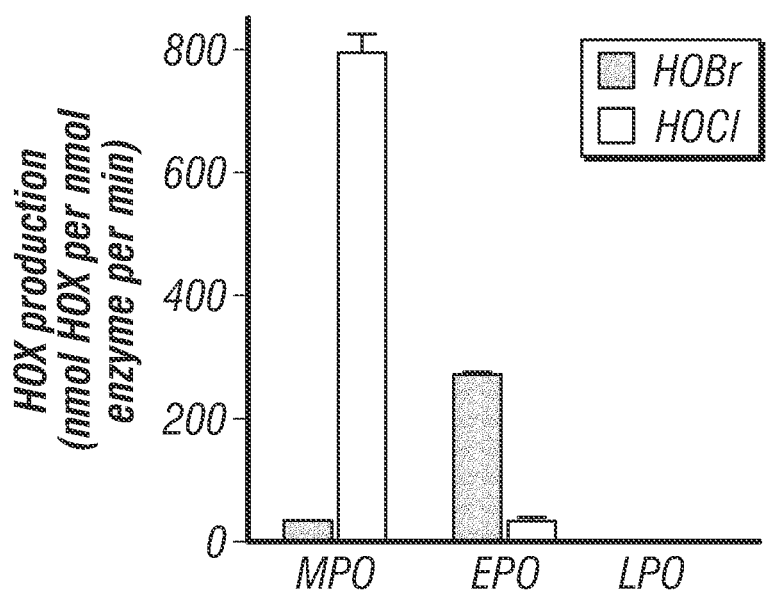

Animal heme peroxidases, such as peroxidasin, myeloperoxidase, eosinophil peroxidase and lactoperoxidase, catalyze oxidative reactions using distinct halogenation and peroxidase cycles (Obinger, 2006). Both begin with hydrogen peroxide oxidation of the prosthetic heme iron to form an intermediate denoted compound I (Obinger, 2006). Compound I may oxidize halides into their respective hypohalous acids (or related oxidants in equilibrium), which may directly or indirectly halogenate susceptible moieties. Alternatively, compound I undergoes sequential reduction to form single electron-free radicals of energetically favorable substrates in the peroxidase cycle. Both pathways eventually regenerate reduced, native enzyme (Obinger, 2006). To determine whether peroxidasin forms sulfilimine bonds using a halogenation cycle, the inventors first tested whether peroxidasin crosslinks collagen IV in the absence of halides. When $H_2O_2$ was added to uncrosslinked basement membrane without halides, very few crosslinked collagen IV dimeric subunits formed until halide (Cl— or Br—) concentrations approached 100 mM, suggesting the involvement of a peroxidase halogenation cycle (FIG. 3B). Peroxidasin is known to iodinate proteins, but little is known about its ability to oxidize other halides such as bromide and chloride. Using taurine to trap hypohalous acids as stable taurine haloamines (Weiss et al., 1982; DypBukt, 2005), peroxidasin formed hypobromous and hypochlorous acid at modest rates with a preference for bromide (FIGS. 3C-D). Consistent with previous work, myeloperoxidase preferentially formed hypochlorous acid, eosinophil peroxidase primarily yielded hypobromous acid, and lactoperoxidase formed neither hypohalous acid (FIG. 3E) (Obinger, 2006). Taken together, peroxidasin produces hypohalous acids and requires halides (Cl or Br) to form sulfilimine bonds, suggesting a link between the two activities.

If peroxidasin uses hypohalous acids as intermediates to form sulfilimine bonds, these intermediates should recapitulate the reaction when directly added to purified, uncrosslinked collagen IV NC1 hexamer. Indeed, reacting collagen IV with hypochlorous or hypobromous acid yielded crosslinked dimeric subunits (FIG. 4A and data not shown). Alternatively, other peroxidasesis provided to form reactive hypohalous acids. Myeloperoxidase and eosinophil peroxidase formed sulfilimine crosslinks in collagen IV (FIGS. 4B-C), whereas lactoperoxidase poorly catalyzed crosslink formation as it does not efficiently form hypochlorous or hypobromous acid (FIGS. 3D and 4D) (Obinger, 2006).

Peroxidasin Crosslinks Collagen IV for Tissue Integrity.

Figure 5A:
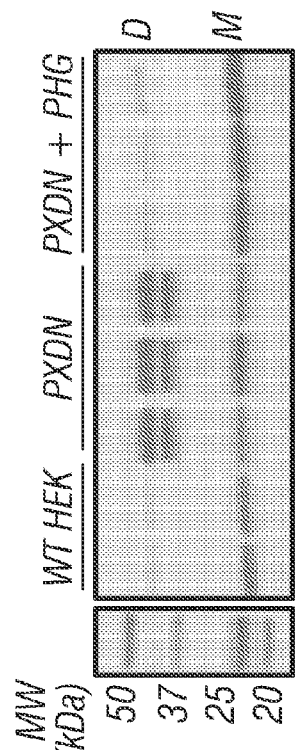
FIGS. 5A-D—Peroxidasin uniquely crosslinks native collagen IV networks.
Figure 5B:
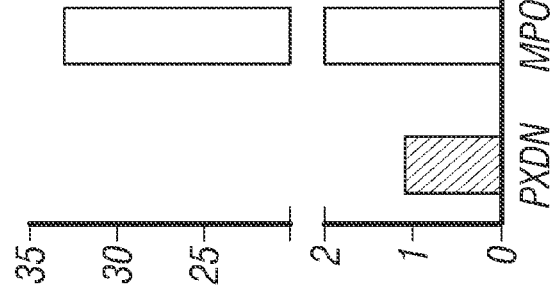
Figure 5C:
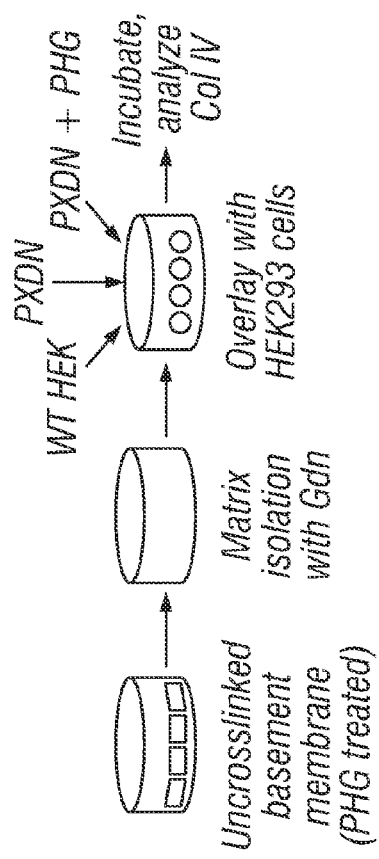
Figure 5D:
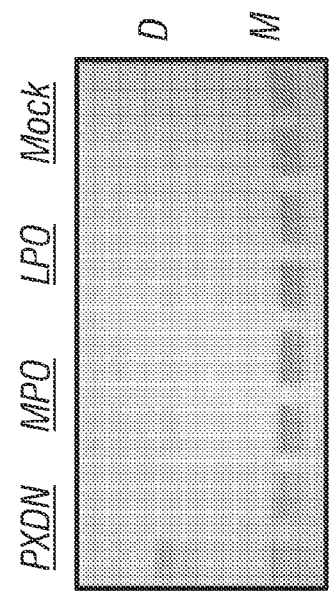

Though peroxidasin forms sulfilimine bonds in vitro, the inventors tested whether peroxidasin catalyzes the formation of the sulfilimine bond within native insoluble collagen IV networks. HEK293 cells expressing human peroxidasin were plated on top of a PFHR-9-deposited basement membrane, which was produced in the presence of phloroglucinol to render a collagen IV network without sulfilimine crosslinks (FIG. 5A). Only overlaid cells expressing human peroxidasin formed dimeric crosslinked NC1 subunits, whereas wild-type HEK293 cells or peroxidasin-transfected cells in the continued presence of phloroglucinol failed to crosslink collagen IV (FIG. 5B). The inventors hypothesized that peroxidasin, as a resident basement membrane protein (Nelson et al., 1994), uniquely crosslinks collagen IV networks, whereas other peroxidases, though capable of bond formation in solution, will not form crosslinks within basement membranes. To test this hypothesis, HEK293 cells were plated on uncrosslinked PFHR-9 basement membrane and transiently transfected with peroxidasin, myeloperoxidase and lactoperoxidase cDNA or empty expression vector to determine whether peroxidasin specifically crosslinks collagen IV. Only peroxidasin formed sulfilimine bonds in collagen IV, even though myeloperoxidase enzymatic activity was at least 30-fold greater than peroxidasin (FIGS. 5C-D). These data suggest that only peroxidasin, embedded within basement membranes, generates hypohalous acid in close proximity to its collagen IV substrate. Comparatively greater but spatially indiscriminate generation of hypohalous acid by myeloperoxidase artificially crosslinks soluble collagen IV NC1 hexamer but fails to crosslink insoluble, basement membrane collagen IV.

To further substantiate that peroxidasin functions to form sulfilimine bonds in collagen IV and to delineate the role of this function in basement membrane homeostasis, the inventors turned to the *Drosophila* genetic model system, where peroxidasin was first discovered (Nelson et al., 1994). Using MS of purified *Drosophila* collagen IV NC1 hexamer, the inventors first experimentally determined that the collagen IV sulfilimine bond is present in *Drosophila* larvae as sequence conservation of Met93 and Lys211 may not necessarily translate into a crosslink bridging these residues (data not shown) (Vanacore et al., 2009). With biochemical characterization of the collagen IV sulfilimine bond in hand, the inventors examined basement membrane architecture in *Drosophila* larvae homozygous for a severely, hypomorphic peroxidasin (Pxn) allele (Pxnf07229/f07229; denoted as Pxn−/−) before their demise as third instar larvae. With the collagen IV GFP protein trap line (vikingG454), the inventors visualized collagen IV networks within basement membranes of the longitudinal and circumferential midgut visceral muscles (Morin et al., 2001). These networks appeared severely distorted and extensively torn in Pxn−/− mutants when compared with heterozygous Pxn+/− and wild-type Pxn+/+ larvae (FIG. 6A). Collagenase solubilization of larval basement membrane revealed that Pxn−/− collagen IV NC1 content was about 20% that of the wild-type (Pxn+/+), based on immunoreactivity (FIG. 6B). Furthermore, Pxn−/− mutants showed a shift toward uncrosslinked monomer subunits, with immunoreactivity rising to 42% of total band density compared to <9% in Pxn+/− larvae (FIG. 6B). Thus, peroxidasin forms sulfilimine bonds that crosslink collagen IV to reinforce basement membranes and maintain tissue integrity.

Bromide is Required for PXDN Formation of Sulfilimine Bonds.

Cultured murine PFHR9 cells synthesize collagen IV networks that contain sulfilimine crosslinks due to the activity of PXDN. The NC1 domain of collagen IV provided a metric for assessing the reaction, in the solubilization of NC1 protein from matrix with collagenase enzyme and subsequent SDS-PAGE resolution of crosslinked dimeric from uncrosslinked monomeric NC1 domains. In culture, with bromide and chloride enhancing sulfilimine crosslinking. Within purified matrix, 10 µM Br⁻ and 100 mM Cl⁻ both permitted enzymatic crosslinking. Upon examination, stock chloride salts were found to contain significant amounts of bromide, questioning whether chloride is indeed activating. Chloride salts were purified and re-assayed as a halide source for PXDN-crosslinking. Pure Cl⁻ was insufficient for the reaction, with crosslinking being recovered by the supplementation with low micromolar concentrations of bromide.

Biosynthetic Activity of HOBr.

Hypobromous acid (HOBr) catalyzes the formation of collagen IV sulfilimine bonds, as an intermediate in the mechanism of the PXDN crosslinking reaction. The enzymatic halogenation cycle is initiated by oxidation of heme moiety within PXDN, experimentally achieved hydrogen peroxide, followed by the oxidation of ionic bromide resulting in localized production of HOBr within matrices. The efficiency of HOBr as a reagent was compared to other hypohalous acids, during a 5' reaction with uncrosslinked hexamers containing 5 µM NC1 domains. HOBr was superior to all other examined reagents at forming collagen IV sulfilimine bonds in vitro. To confirm that oxidized bromide was sufficient as a halide reagent, HOBr was synthesized in the absence of other halides, and the pure HOBr solution retaining full catalytic ability.

Example 3—Discussion

In this work, the inventors demonstrate that peroxidasin catalyzes sulfilimine bond formation in collagen IV, the first known bond of its kind in a biomolecule (Vanacore et al., 2009). Peroxidasin was initially discovered as a basement membrane constituent in *Drosophila*, but herein the inventors establish its first bona fide function: namely, crosslinking collagen IV (Nelson et al., 1994). Both the *Drosophila* mutant described in this work and *Caenorhabditis elegans* mutants of peroxidasin show defects in basement membrane integrity similar to the effects of mutations in collagen IV itself (Gotenstein et al., 2010; Gupta et al., 1997). These data provide a molecular mechanism for this phenotypic similarity. Loss of peroxidasin function leads to fewer collagen IV crosslinks, destabilizes collagen IV and reduces its content within basement membranes. Mutations in human PXDN were recently discovered in a subset of individuals with inherited anterior segment dysgenesis and cataracts. Accounting for two peroxidasin homologs in humans (Cheng et al., 2008), the inventors hypothesize that partial loss of peroxidasin activity compromises the collagen IV network of anterior eye basement membranes and again recapitulates an ocular phenotype commonly observed in patients with partial loss of function in collagen IV (Coupry et al., 2010; Favor et al., 2007; Gould et al., 2007; Labelle-Dumais et al., 2011; Van Agtmael et al., 2005). Taken together, peroxidasin, collagen IV and the sulfilimine crosslink form an important triad for basement membrane function and tissue biogenesis alongside laminin, nidogen and proteoglycan.

Though this work identifies what the inventors believe to be the first function of peroxidasin, the formation of sulfilimine crosslinks in collagen IV may not be its only function. Peroxidasin is upregulated in response to transforming growth factor-β stimulation of fibroblasts and in renal interstitial fibrosis (Peterfi et al., 2009). Collagen IV, a constituent primarily of basement membranes, is minimally present in fibroblast-generated extracellular matrix3. Thus, peroxidasin may form sulfilimine crosslinks in other matrix proteins or execute noncatalytic functions involving protein-protein interactions with cell-surface receptors and matrix proteins.

Peroxidasin generates hypohalous acids and requires halides to form sulfilimine crosslinks, whereas hypohalous acids produce sulfilimine bonds when directly applied to collagen IV NC1 hexamer. Similarly, hypohalous acids, including HOBr and HOCl, form an intramolecular sulfilimine bond to convert methionine into dehydromethionine (Beal et al., 2009; Peskin et al., 2009). The inventors hypothesize that peroxidasin, embedded within basement membranes near its collagen IV substrate, locally generates hypohalous acids, which form an intermolecular sulfilimine bond across two collagen IV protomers in a reaction mechanism akin to the formation of dehydromethionine. Specifically, HOBr and HOCl react with the sulfur of Met93 to form a halosulfonium cation intermediate, which is then trapped by the Hyl[211] amine to form a sulfilimine bond (data not shown)[30]. Close proximity of the amine to the thioether creates a high effective amine concentration to prevent the halosulfonium cation from reacting with solvent water in a side reaction producing methionine sulfoxide. In collagen IV, the close apposition of Met93 and Hyl[211] on separate NC1 trimers provides the required approximation of nitrogen and sulfur atoms to yield a sulfilimine bond bridging the NC1 trimer-trimer interface (Peskin et al., 2009).

Although the parallel between the chemical synthesis and enzymatic catalysis of sulfilimine bonds suggests a mechanistic link, these data point to some differences. Iodine ($I_2$) or hypoiodous acid (HOI) also efficiently converts methionine to dehydromethionine (Beal et al., 2009; Peskin et al., 2009; Lavine, 1947), yet iodide paradoxically inhibits crosslink formation in collagen IV. Many possible mechanisms could explain this inhibition, including I⁻ quenching of reactive hypohalous acid intermediates (Huwiler et al., 1985), competition between I⁻ and $H_2O_2$ preventing compound I formation[23] or complex halide interactions at the peroxidasin catalytic site (Blair-Johnson et al., 2001; Andrews and Krinsky, 1982; Taurog and Dorris, 1992).

Hypohalous acids typically conjure images of microbial destruction and unintended toxicity, but this work points to an unexpected, anabolic role for these highly reactive species. Peroxidasin is optimally suited to productively use hypohalous acids because its noncatalytic leucine-repeat-rich and immunoglobulin protein interaction domains presumably place peroxidasin in close proximity to its collagen IV substrate so that relatively modest amounts of hypohalous acids form sulfilimine crosslinks without pathologic 'collateral damage'. The use of hypohalous acids as anabolic intermediates presumably depends on coupling peroxidasin oxidant generation with sulfilimine crosslink formation and possibly on local antioxidant mechanisms. Excessive peroxidasin activity either due to overexpression or increased $H_2O_2$ substrate availability may uncouple hypohalous acid generation from sulfilimine bond formation, allowing free hypohalous acid oxidants to accumulate and produce intended or unintended toxicity. Indeed, mosquito gut peroxidasin is upregulated after bacterial infection, and its knockdown reduces bacterial clearance and host survival (Garver et al., 2008). Invertebrate peroxidasin may generate antimicrobial hypohalous acids as a primitive form of innate immunity analogous to vertebrate myeloperoxidase and eosinophil peroxidase (Zamocky et al., 2008).

Oxidative stress and reactive oxygen species have a central role in the pathogenesis of atherosclerosis, diabetes mellitusassociated complications and hypertensive vascular disease, which are the leading causes of morbidity and mortality in developed nations (Brownlee, 2001; Touyz and Briones, 2011; Yokoyama, 2004). Human peroxidasin, also known as vascular peroxidase 1 (VPO1), is upregulated in cell culture models of hypertension and atherosclerosis and promotes smooth muscle proliferation and fibrosis, but the mechanistic connection between peroxidasin and downstream pathologic events is unknown (Peterfi et al., 2009; Bai et al., 2011; Shi et al., 2011; Brandes et al., 2011). As peroxidasin consumes $H_2O_2$ produced by cell-surface NADPH oxidases (NOX), enhanced NOX-generated $H_2O_2$ in pathologic states may promote peroxidasin-mediated matrix crosslinking and stabilization, eventually leading to tissue fibrosis (Cheng et al., 2008: Brandes et al., 2011). Alternatively, 'uncoupled' peroxidasin activity may lead to hypohalous acid accumulation, promoting tissue injury. Indeed, myeloperoxidase has garnered considerable attention for hypochlorous acid-mediated oxidative modifications involved in the development of vascular inflammatory disorders such as atherosclerosis (Lau and Baldus, 2006). But unlike myeloperoxidase, whose deleterious actions require targeting to vessel wall, peroxidasin is omnipresent at the site of pathology within vascular basement membranes and therefore primed to generate deleterious oxidants and participate in disease pathogenesis (Cheng et al., 2008; Brandes et al., 2011; Lau and Baldus, 2006). Collectively, these results establish that peroxidasin forms collagen IV sulfilimine crosslinks, a post-translational modification critical for basement membrane integrity and tissue biogenesis, and draw attention to peroxidasin as an oxidant generator embedded within basement membranes readily capable of contributing to disease pathogenesis.

Example 4—Results

Bromine is ubiquitously and consistently present in animals with no known essential function (Kirk, 1991). To date, the only identified biologic role for bromide (Br—) is as a substrate for eosinophil peroxidase (EPO) (Weiss et al., 1986), however the absence of EPO had few adverse effects (Denzler et al., 2001). Recently, Peroxidasin (PXDN), a basement membrane heme peroxidase, was also found to oxidize Cl— and Br— to their respective hypohalous acids (HOCl and HOBr) (Li et al., 2012; Bhave et al., 2012). The production of hypohalous acids by peroxidasin was responsible for covalently cross-linking the collagen IV network in vitro and in vivo via the formation of the sulfilimine bond (S=N) (Bhave et al., 2012). Thus far unique in biology, the S=N bond forms between juxtaposed lysine (or hydroxylysine) and methionine residues in the non-collagenous 1 (NC1) domains of collagen IV molecules (Vanacore et al., 2009) (FIG. 7A). Mutants of peroxidasin in either *Drosophila* (Bhave et al., 2012) or *C. elegans* (Gotenstein et al., 2010) show gross basement membrane and developmental defects, demonstrating that S=N formation by peroxidasin within collagen IV networks is essential.

The abundance of S=N crosslink within the collagen IV network (assessed by the amount of dimeric NC1 after collagense digest and gel electrophoresis) of high mechanical stress tissue such as glomerular basement membrane (GBM) and placental basement membrane (PBM) is most closely recapitulated by the in vitro application of HOBr, not HOCl (Langevald et al., 1988; FIG. 7A). Yet given the >1000 fold physiologic excess of Cl to Br, the operant in vivo halide target of peroxidasin remained undefined for S=N bond formation. Herein, the inventors provide multifaceted evidence supporting bromine's selective use by peroxidasin, a chemical basis for its non-equivalence with Cl in biology, and ultimately its requirement for development in vivo.

Stoichiometry of S=N Crosslinks within Dimeric NC1 Domains.

Figure 7C:
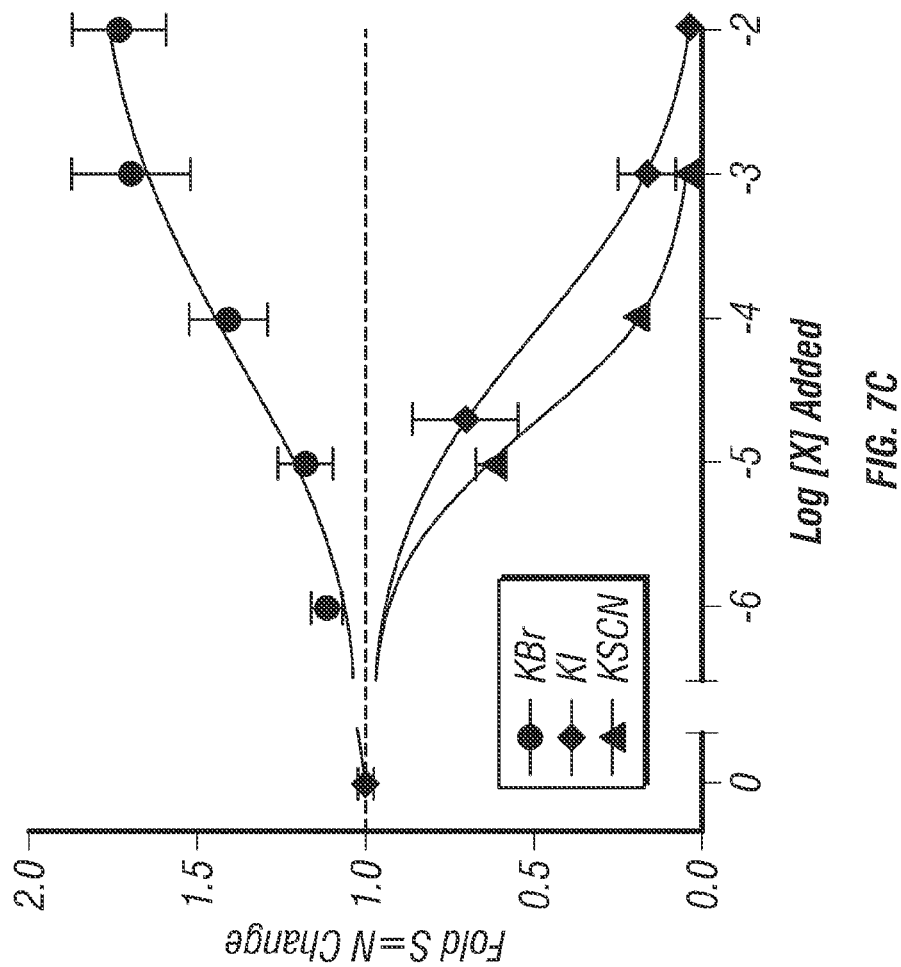
Figure 7B:
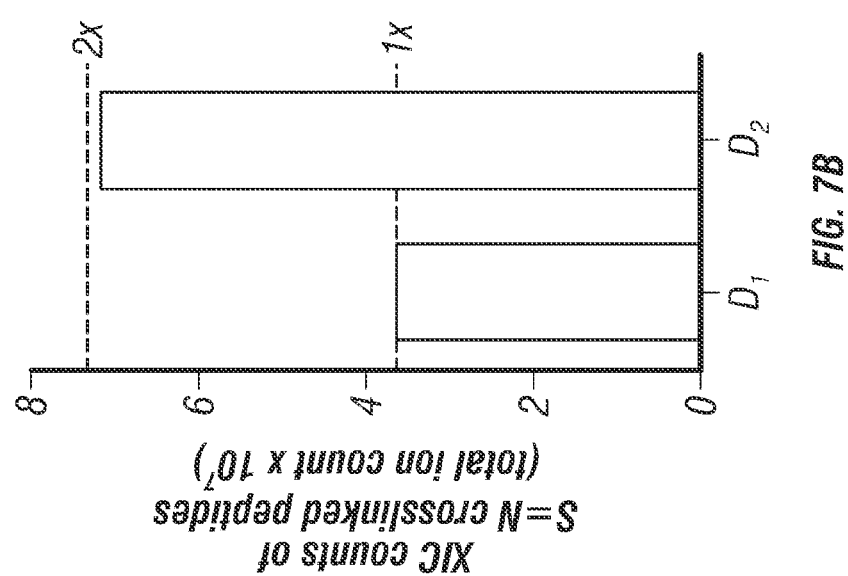

The interface of C-termini of two trimeric collagen IV protomers forms a hexamer of NC1 domains. Each NC1: NC1 interaction contains two pairs of opposed Met and Hyl, enabling one or two potential S=N crosslinks per dimer. NC1 hexamers, solubilized from the collagenous matrix by enzymatic digestion with bacterial collagenase, analyzed by SDS-PAGE reveal the relative amounts of sulfilimine-containing NC1 dimers versus uncrosslinked monomeric domains (FIG. 7A). Dimeric NC1 domain exhibits two distinct bands (D1 and D2) with different electrophoretic mobility. In a manner analogous to circular vs. linear DNA, the inventors expected that a doubly S=N crosslinked dimer would form a large cyclic structure and have higher electrophoretic mobility when compared to a mostly linear singly crosslinked dimer of the same sequence (Aaij et al., 1972). Because a difference in S=N content would be expected in this scenario, they purified NC1 hexamer from murine PFHR-9 basement membrane cell-culture model, isolated D1 and D2 by electrophoresis, performed an in-gel trypsin digest, and analyzed the abundance of S=N crosslink peptides by liquid chromatography—mass spectrometry (LC-MS). D2, the band with higher electrophoretic mobility, was found to have 1.96-times more S=N containing peptides than D1 (FIG. 7B). The presence of two additional Methionines in the peptide accounted for a total of four additional oxidation events, which the inventors observed and quantified by total ion counts in an extracted ion chromatogram (XIC) (data not shown). Comparative analysis of the NC1 domain by electrophoresis therefore allows the determination of the extent of S=N crosslinking in a sample based on the [(2 S=N) D2:(1 S=N) D1:(0 S=N) Monomer] band ratios.

Bromide Enhances Peroxidasin-Based Sulfilimine Bond Formation.

The enzymatic mechanism of peroxidasin requires a halide cofactor to for the S=N bond (Bhave et al., 2012). The inventors therefore screened halide and thiocyanate ("pseudohalide") ions in cell culture for their effect on sulfilimine bond formation. Expectedly, postassium iodide (KI) inhibited S=N formation (IC50=84 µM 95% CI (30-241 µM)), as did potassium thiocyanate (KSCN) (IC50=17 µM 95% CI (3-24 µM]). Contrasting with these effects, exogenous potassium bromide (KBr) enhanced S=N formation (EC50=75 µM 95% CI (55-212 µM)) (FIG. 7C; data not shown). The examination of additional halides in culture was precluded by high concentrations of chloride in media and cytotoxicity of fluoride.

Figure 8A:
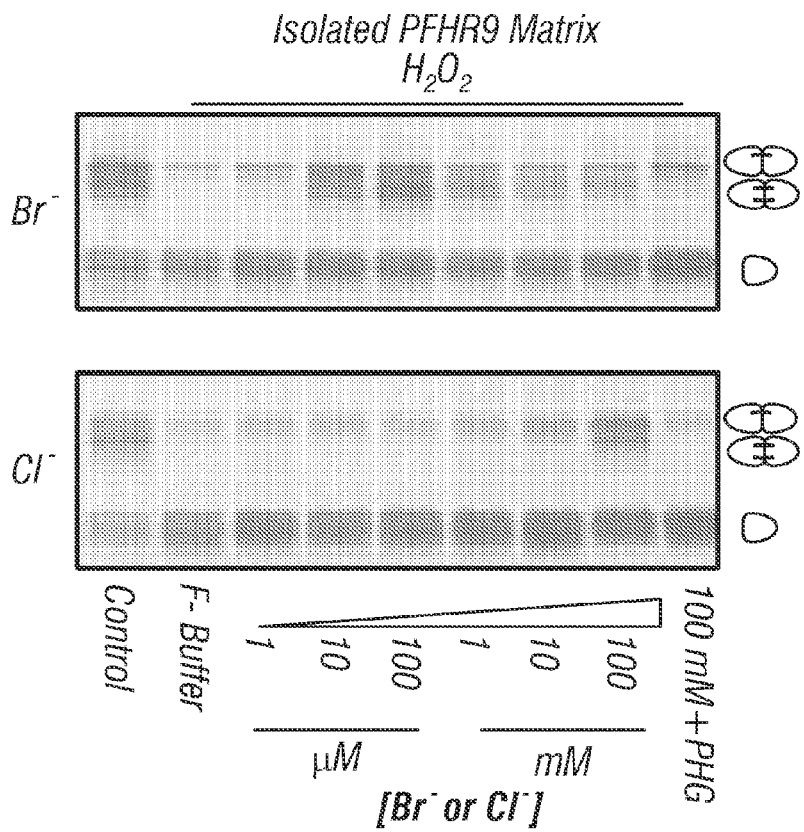
FIGS. 8A-D. Bromide is Required for Sulfilimine Bond Formation by Peroxidasin.

Prior demonstration of peroxidasin crosslinking in matrix required 100 mM of either bromide or chloride; within the physiologic range of chloride yet more than 1000-fold above human serum bromide concentrations when reacted in a low ionic strength buffer (Bhave et al., 2012). In order to more accurately mimic physiologic conditions, the inventors reexamined peroxidasin driven crosslinking in an isolated collagenous matrix reaction in 100 mM potassium fluoride (KF) as an ionic control. Fluoride proved inert toward S=N bond formation in this system (FIG. 8A). Under these conditions, chloride, bromide, and iodide were tested for S=N bond formation. Bromide robustly catalyzed bond formation at 10 µM while chloride remained inactive until 100 mM (FIG. 8A). Iodide, over a range of 1 nM-100 µM, demonstrated no S=N formation (data not shown). These data indicate that serum bromide and chloride concentrations both appear to be sufficient for peroxidasin catalyzed formation of sulfilimine bonds.

Br-Free Chloride does not Sufficiently Support Bond Formation.

Figure 8B:
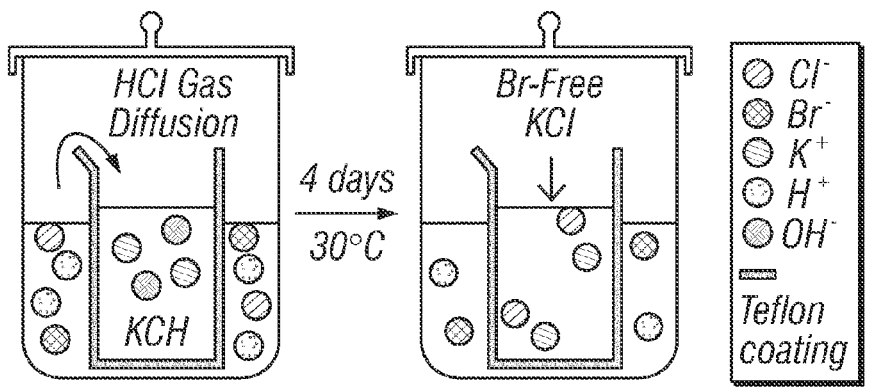
Figure 8C:
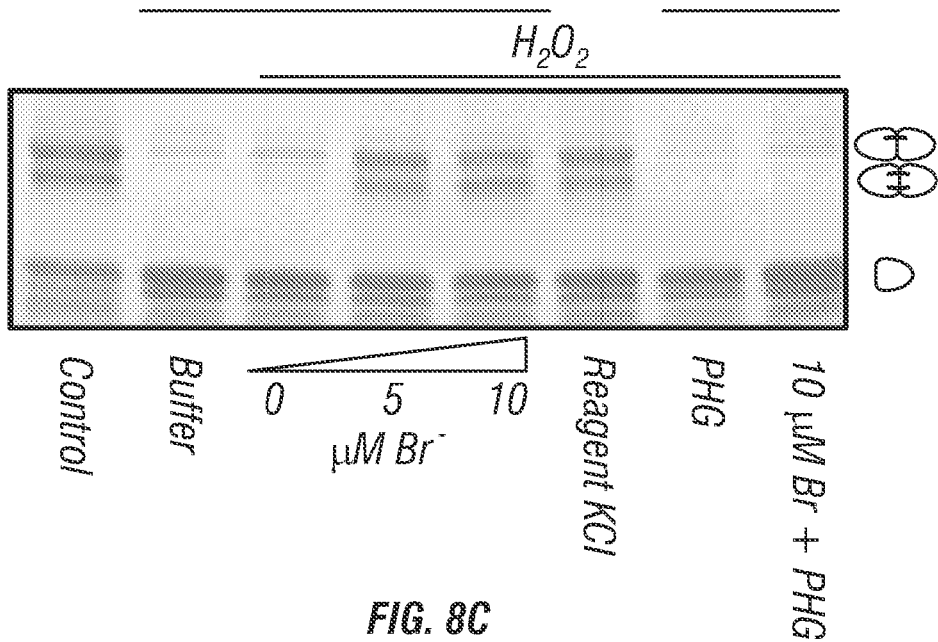

Given the remaining ambiguity in the halide cofactor preference of peroxidasin, the inventors sought clarity regarding the absolute composition of their reagents. They turned to Inductively Coupled Plasma Mass Spectrometry (ICP-MS) for assessing the purity of chloride salts with respect to the presence of any contaminating bromide because of a part-per-billion detection limit for Br. Indeed, Br— was found to be present at 5.91 µM Br— per 100 mM KCl and 2.35 µM per 100 mM NaCl (data not shown). The inventors thus asked whether the crosslinking observed in experiments containing 100 mM Cl— was due to minor amounts of contaminating bromide. To address the issue with confidence, they purified Br-Free NaCl and KCl by exploiting HCl's preferential volatilization over HBr, and subsequent neutralization with concentrated NaOH or KOH solution (FIG. 8B and (Joy et al., 1973)). After recrystallization, the purified Cl— salts contained Br— below the detection limit of the ICP-MS method (<0.91 ppb) (data not shown). This confirms purification of a chloride source with <11.4 nM Br—per 100 mM KCl or 100 mM NaCl. This Br-free chloride was then assayed within the isolated PFHR-9 matrix reaction. Br-free KCl did not support dimer formation to levels comparable with untreated controls (FIG. 8C), and similar results were also obtained using purified NaCl (data not shown). Crosslink formation was restored upon addition of 5 µM Br—, demonstrating that bromide is responsible for enzymatic bond formation in matrix.

Bromide is the Selective Enzymatic Substrate of Peroxidasin.

Figure 8D:
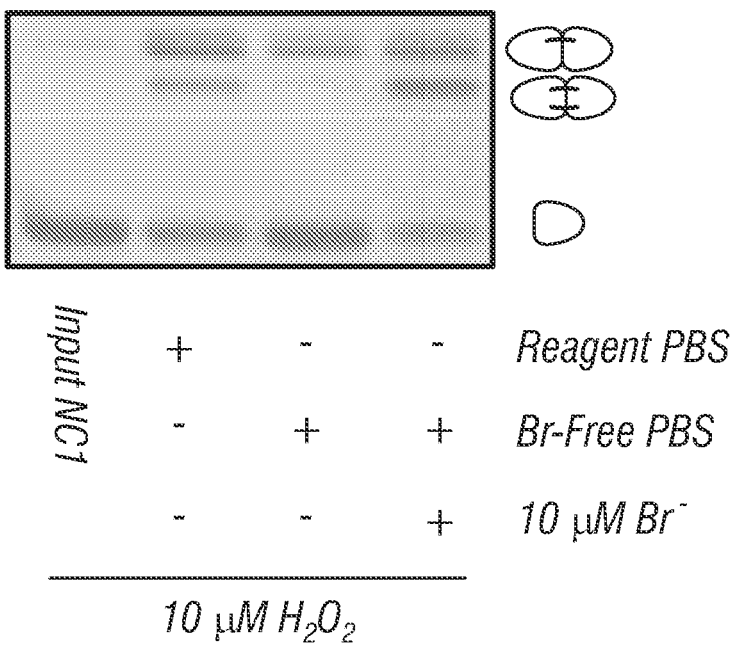
Figure 8D:
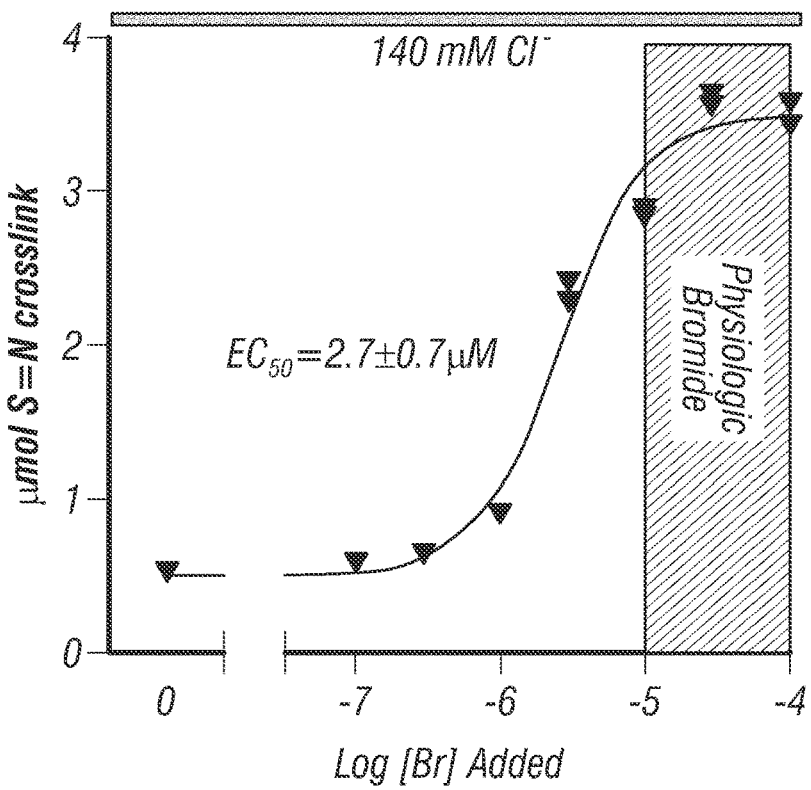

With a clean chloride source in hand, the inventors next wanted to characterize the behavior of purified recombinant human peroxidasin and uncrosslinked NC1 in physiologic levels of chloride. Reagent grade phosphate buffered saline (PBS) was compared to a Br-Free PBS made from Br-Free NaCl and KCl. Similar to the matrix results, the Br addition recued the degree of S=N bond formation observed in reagent-grade PBS (FIG. 8D). The non-zero value of baseline S=N bond formation in Br-Free conditions should be noted as an indication of HOCl production by peroxidasin, consistant with previous finding that HOCl is produced by peroxidasin and forms marginal amounts of S=N crosslink (Bhave et al., 2012). To better understand the selectivity of peroxidasin's halide oxidation profile, the inventors titrated Br— into Br-Free PBS. Using S=N bond formation as a functional endpoint for HOBr production by peroxidasin, they determined the EC50 for bromide in this system to be 2.7 µM (95% CI 2.0-3.5 µM) in the presence of 140 mM Cl— (FIG. 8D). These data indicate a >50,000-fold selectivity preference for Br— over Cl— by a peroxidasin-collagen IV pure system.

Mechanism of Br-Catalyzed Sulfilimine Bond Formation in Collagen IV.

Figure 9A:
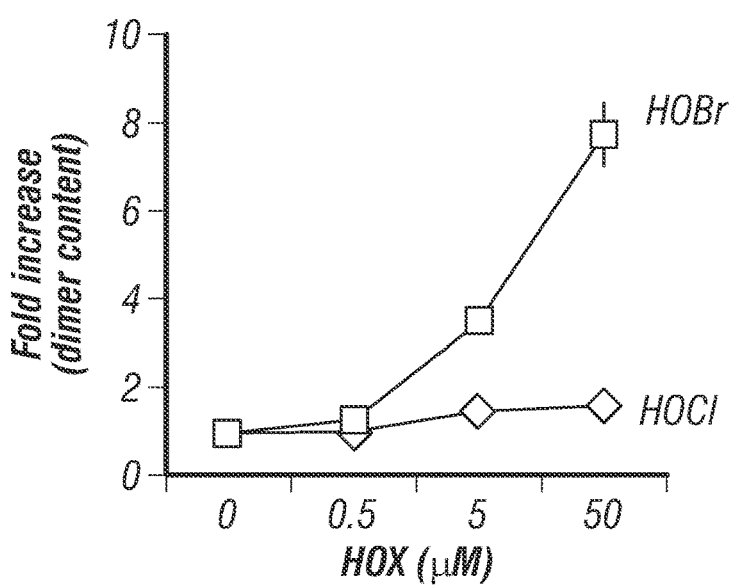
FIGS. 9A-D. Chemical mechanism of sulfilimine formation within the NC1 hexamer.
Figure 9B:
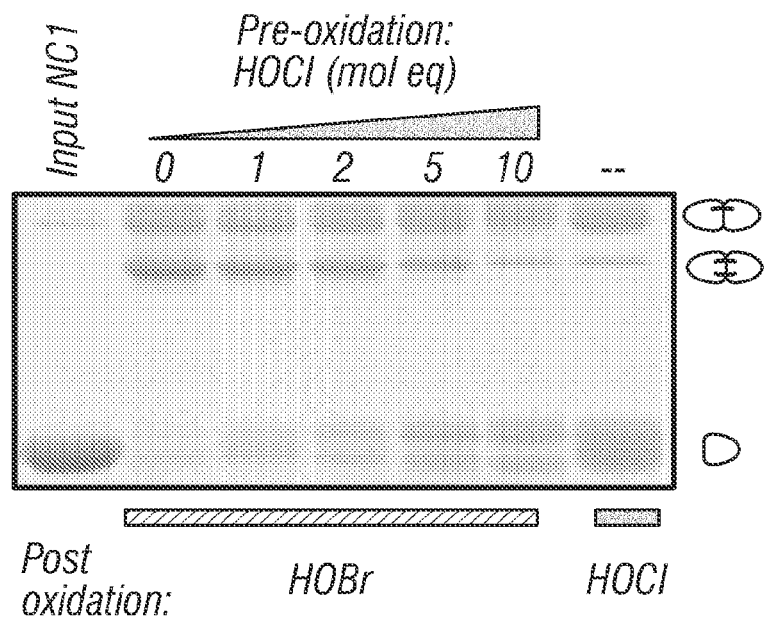
Figure 9C:
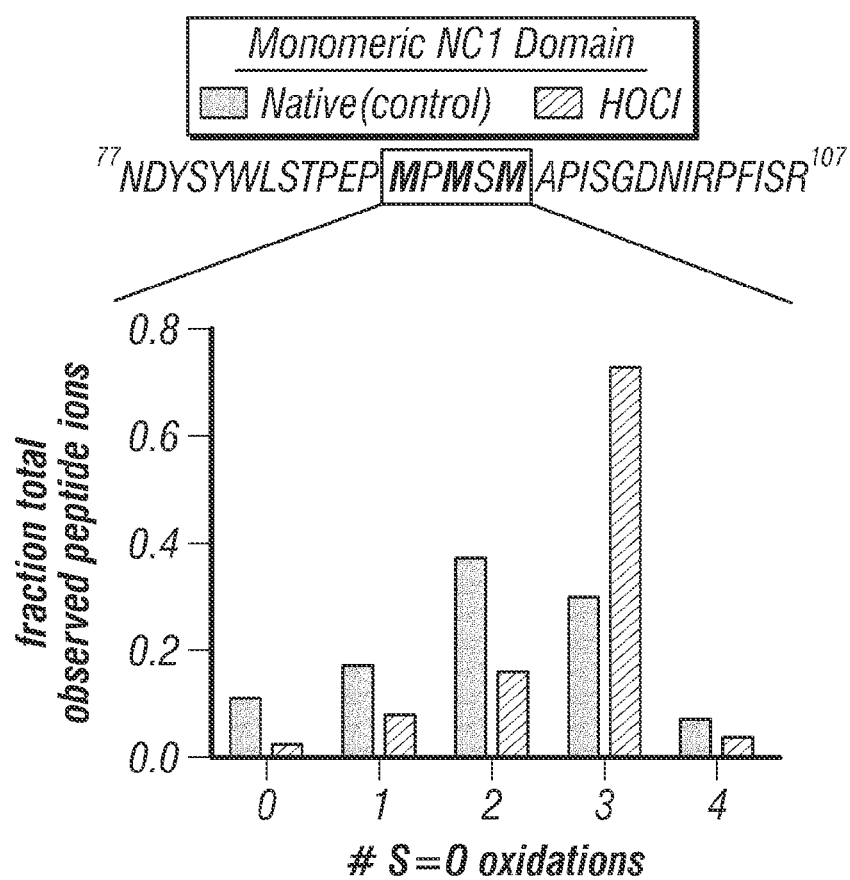

The observation that HOCl and HOBr were both chemically able to form S=N crosslink, albeit with grossly different efficacies, prompted the investigation of what features govern this difference between the two halides from the perspective of the NC1 domain. Structural similarity between collagen IV sulfilimine bonds and dehydromethionine has been noted (Vanacore et al., 2009), and direct comparison of HOCl and HOBr oxidation of methionine to dehydromethionine found HOBr to be approximately twice as effective as HOCl at forming a sulfilimine bond. Both hypohalous acids were also found to produce methionine sulfoxide (S=O) as the alternative product of oxidation (Peskin et al., 2009). The inventors therefore tested the molar efficiency of oxidation of purified uncrosslinked NC1 hexamer with HOCl and HOBr (FIG. 9A). HOBr efficiently formed dimers even at parity with NC1 concentrations, while 50 µM HOCl was required to drive S=N bond formation. Because surface exposed methionines are preferred oxidation targets of both HOCl and HOBr (Pattison et al., 2004), the inventors hypothesized that the formation of methionine sulfoxide would occur if S=N bond formation did not. To the best of the inventors' knowledge, there have been no reports of sulfilimine formation from sulfoxides, making S=O formation a 'dead-end' for cross-linking. To test this, they pretreated uncrosslinked NC1 hexamer with varying concentrations of HOCl, then treated with HOBr. The expected degree of S=N bond formation decreased with pretreatment of increasing levels of HOCl, until it resembles HOCl treatment alone (FIG. 9B). These data suggest that HOCl and HOBr both target a finite number of residues capable of S=N bond formation, and that HOCl creates an uncrosslinkable product despite not forming an S=N bond. As an independent approach to testing the dead-end sulfoxide hypothesis, the inventors pretreated NC1 hexamer with escalating levels of H2O2, a reagent known to generate methionine sulfoxides (Liang et al., 2012). Pretreatment with H2O2 created a dose-dependent decrease in the crosslinking efficacy of HOBr (data not shown). They next decided to directly visualize the peptide containing Met93, the S donor of the S=N bond, within the residual monomeric NC1 fraction after HOCl oxidation and compare its oxidation status to untreated NC1 hexamer. The HOCl oxidized samples were prepared with a 10-fold mol excess of HOCl:NC1. Both samples were subjected to SDS-PAGE, bands were isolated, and an in gel tryptic digest performed. The tryptic fragment containing Met$^{93}$ also contains two additional methionines, requiring overall, and site specific oxidation analysis. Ion counts for the peptides were again quantified by XIC, and revealed a shift in the total oxidation state for the HOCl-treated monomer peptides toward 3 $^{16}$O additions (FIG. 9C and data not shown). The inventors then performed a collision-induced-dissociation (CID) MS3 (MS/MS/MS) fragmentation analysis to determine which of the three methionine residues was oxidized. Peptides containing MetO$^{93}$ were more abundant in the residual monomer from HOCl treatment, notably when MetO$^{93}$ was the either the sole, or part of multiple oxidation events (data not shown).

Figure 9D:
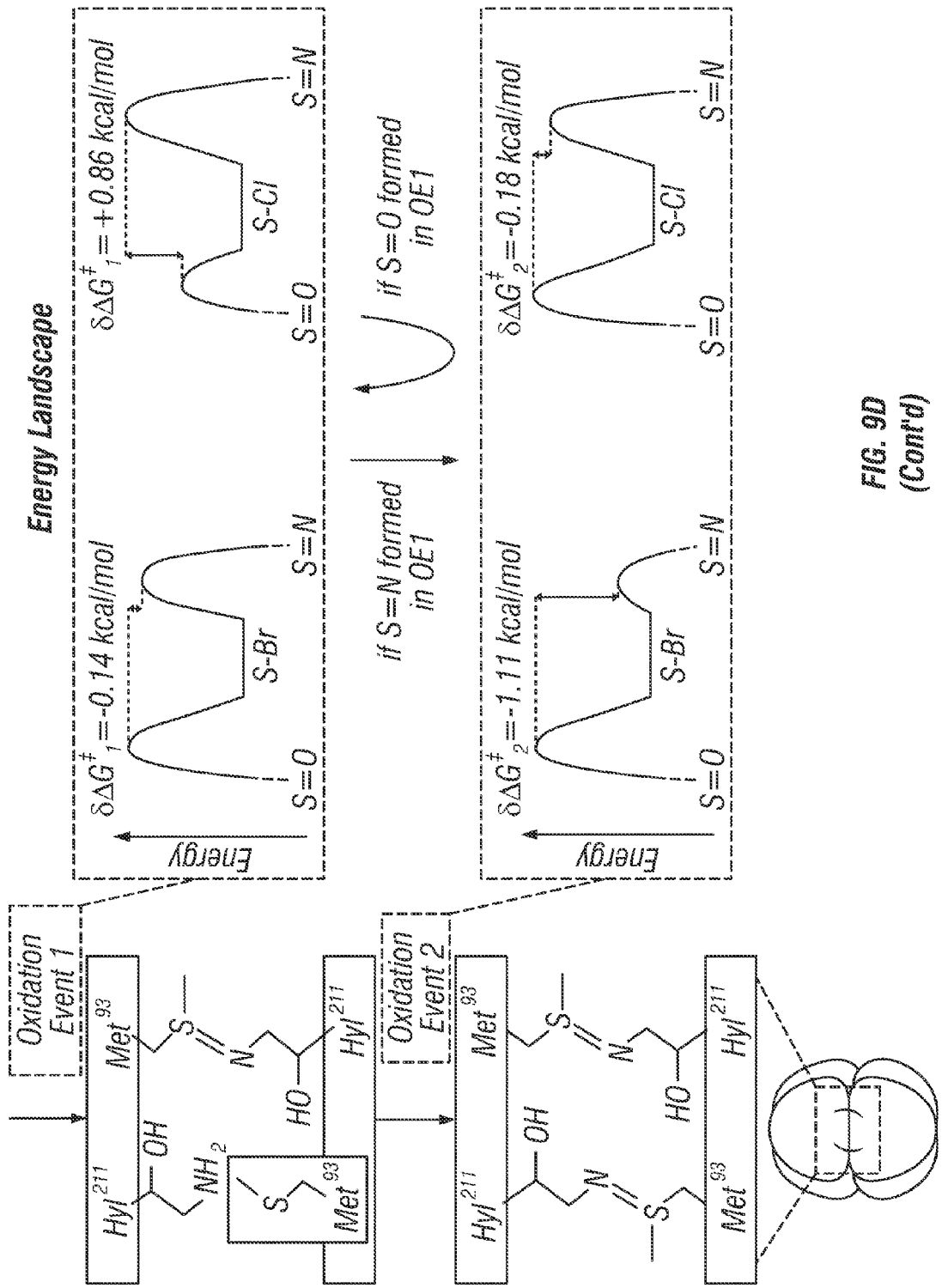

The inventors therefore created a model of sulfilimine bond formation based on the dichotomous choice for Met$^{93}$ once oxidized by HOX (X=Cl— or Br—) to form a halosulfonium intermediate (HSI) to either 1) react with H2O and form sulfoxide or 2) react with the amine moiety of Hyl$^{211}$ and form the sulfilimine crosslink. The experiment that they then envisioned involved complete stoichiometric oxidation of each of the six Met$^{93}$ within the NC1 hexamer, enabling the product comparison of S=O and S=N content based on analysis of D2 (2 S=N):D1 (1 S=N and 1 S=O): Monomer (2 S=O). Comparison of the product ratios enables the calculation of the relative free energy difference of the transition states for the competing S=O and S=N reaction pathways. To this end, the inventors performed the oxidation of the NC1 domain with both HOCl and HOBr and analyzed the band distribution according to this dichotomous model (FIG. 9D). The results revealed that oxidation event 1 (OE1) and OE2 were not independent events, but rather sequentially linked. For both OE1 and OE2, the S—Br intermediate displayed a lower barrier to S=N bond formation than the comparable S—Cl HSI (FIG. 9D). While absolute rate constants for kS=O or kS=N cannot be determined with this methodology, comparison of the proportion of S=N products for both S—Cl and S—Br HSI reveals a relative concentration increase of the amine (from Hly211) from OE1 to OE2 of 34.9%±4.1%, which is consistant with a conformational change within the NC1 dimer unit upon formation of an S=N bond. During OE1, the S—Cl HSI formed an S=N bond in 19% of total Met93 Met$^{93}$ oxidized, compared with the S—Br HSI for which S=N bond formation occurred in 56.1% of Met93 oxidations. These S—N bond formation percentages closely approximate what is known for the 5-membered ring cyclization involved in the oxidation of Methionine to form dehydromethionine (Peskin et al., 2009), suggesting a local effective molarity of >1000M for the amine functionality from the perspective of the HSI (Illuminati et al., 1981) in OE1.

These observations also demonstrate that S—Br and S—Cl have different selectivity for nucleophiles. At the observed concentration ratios of (H2O)⊗NH2-Hyl211) in the NC1 hexamer, there was at least a 1 kcal/mol preference for the amine by S—Br compared to S—Cl. The pronounced polar solvent reaction rate enhancement with primary amines for S—Cl vs. S—Br in organic and alcoholic solvents observed previously supports a more polar transition states for the S—Cl HSI (Ciuffarin et al., 1970). Coupled with the analysis both experimentally and in silico that S—Cl species participate in charge-controlled reactions which preferentially select for 'harder' nucleophiles (such as H2O compared to NH2-R) and have highly polar transition states, while S—Br species participate in orbital-controlled reactions which select for 'softer' nucleophiles (in this system can be understood to mean NH2-R), provides a chemical basis for the observed pattern of reactivity in the NC1 domain (Chmutova et al., 1999; Klopman, 1968; Pearson, 1968). Taken together, the enthalpic and intrinsic reactivity bias toward S=N bond formation by S—Br intermediates shows the chemical non-equivalence of chloride and bromide within the NC1 hexamer and highlights a degree of NC1 substrate preference for bromide.

Bromide Uniquely Catalyzes Sulfilimine Bond Formation In Vivo.

Figure 10A:
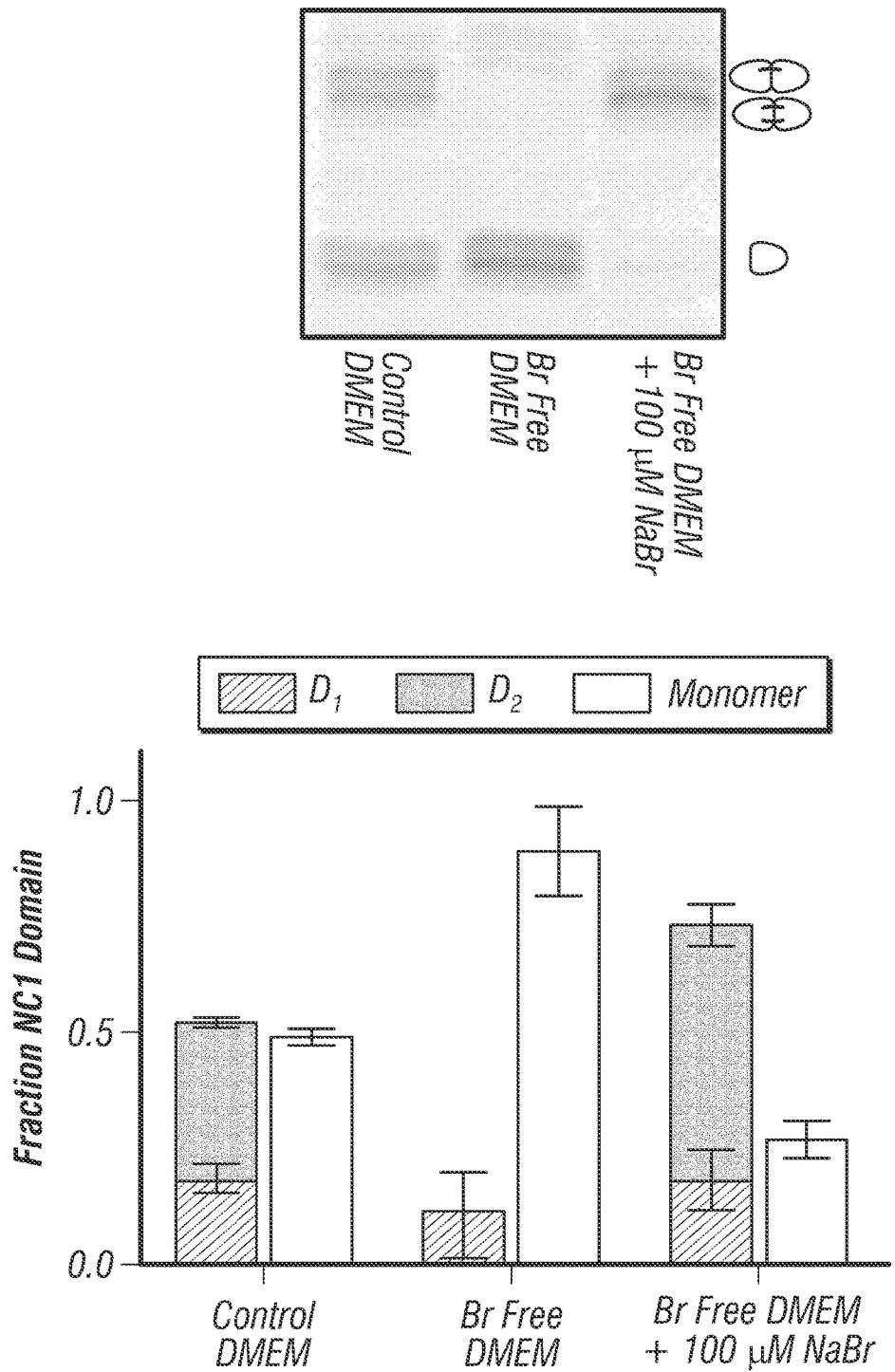
FIGS. 10A-C. Bromide is required for S=N bond formation in mammalian culture.

Based on their understanding of the enzymatic and substrate preference for bromide with respect to physiological levels of S=N bond formation, the inventors decided to test whether bromide was in fact responsible for crosslinking in vivo. Dulbecco's Modified Eagle Medium (DMEM) with 5% Fetal Bovine Serum used to culture PFHR-9 murine cell creates a collagenous matrix with levels of S=N crosslink similar to GBM or PBM (FIG. 7A). Bromine was systematically eliminated from DMEM by making the media from individual components without chloride counter ions, and using Br-Free chloride as the only halide source. Hank's buffered saline solution (HBSS) was made similarly to enable the dialysis of FBS to remove contaminating Br— (data not shown). Neutron Activation Analysis (NAA) was used to verify the elimination of Br— from the inventors' complete Br-Free DMEM+5% dialyzed FBS, which showed a final Br concentration of below the NAA detection limit in Br-free media and 12.5 µM in the control DMEM (data not shown). In Br-Free and Br-added culture conditions, there was no observable difference in cell proliferation, viability, or collagen IV synthesis. However, Br-Free DMEM did not support S=N bond formation in the collagen IV matrix, while the addition of 100 µM Br⁻ rescued physiologic levels of crosslinking (FIG. 10A).

Figure 10B:
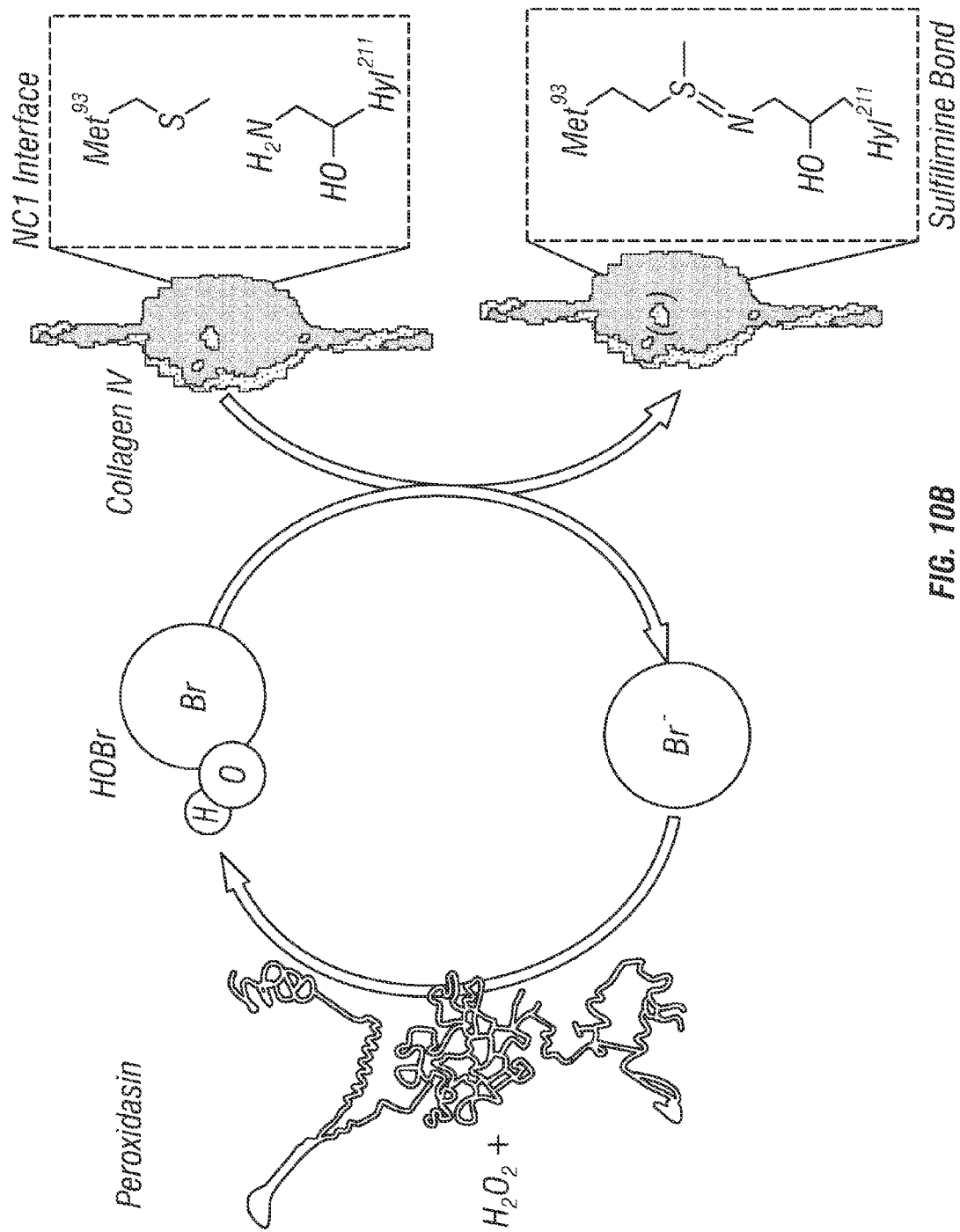
Figure 10C:
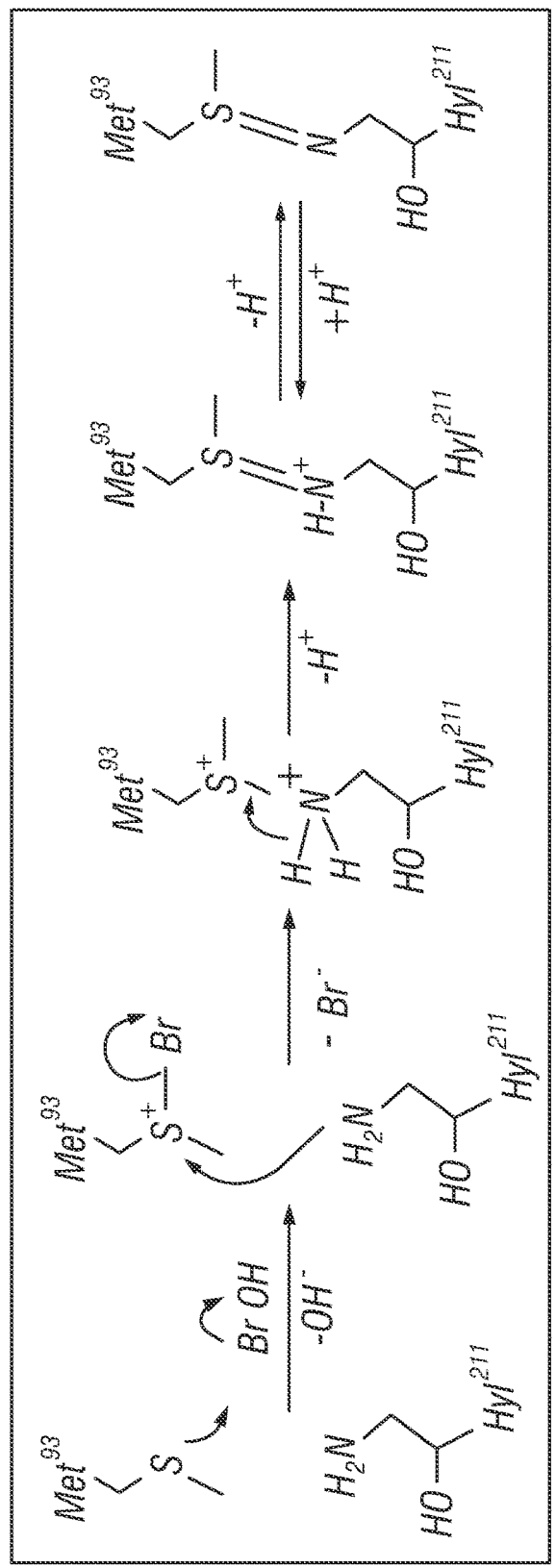

The data presented thus far enables the formulation of a working hypothesis for the function of bromine within basement membranes whereby Br⁻ catalyzes the formation of the S=N within collagen IV (FIG. 10B). The selective oxidation of Br⁻ by peroxidasin to form HOBr, which has been chemically shown to form the S=N bond via a reaction consistent with the formation of an S—Br intermediate on Met93. The S—Br intermediate would then react with the amine moiety of Hyl$^{211}$ to regenerate Br⁻ (FIG. 10C).

Bromide is Required for Development in *Drosophila*.

In order to test their working hypothesis of bromide function in an animal model, the inventors turned to *Drosophila*. In the lab environment, *Drosophila* are reared on a standard Grape juice-Agar plate supplemented with a yeast paste for additional nutrition. These components were subjected to NAA which showed a total bromine content of 15.0 µM for the standard diet. To eliminate Br— from these food components, the inventors grew yeast under Br-Free conditions in an adapted Yeast Nitrogen Base media, re-purified the agar substitute Phytagel, and recapitulated the main nutrients available in grape juice while excluding any halide source other than Br-Free chloride. After preparation, the inventors tested food components and found Br levels below the sensitivity limit afforded by NAA demonstrating that bromine has been removed from the system. The inventors therefore tested the relative growth rates of wild-type *Drosophila melanogaster* w1118 on a standard diet compared to Br-Free and 100 µM Br-Added experimental diets. The Br-added experimental diet supported the same median time to the developmental landmarks of pupariation (6 days) and eclosion (10 days) as standard diet, while the Br-free diet caused a significant delay (p<0.001) to both pupariation (8 days) and eclosion (14 days) (data not shown). While this data supports the idea that dietary Bromide is required for normal growth rates, there is a sizable bromide contribution of 55 µM within the eggs of other fly species (Piedade- Guerreiro et al., 1987) which would potentially mask the observable phenotypes of bromide deficiency. To overcome this issue, the inventors depleted adult *Drosophila* of bromide prior to egg deposition by raising the total salt concentration in all portions of the diet to 80 mM Br-Free NaCl. The increased salt concentrations shortens the half-life Cl— in the fly to ~5 hours (Fairbanks and Burch, 1970), thereby enabling the depletion of bromide by increasing total halide flux in an analogous way to high-salt bromide wash-out in mammals (Pavelka et al., 2005). After 72 hours of high-salt treatment of adult in either a Br-Free high salt cohort, or Br-Added (100 μM NaBr) high salt cohort, the deposited eggs were counted and followed through larval development maintaining respective high-salt conditions. Following maternal depletion of bromide, virtually all Br-free larvae died before they could complete development, while the addition of bromide rescued development (FIG. 11A). The peroxidasin hypomorphic allele PxnF07229 was also tested for its developmental sensitivity, and bromide was unable to promote developmental progression. These data show that bromide is essential for the completion of development in *Drosophila*.

During the course of the survival experiment depicted in FIG. 11A, the inventors observed the formation of grossly visible melanotic masses in 8 of 10 Br-Free larvae which survived to 3rd instar. Similar melanotic lesions were observed in PxnF07229 larvae (FIG. 11B). To confirm this observation, another cohort of Br-Free depleted larvae were allowed to develop and then dissected. The melanotic masses were always found in the midgut, though the location of the localized lesion varied anteriorly from the gastric cucum to the midgut-hindgut junction posteriorly. A characteristic lesion from Br-Free Larvae at the midgut constriction is shown in FIG. 11C, along with the identical region from a Br-Added larvae of the same developmental stage. Despite the smaller size of the PxnF07229 larvae, a lesion at the midgut-hindgut junction is also shown, displaying a grossly similar phenotype. It was previously shown that PxnF07229 larvae had disrupted collagen IV networks which were directly visualized in the gastric cecum, a portion of the midgut, coupled with an apparent elimination of S=N crosslink (Bhave et al., 2012). The apparent phenocopy of Br deficiency and peroxidasin hypomorphic mutants suggests an integrated in vivo pathway for bromide and peroxidasin, which are both essential for normal development.

Figure 12B:
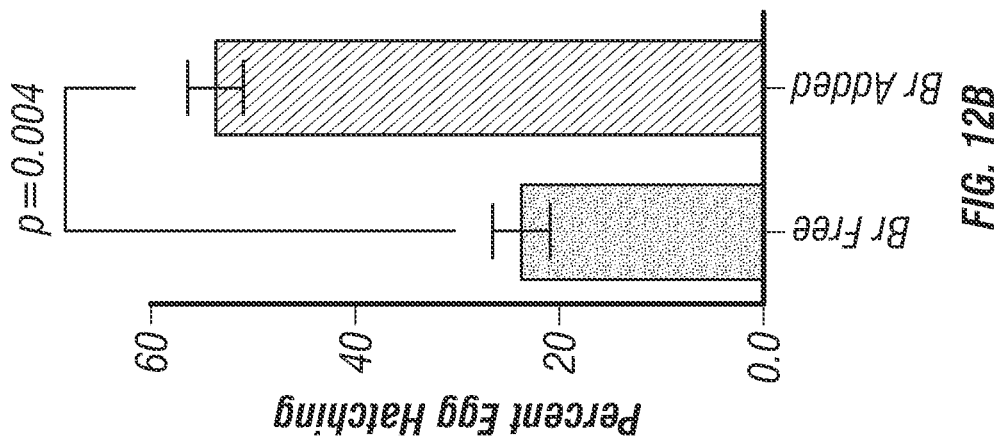
FIGS. 12A-B. Bromide depletion adversely effects collagen IV structure and embryonic viability.
Figure 12A:
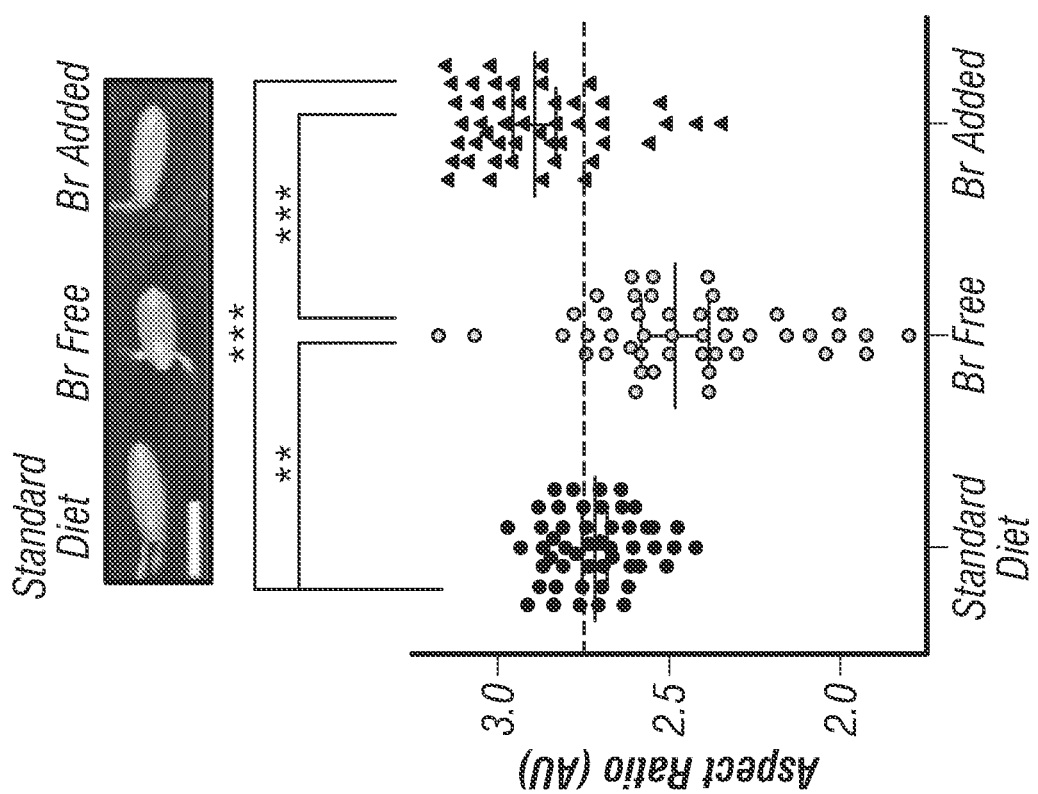

Through the course of bromide depletion of the adult females, the inventors also noticed a change in the gross-appearance and hatching frequency of the eggs deposited by the Br Free females compared to the Br Added cohort. The aspect ratio (calculated by dividing the anterior-posterior axis length by the egg's diameter) is a parameter of *Drosophila* eggs is known to be strongly influenced by both the structural and matrix signaling contributions of collagen IV. The rounding of eggs, quantified as a decrease in aspect ratio, has been shown to occur if collagen IV is unable to constrain the circumferential axis of the egg by forming a so-called "molecular corset" (Haigo et al., 2011; Bilder and Haigo, 2012). The inventors observed a decrease in aspect ratio of Br Free eggs, when compared to both the standard and Br Added diets. The addition of bromide rescued the decrease in aspect ratio (FIG. 12A). Interestingly, the increase in aspect ratio for the Br Added diet (100 μM Br—) eggs above that observed for the standard diet (15 μM Br—) is reminiscent of the trend in the amount of S=N bond formation observed in PFHR-9 cell culture (FIG. 10A) under similar bromide concentrations. In addition to the change in aspect ratio, the inventors found that there was a significant reduction (p=0.004) in the hatching rate of Br Free eggs compared to Br Added (FIG. 12B). This finding indicates that successful embryogenesis occurs less frequently in the absence of normal levels of bromide, adding an additional developmental stage at which bromide is required. Taken together, the study of *Drosopihla* has shown the essentiality of bromine for normal development as well as bromide-deficiency phenotypes similar to loss of function mutations in collagen IV and peroxidasin.

Example 5—Discussion

In this work, the inventors demonstrate that bromide is required for physiologic levels of sulfilimine bond formation within the collagen IV network and is essential for development in vivo. The identification of the sulfilimine bond within the NC1 domain of collagen IV (Vanacore et al., 2009), coupled with the recent discovery of peroxidasin's S=N bond formation function provide the scaffold on which bromide's in vivo mechanism can be understood (5). These data demonstrates an enzymatic and chemical selection for bromide within the collagen IV-peroxidasin-sulfilimine bond triad.

Bromine, existing almost entirely as Bromide in vivo, is present in the human body in levels around 3 mmol/75 kg, placing its content between other known essential trace elements such as Copper (Cu) and Iron (Fe) (24). Essential trace elements, by their very definition, are present in the body in very low concentrations yet have profound effects on biologic processes. Because of Bromine's relative abundance in both the oceans and human tissue, Frieden hypothesized that "Bromine is probably the most likely remaining nonmetal to qualify as an essential element" (Friede, 1985). In order for an element to be considered essential, it must be demonstrated that (a) deficient intake of that element results in physiologic dysfunction, (b) repletion of that specific element rescues the observed dysfunction, and (c) that there is a specific biochemical function associated with that element (Frieden, 1985; Mertz, 1981). The data presented in FIG. 5A demonstrate that a bromide deficient diet precludes development in *Drosophila*, and reintroduction of bromide specifically rescues the observed developmental deficiencies. The biochemical function of bromide can be better understood when examined by the criteria established by Mertz (Mertz, 1981) for assessing the basis for essential trace element action which involves three additional key areas of emphasis, as explained below:

Amplification: It is recognized for all essential trace elements yet identified that there is a need to interact with an enzyme or act as a part of a hormone to enable the interaction with a larger mass of physiologic substrate. Iodine requires activation and incorporation into thyroid hormones T3 and T4 (Freiden, 1981), and Cu incorporation into metalloenzymes (Uauy et al., 1998) both expand the effect of these elements beyond their stoichiometric presence in vivo. The activation of Br— by peroxidasin enables the crosslinking of many potential collagen IV molecules through its electrophilic catalysis of S=N bond formation (FIGS. 4B-C). The inventors' demonstration that depletion of bromide closely resembles the phenotype observed in peroxidasin hypomophic alleles strongly suggests that bromide's physiologic activation and amplification is in fact achieved by peroxidasin in vivo (FIGS. 5B-C)

Specificity: The niche of the essential element must be absolutely specific, and a deficiency only rectified by that element alone and not another, even chemically related element. These data show specificity at multiple levels within peroxidasin-collagen IV axis. Enzymatically, peroxidasin is unable to form physiologic levels of S=N bond with any other halide than bromide (FIGS. 1C, 2C-D). The finding that there is an enthalpic preference by Met93 for a S—Br HSI in S=N bond formation within the NC1 domain provides clear rationale why Cl and Br are not interchangeable for this essential biological function (FIG. 3D). Finally, the depletion of bromide within *Drosophila* and its ability to rescue the observed phenotypes upon repletion shows its hitherto unappreciated specificity within physiology (FIG. 5A).

Homeostatic Regulation: The element must be maintained at a relatively constant and optimal physiologic concentration across a variety of dietary and environmental conditions. There has been consensus across five decades, multiple methods of measuring serum bromide, and many investigators on several continents that serum bromide in healthy individuals is remarkably consistent around 5.4 mg/L (67.6 µM) (Kirk, 1991; Olszowy et al., 1998; van Leeuwen et al., 1987). Bromide is found primarily extracellularly (Barratt and Walser, 1969), and like chloride is excreted renally (Wolf and Eadie, 1950). Several studies in humans and dogs demonstrate that bromide has preferential tubular reabsorption to chloride (Wolf and Eadie, 1950; Walser and Rahill, 1966; Trautner and Wieth, 1968). Given the tight regulation of physiologic chloride concentrations, these observations offer a plausible mechanism by which serum bromide concentrations are maintained at optimal ratios by linkage to tubular chloride regulation (Trautner and Wieth, 1968). Lending support to this hypothesis, the only reported instance of bromide deficiency in humans occurred in patients undergoing hemodialysis (Canavese et al., 2006). Conversely, the long medical history of pharmacologic use of bromide to treat neurological and pshyciatric issues has demonstrated that the clinical syndrome of 'Bromism' occurs when there is excess bromide present (>12 mmol/L), resulting in neurologic and occasionally dermatologic manifestations (van Leeuewen Trautner and Wieth, 1968 1987; Carney, 1971). The observation of a maintained plateau, suboptimal, and toxic ranges for bromide in physiology is consistent with Bertrand's rule for essential nutrients (Mertz, 1981) and likely evidence of homeostatic regulation.

The discovery of an essential function for bromide escalates bromine to the list of known essential elements. Bromide appears to be essential for tissue formation, not cellular function as evidenced by the ability of yeast and mammalian cells to grow despite its absence. However when bromide was removed from *Drosophila* and mammalian culture model systems, the collagen IV network failed to properly form. In *Drosophila*, this resulted in developmental lethality. The conservation of the sulfilimine bond, peroxidasin, and collagen IV in all animals with true differentiated tissues suggest that bromide might be essential across all eumetazoa.

Example 6—Results

Figure 17A:
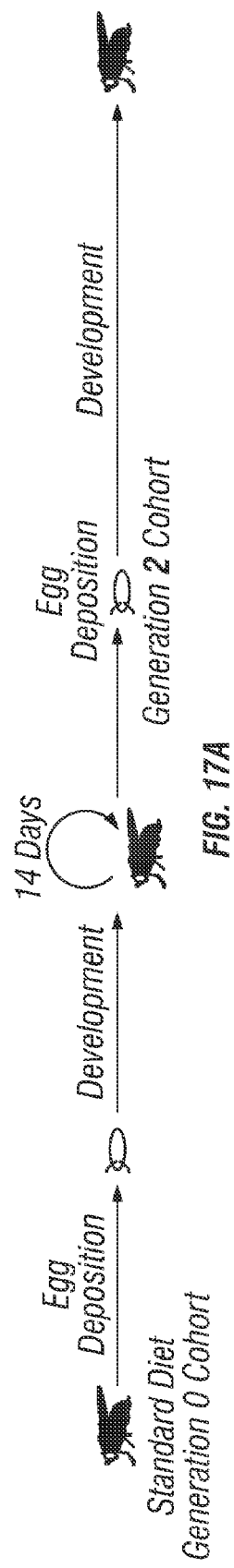
Figure 17B:
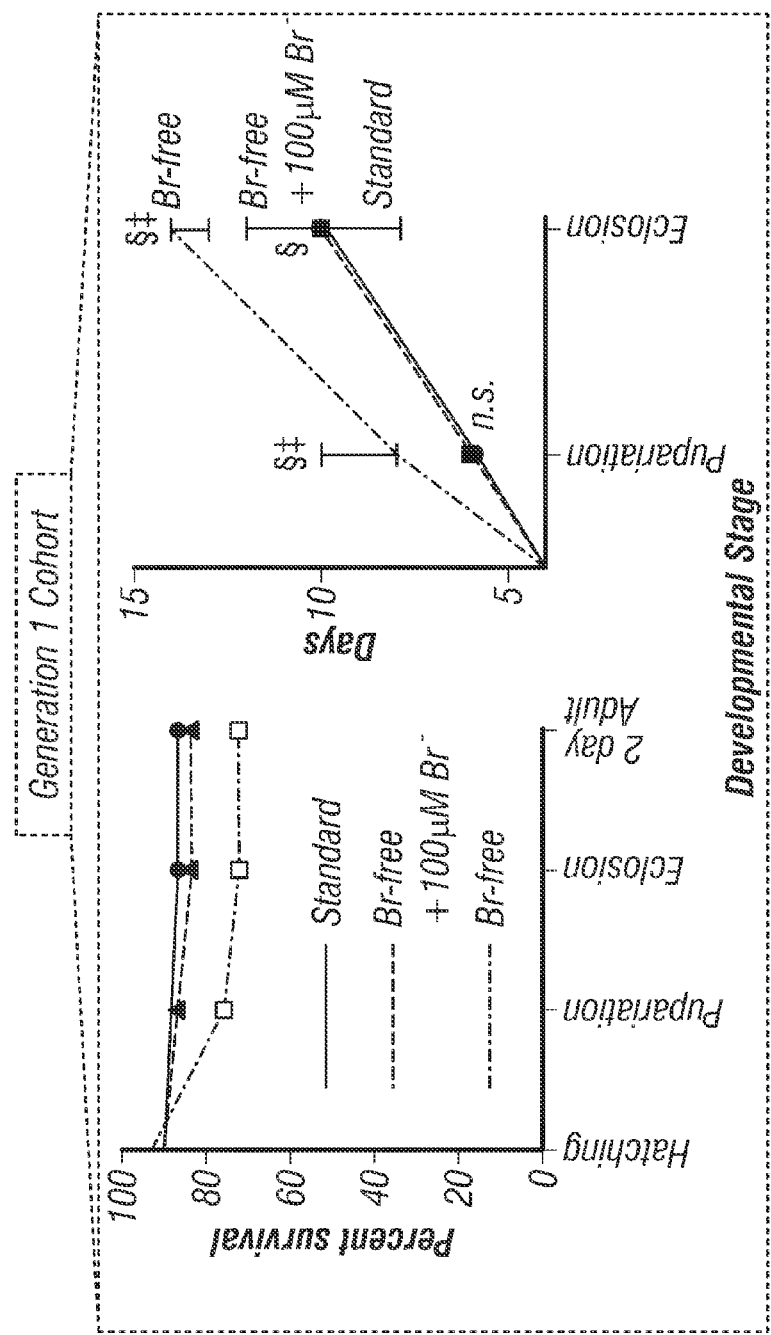
Figure 17C:
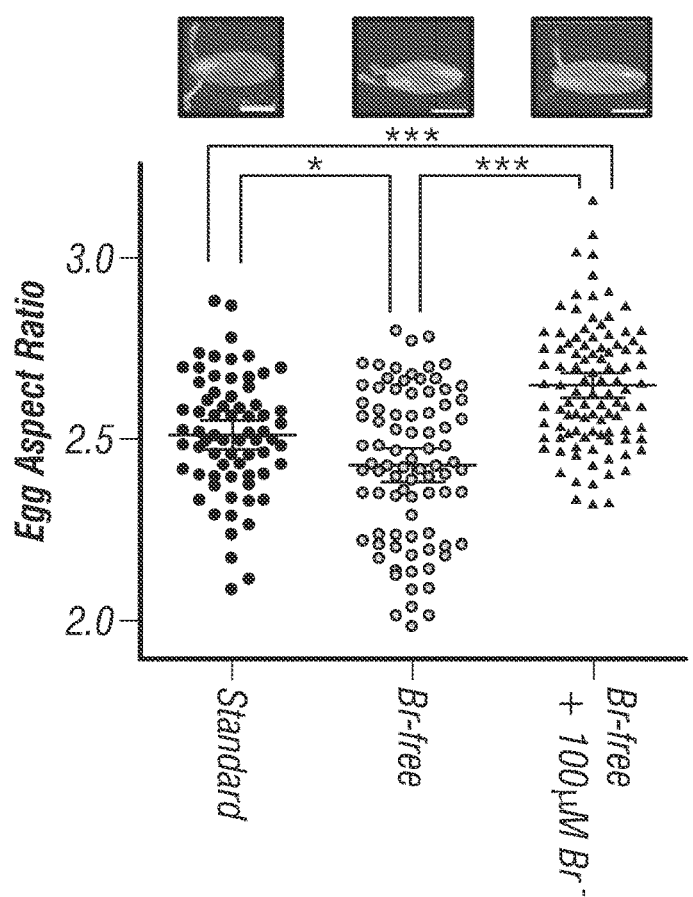

Based on the chemical requirement for Br$^-$ in collagen IV sulfilimine bond formation and the conservation of the crosslink in multicellular tissues (Fidler et al., 2014), the inventors hypothesized that Br$^-$ is essential for stabilizing tissues and tested this hypothesis in *Drosophila*. Because standard *Drosophila* media contains ~15 µM Br$^-$, the inventors prepared a custom diet in which final dietary Br$^-$ was undetectable by NAA. To address the impact of Br$^-$ deficiency over multiple generations, flies were raised on Br-free media, and compared their development to cohorts raised on either similar media with Br$^-$ supplementation (Br-added media) or standard media (FIG. 17A). Maternal Br$^-$ contribution in embryos was 24.3 µM on the standard diet. After moving embryos to the indicated media, Generation 1 larvae grown on Br-free conditions exhibited developmental delay (FIG. 17B), yet development rates were similar between Br-added and standard media. Adult Generation 1 flies that survived were maintained on the same diet for 14 days to continue Br$^-$ depletion, and progeny Generation 2 larvae showed significantly reduced survival in Br-free versus standard; the phenotype was rescued in Br-added diet (FIG. 17C). Thus, Br$^-$ is essential for development in *Drosophila*.

Figure 17D:
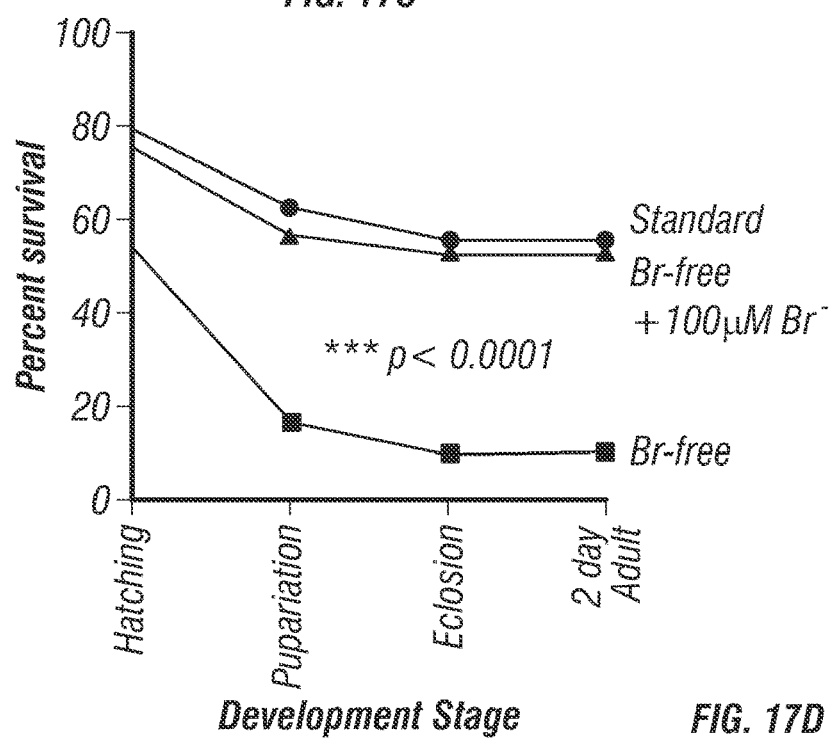
Figure 17E:
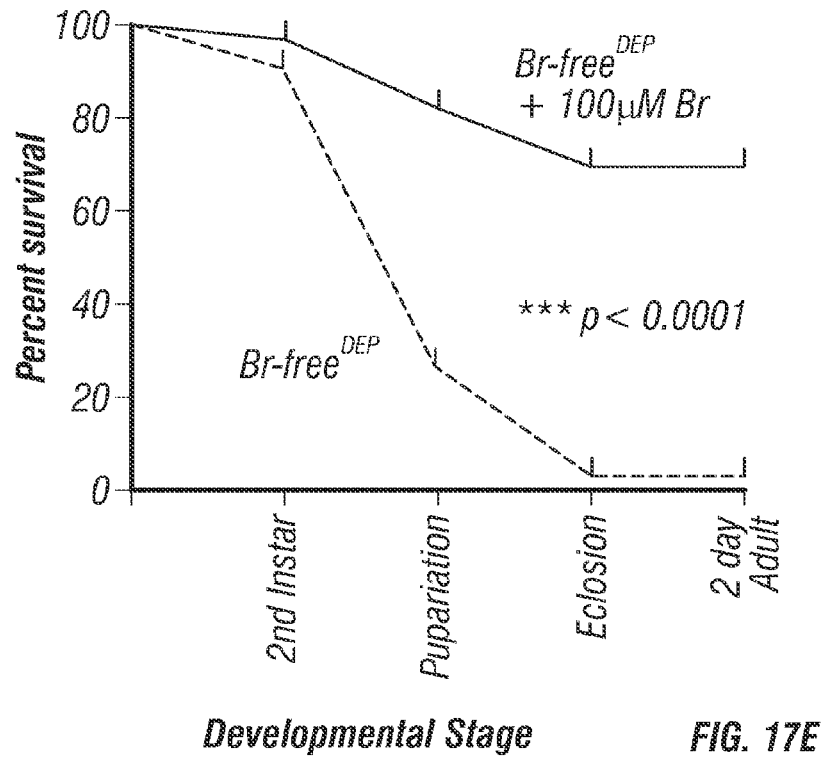
Figure 17F:
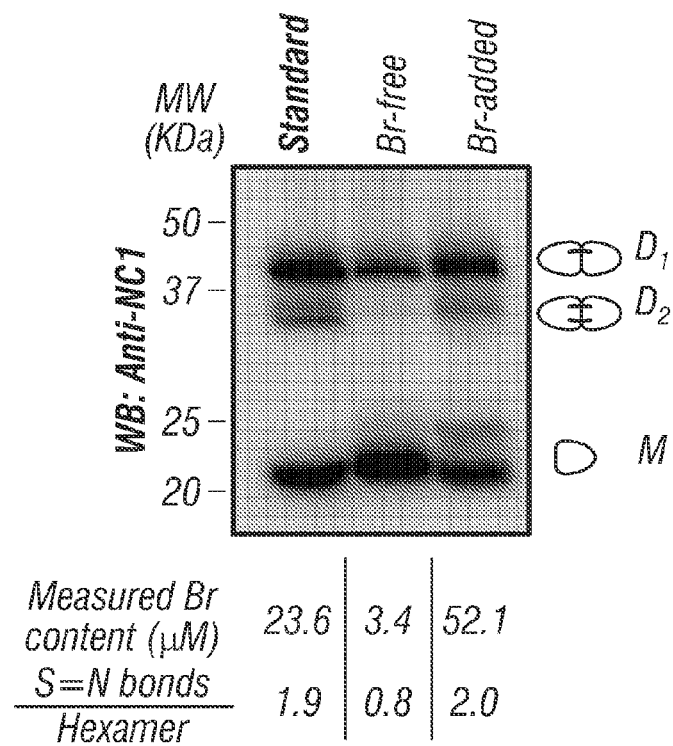
Figure 17I:
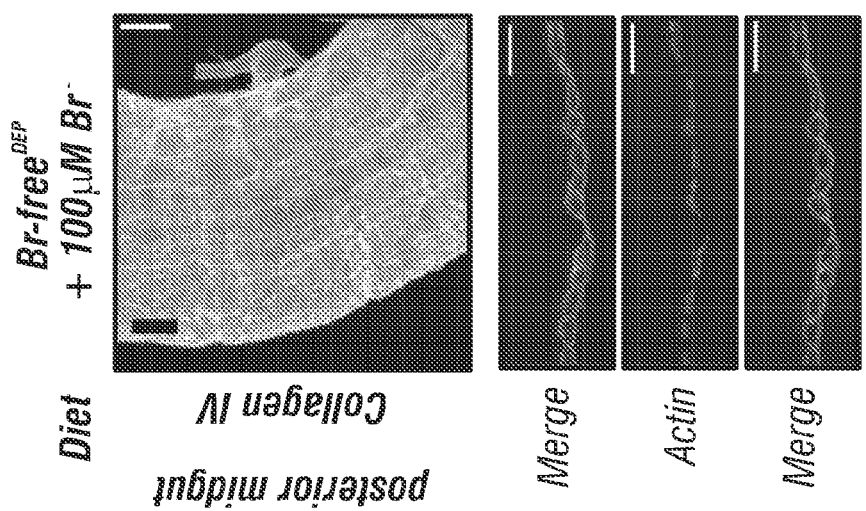

To accelerate Br-depletion, flies were fed a Br-free diet containing elevated NaCl levels to reduce Br$^-$ half-life in vivo via halide flux as shown in mammals (Pavelka et al., 2005). Female *Drosophila* were placed on a Br$^-$ depleting (Br-free$^{DEP}$) diet with or without supplemental 100 µM Br$^-$ (Br-added$^{DEP}$) prior to egg deposition, and the dietary conditions were maintained throughout progeny development. Initially, the Br-free$^{DEP}$ egg cohort had a significantly reduced hatching percentage relative to Br-added$^{DEP}$ (FIG. 17D), suggesting that Br is required for successful embryogenesis. Nearly all hatched larvae died prior to eclosion under Br-free$^{DEP}$ conditions, while 100 µM Br$^-$ rescued development to adulthood (FIG. 17E). NAA analysis confirmed lower Br$^-$ levels in third instar larvae (3.4 vs. 23.6 µM for controls) in Br-free$^{DEP}$ conditions (FIG. 17F).

In Br-free$^{DEP}$ conditions, the inventors assessed the impact of Br-deficiency on crosslink formation in vivo. The inventors used vkg$^{454}$-GFP flies in which the single collagen IV α2 gene locus contains a GFP insertion near the 7S domain. vkg$^{454}$-GFP flies were grown on Br-free$^{DEP}$, Br-added$^{DEP}$ and standard diets and biochemically assayed sulfilamine-bond content via immunoblot. The inventors found grossly reduced sulfilimine-bond content in the Br-free$^{DEP}$ cohort, which was rescued with Br$^-$ supplementation (FIG. 17F). Thus, Br$^-$ promotes sulfilimine formation in vivo.

Figure 17H:
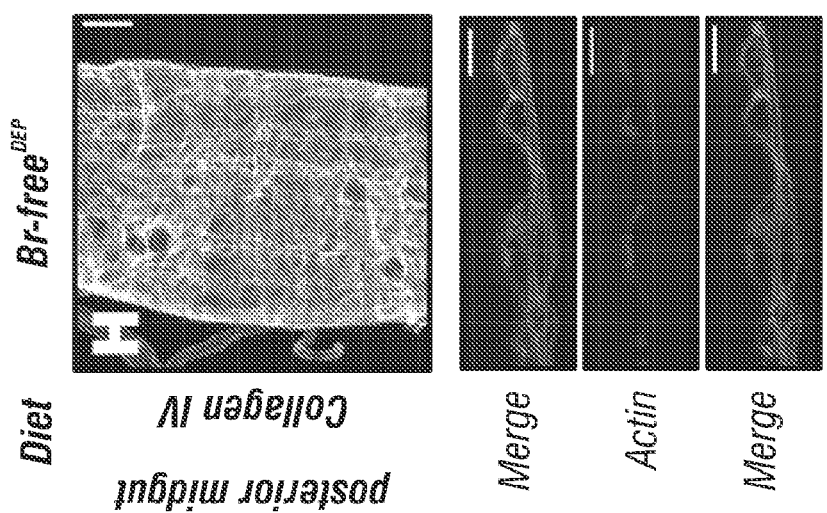
Figure 17G:
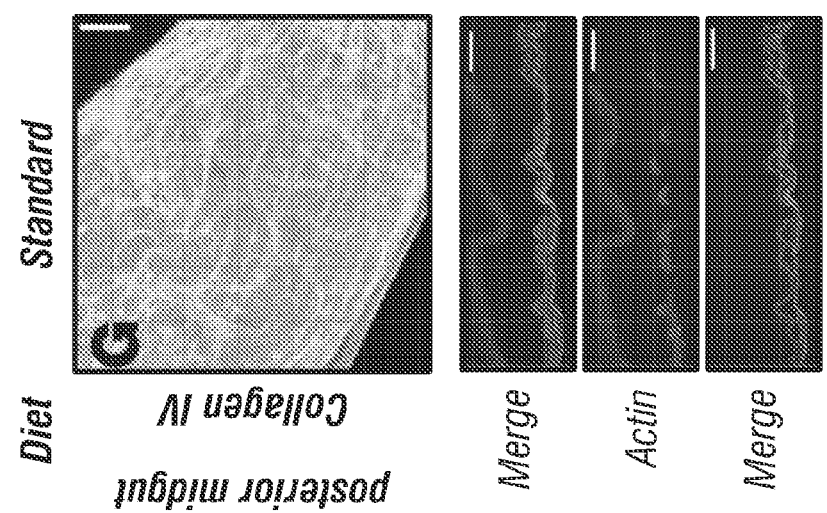

The inventors compared the BM ultrastructure in Br-depleted larvae with Pxn mutant larvae via transmission electron microscopy (TEM). Larvae raised on standard diet exhibited normal enterocyte and BM structure (Shanbhag, and Tripathi, 2009) (FIG. 5N). In Br-free$^{DEP}$ larvae, the BM was irregular, thickened, occasionally diffuse, and wavy in various sections (FIG. 17O). Moreover, Br-free$^{DEP}$ conditions displayed circular muscles protruding into and deforming the epithelium, mirroring the perturbed actin staining in circular muscles observed in Br-free$^{DEP}$ treatment (FIGS. 17H,K,M). All sections from the Br-added$^{DEp}$ and standard diet cohorts displayed normal BM and circular muscle morphologies (FIGS. 17N, 17P). The inventors quantified the BM morphologic changes observed by TEM, finding similar BM thickness in the standard and Br-added$^{DEP}$ diets but significantly thicker BMs in Br-free$^{DEP}$ treatment (FIG. 17S).

Figure 18A:
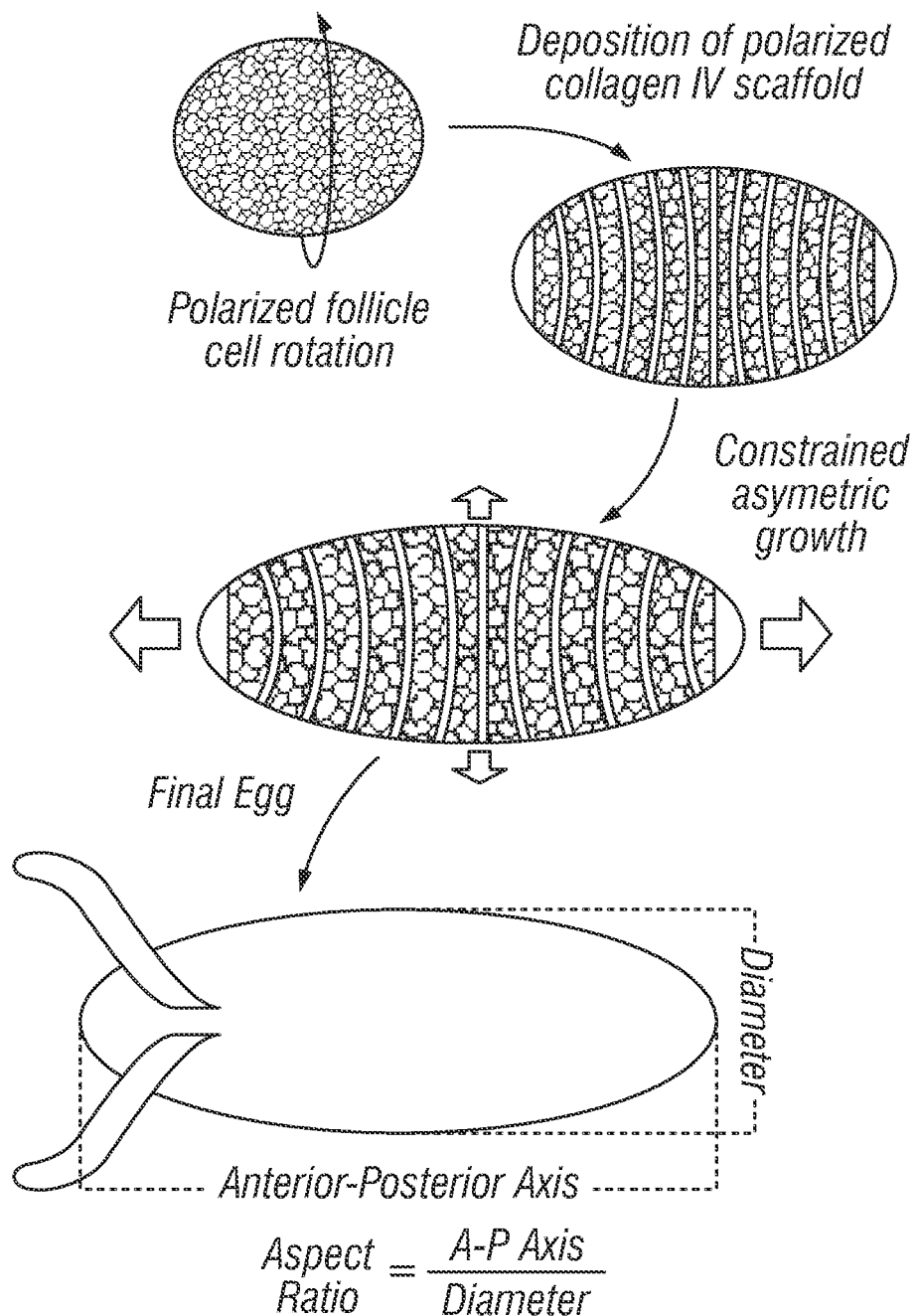
FIGS. 18A-E. Br⁻ and peroxidasin interact in vivo to strengthen collagen IV scaffolds.
Figure 18B:
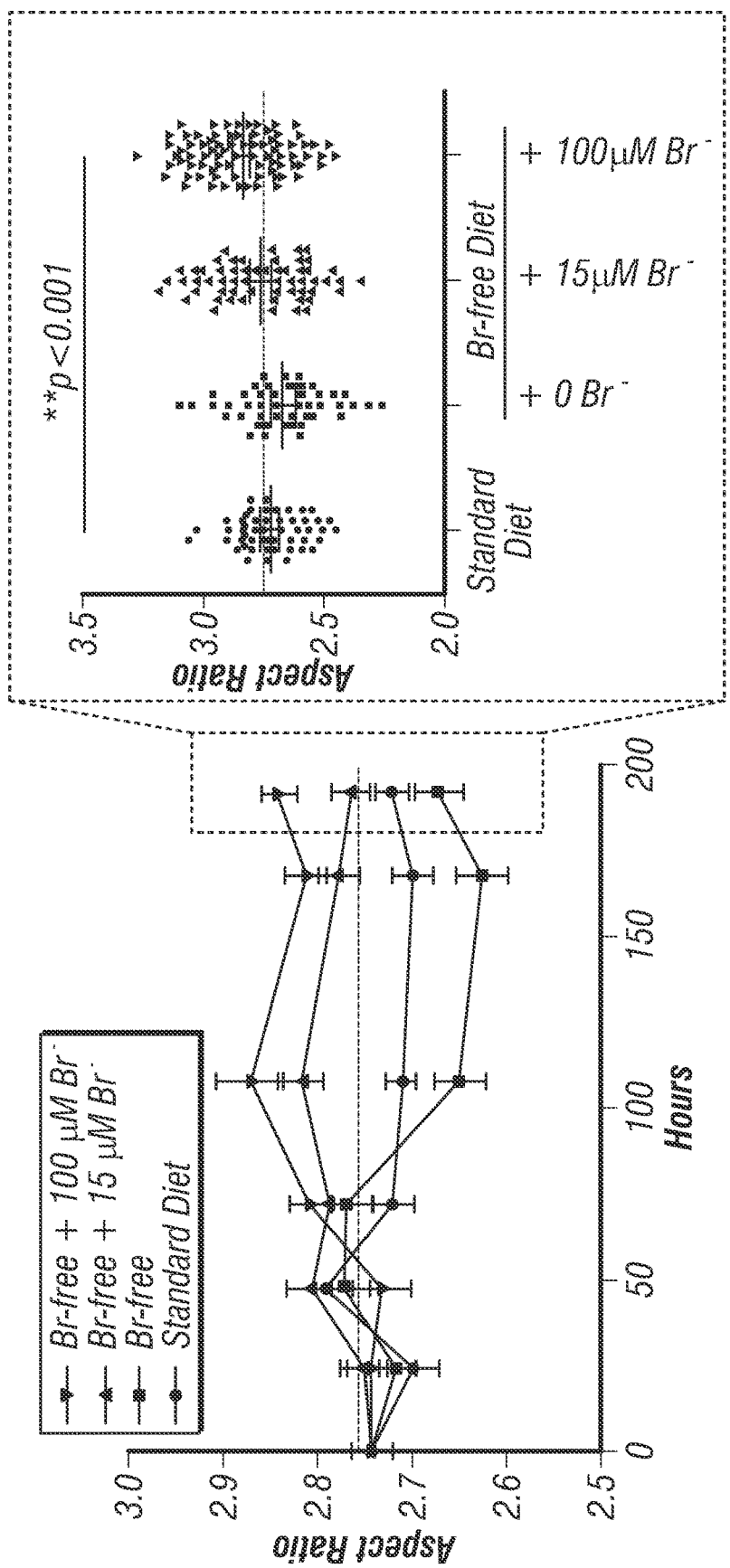
Figure 18C:
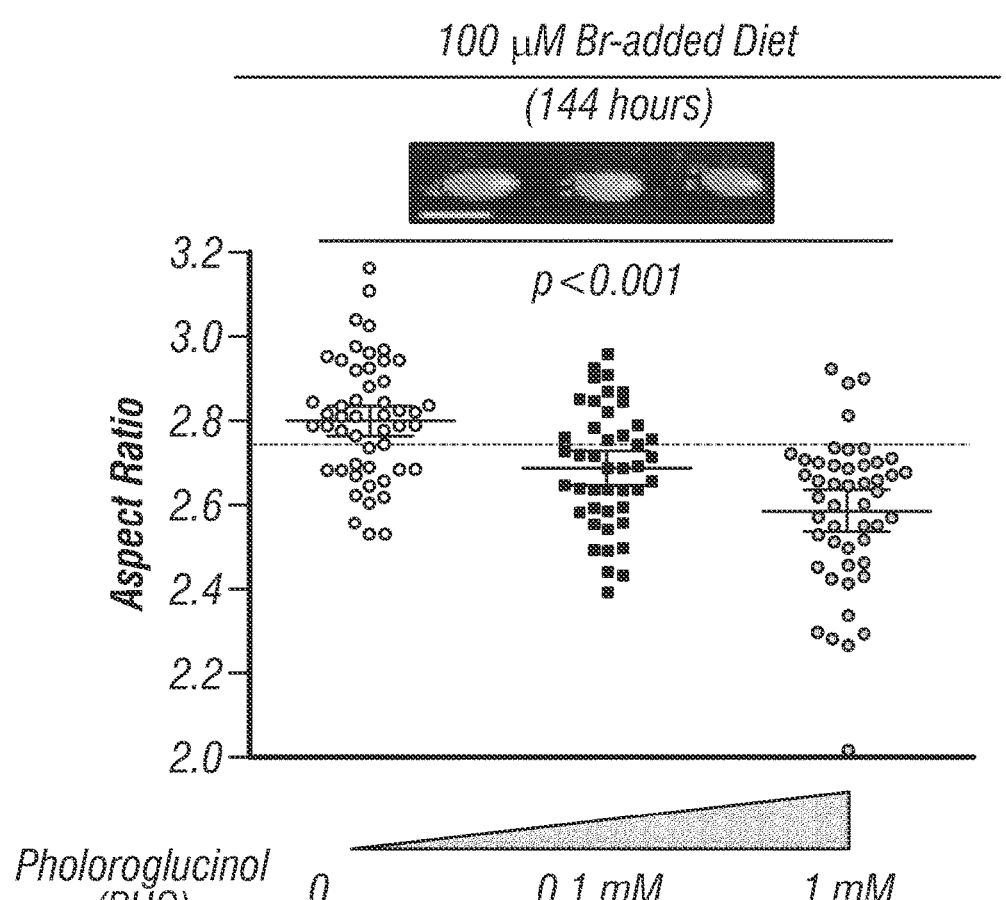
Figure 18E:
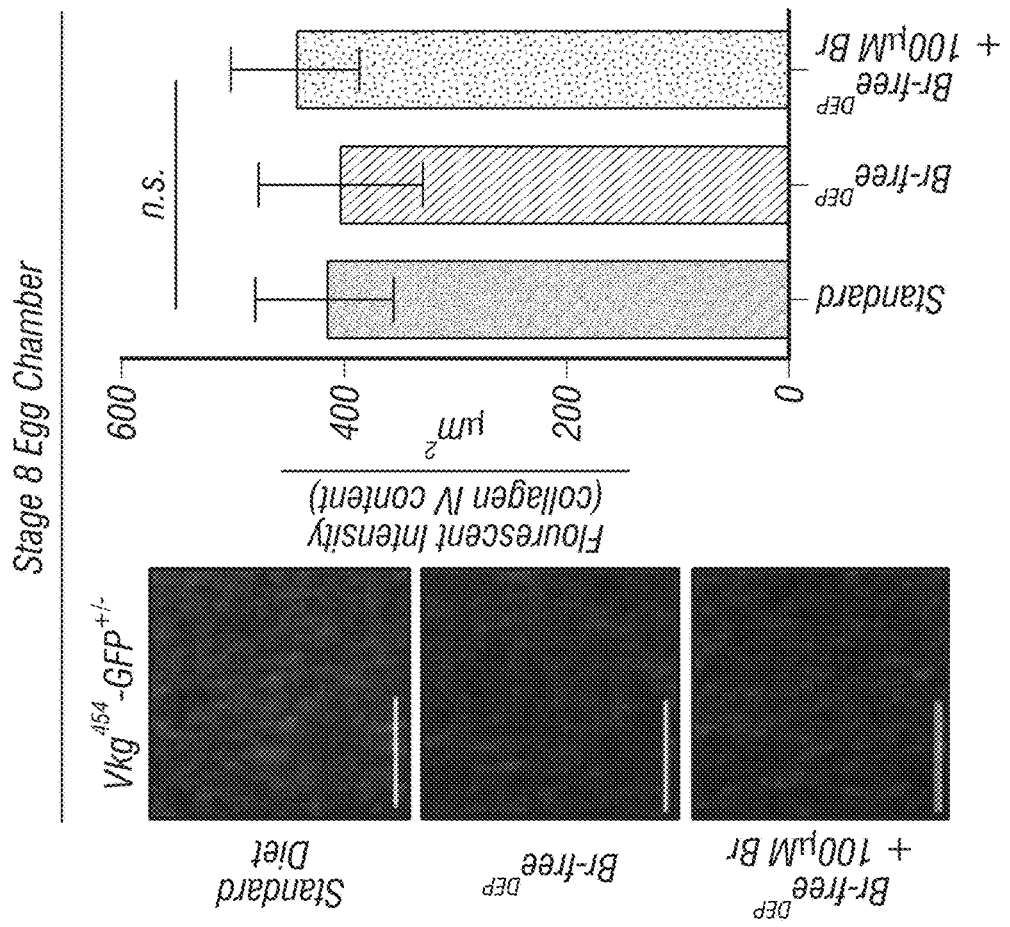
Figure 18D:
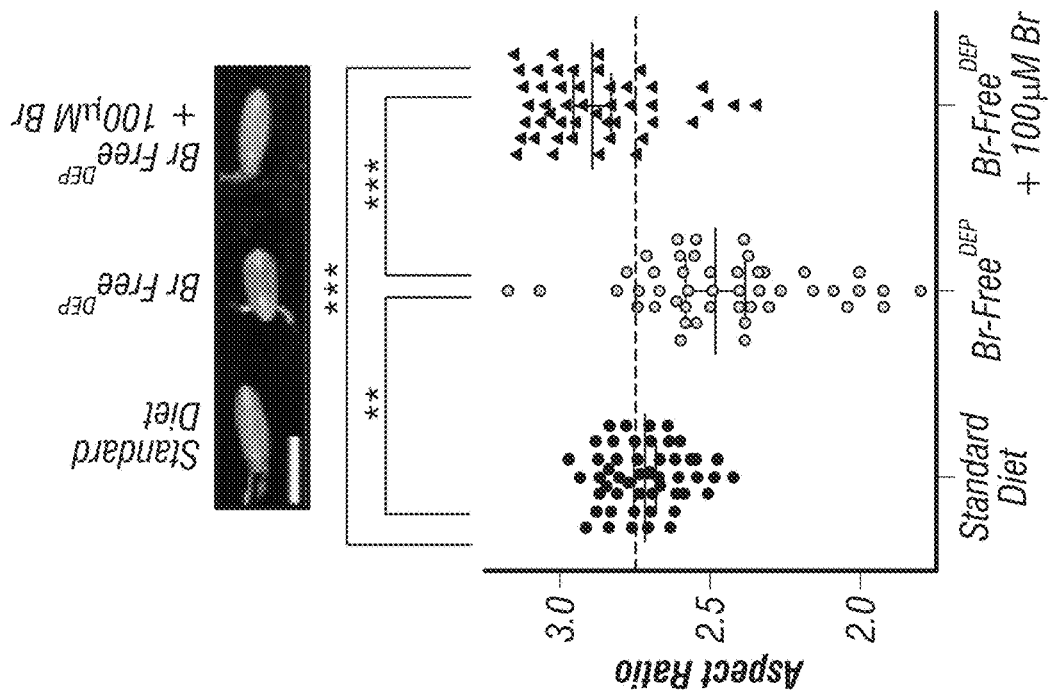

Br-free$^{DEP}$ conditions phenocopy the genetic loss of Pxn (Bhave et al., 2012) so the inventors hypothesized that Br$^-$ and Pxn interact in vivo to strengthen collagen IV scaffolds. It has been reported that collagen IV acts during *Drosophila* oogenesis as a "molecular corset" to control egg shape, restricting circumferential expansion so that egg growth promotes elongation along the anterior-posterior axis (FIG. 18A) (Haigo and Bilder, 2011). In eggs from mothers fed varying concentrations of Br, the inventors found a dose-dependent relationship between $Br^-$ and aspect ratio (FIG. 18B), evident after four days, a time course consistent with $Br^-$ having a long biologic half-life. Interestingly, the aspect ratio of eggs on the Br-added diet (100 μM $Br^-$) exceeded the ratio for eggs on standard diet (NAA measured 15 μM $Br^-$) (FIG. 18B) suggesting that elevated $Br^-$ promotes additional sulfilamine formation to enhance tensile strength in the collagen IV molecular corset.

The inventors used this elongated egg aspect ratio to probe whether $Br^-$ and Pxn act via a common mechanism in strengthening collagen IV. The inventors asked if Pxn is required for the elongation phenotype. An irreversible inhibitor, phloroglucinol, was used to inhibit peroxidasin activity, and caused a dose-dependent suppression in egg aspect ratio in the presence of elevated $Br^-$ (FIG. 6C). Thus Pxn is required for the Br-induced elongation phenotype. To address the alternative hypothesis that $Br^-$ levels modulate collagen IV deposition, Vkg-GFP immunofluorescence was examined in eggs from mothers raised on Br-free$^{DEP}$ media. Like the Br-deficient diet, the Br-free$^{DEP}$ media reduced egg aspect ratio (FIG. 18F), but collagen IV content appeared similar to controls (FIG. 18G) after one week of maternal exposure to Br-free$^{DEP}$ diet, suggesting that the egg aspect-ratio phenotypes are caused by structural deficiencies within the scaffold.

Example 7—Discussion

Essentiality and Function of Bromide in Animals.

The inventors provide evidence that bromine is essential in animals, satisfying the principal requirements for elemental essentiality: (1) demonstration that elemental deficiency leads to physiologic dysfunction, (2) repletion of the element that reverses dysfunction, and (3) biochemical explanation of the physiologic function (Mertz, 1981). Br-deficient *Drosophila* display altered BM and tissue morphology, aberrant embryogenesis, larval mid-gut defects, and lethality, whereas $Br^-$ repletion restored normal development. Mechanistically, the assembly of crosslinked collagen IV scaffolds requires $Br^-$. Sulfilimine-crosslinked collagen IV scaffolds are central to the form and function of BMs in animals (Bhave et al., 2012; Fidler et al., 2014). These data indicate that the crosslink stabilizes nascent collagen IV scaffolds, effectively modulating scaffold assembly and BM thickness. Because sulfilimine formation involves the concerted activity of collagen IV, Br, peroxidasin, and oxidant, the inventors view each as critical for BM assembly and tissue development.

Mechanistic Role of Bromide in Sulfilimine Formation.

The requirement for $Br^-$ during sulfilimine formation derives from the selectivity of the bromosulfonium reaction intermediate. The chemical character of bromine uniquely creates an energetically favorable reaction between the S—Br intermediate and Hyl$^{211}$. The S—Br molecular orbital structure facilitates selective reactivity with an amine nucleophile to form the crosslink, contrasting with the highly polar S—Cl intermediate that preferentially forms a sulfoxide via charge-controlled reaction with water. Peroxidasin harnesses this HOBr-based selectivity during cross-linking while apparently avoiding oxidative damage to the BM.

Bromide Homeostasis.

$Br^-$ is mainly located extracellularly and has been used in the clinical measurement of extracellular volume (Barratt and Walser, 1969; Brodie et al., 1939). Plasma $Br^-$ is 67 μM in healthy individuals, congruent with $Br^-$ concentrations that support sulfilimine formation in flies, and are maintained within an order of magnitude in many species (freshwater fish (Woods et al., 1979), flies (Piedade-Guerreiro et al., 1987), rodents (Van Logten et al., 1974), and humans (Olszowy et al., 1998; van Leeuwen and Sangster, 1981)). In humans, plasma $Br^-$ is maintained via diet and renal excretion (Trautner and Wieth, 1968; van Leeuwen and Sangster, 1981; Walser and Rahill, 1966; Wolf and Eadie, 1950). Dietary Br-deficiency has been suggested to suppress tissue growth and increase lethality in goats (Anke et al., 1990), while high serum $Br^-$ (>12 mM) causes neurologic and dermatologic complications (van Leeuwen and Sangster, 1987). Taken together, this implies that an optimal $Br^-$ concentration might exist and is regulated in vivo.

Clinical Implications of Bromide Deficiency.

Figure 13A:
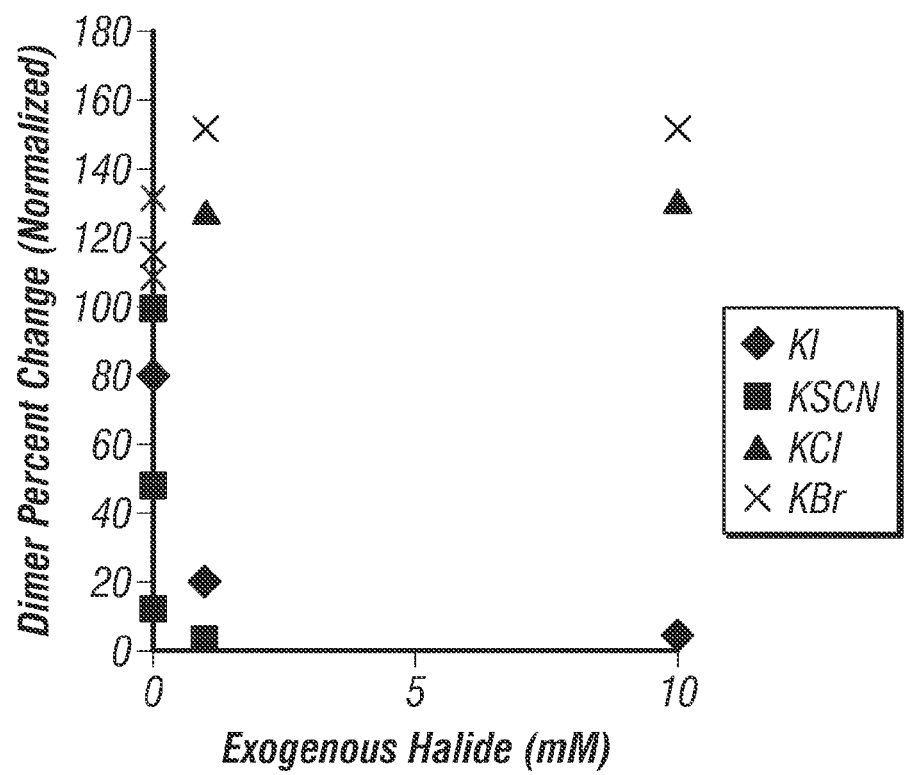
FIGS. 13A-D. Bromide Enhances Collagen IV Sulfilimine Bond Formation in Culture.
Figure 13B:
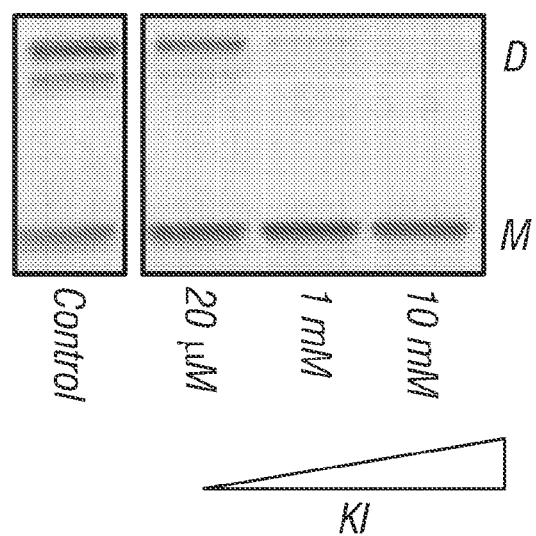
Figure 13C:
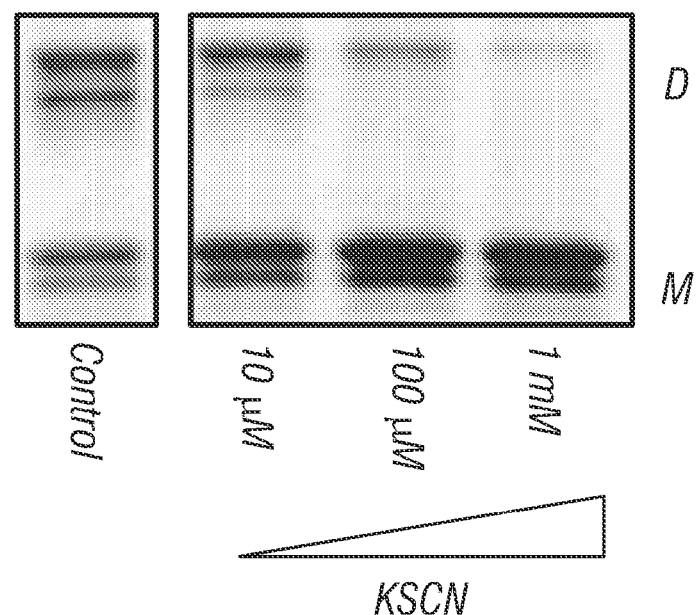
Figure 13D:
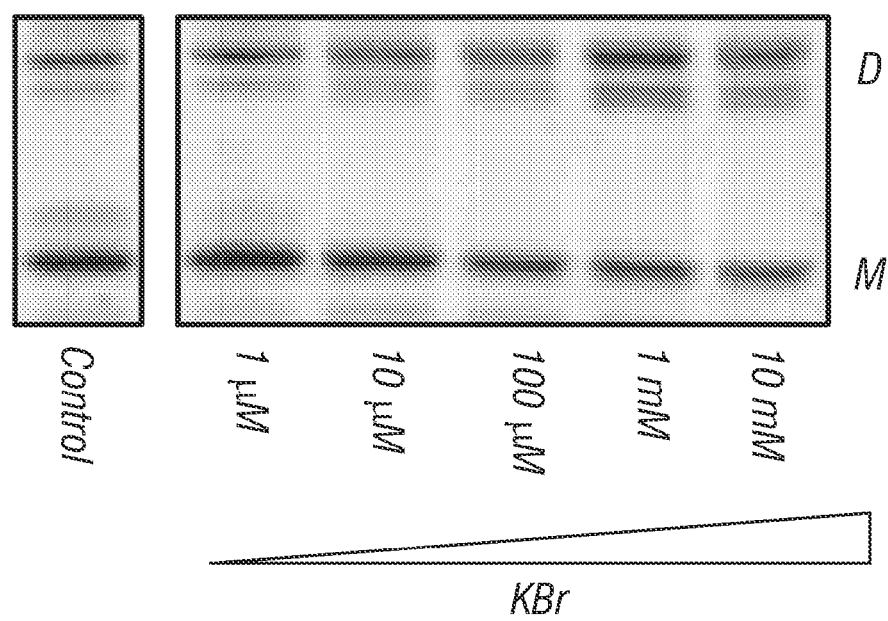
Figure 14B:
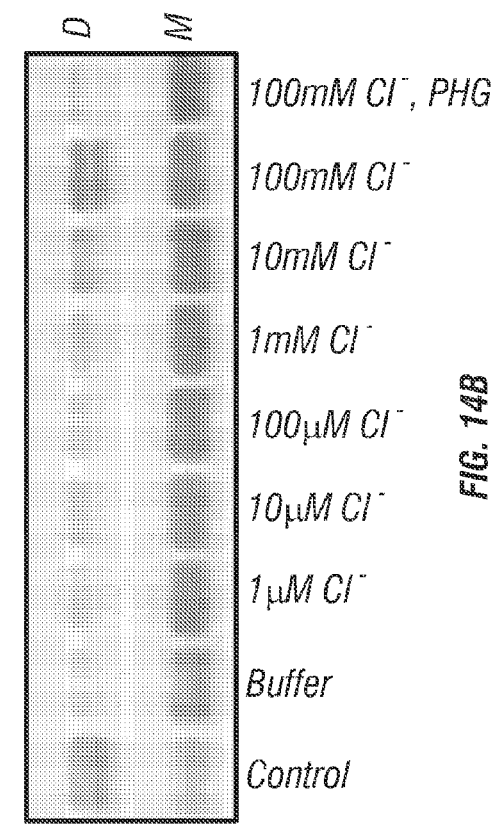
FIGS. 14A-D. Physiologic Bromide Concentrations are Sufficient for Sulfilimine Bond Formation by PXDN. Uncrosslinked PFHR9 matrix was extensively washed into 10 mM phosphate buffer (pH 7.4) that was supplemented with 100 mM KF to maintain ionic strength. One hour reactions at 37° C. were initiated by addition of $H_2O_2$ to 1 mM and stopped by freezing at $-20°$ C.
Figure 14D:
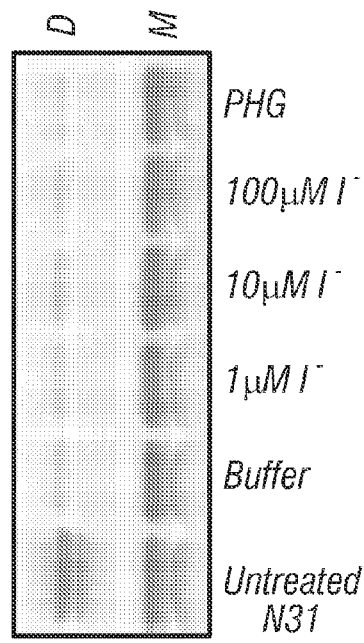
Figure 14A:
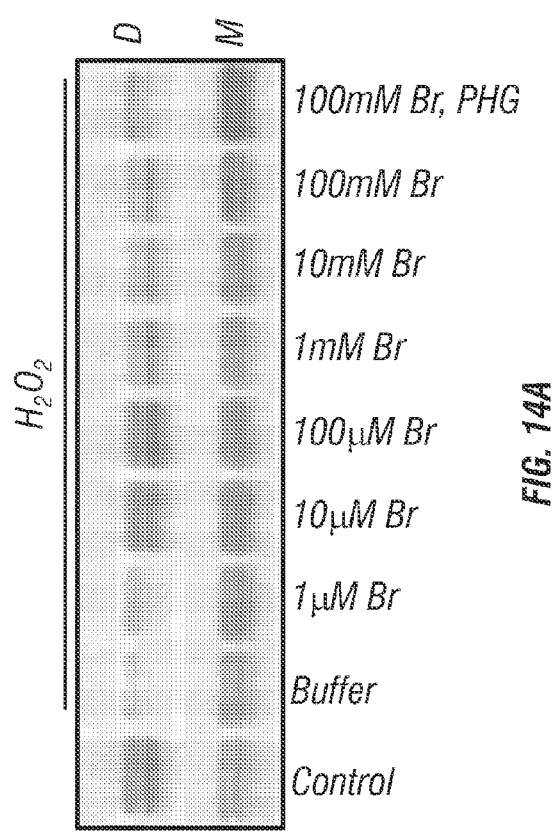
Figure 14C:
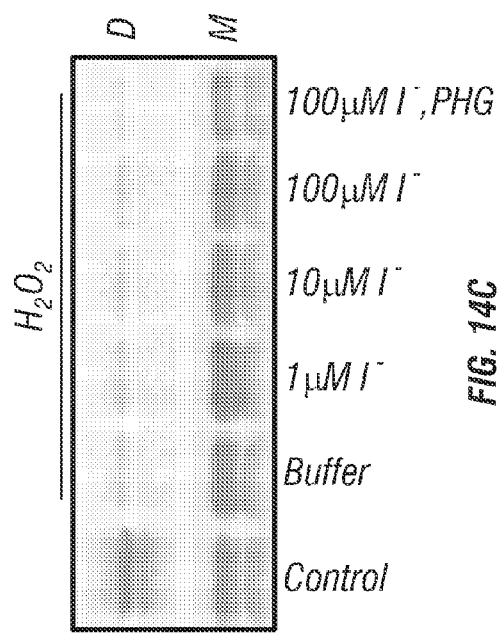
Figure 15A:
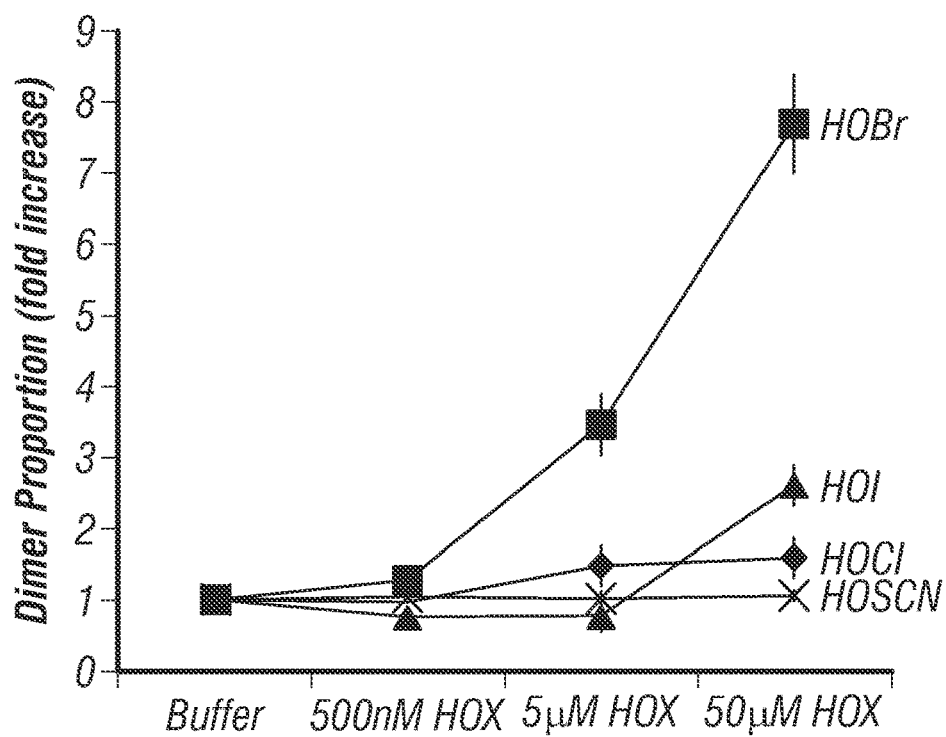
Figure 15B:
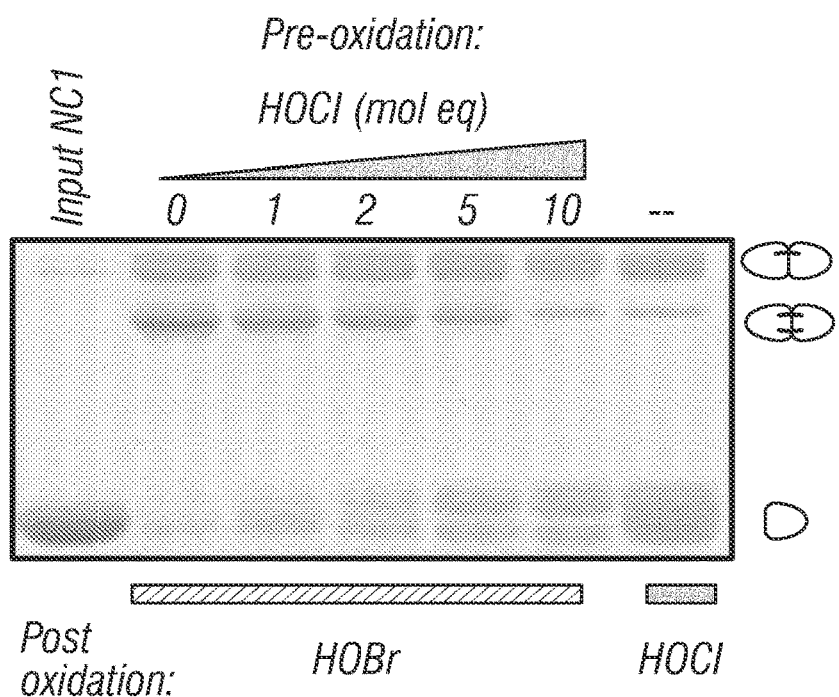
Figure 16B:
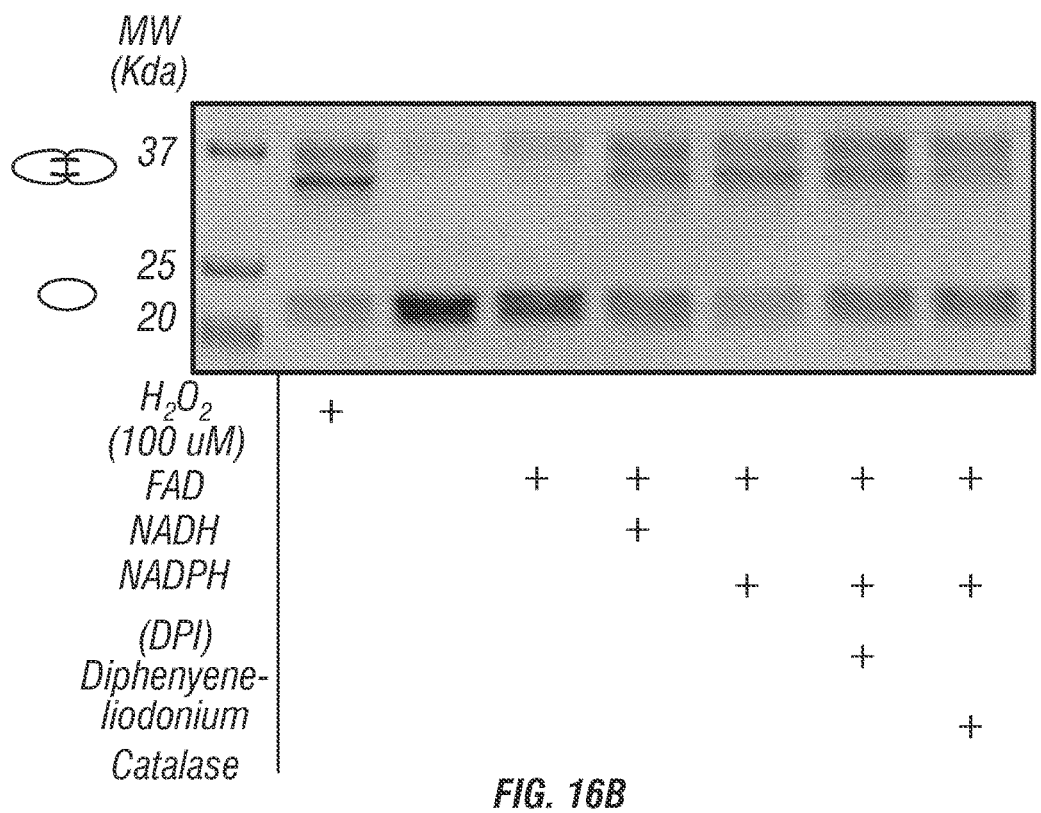
Figure 16C:
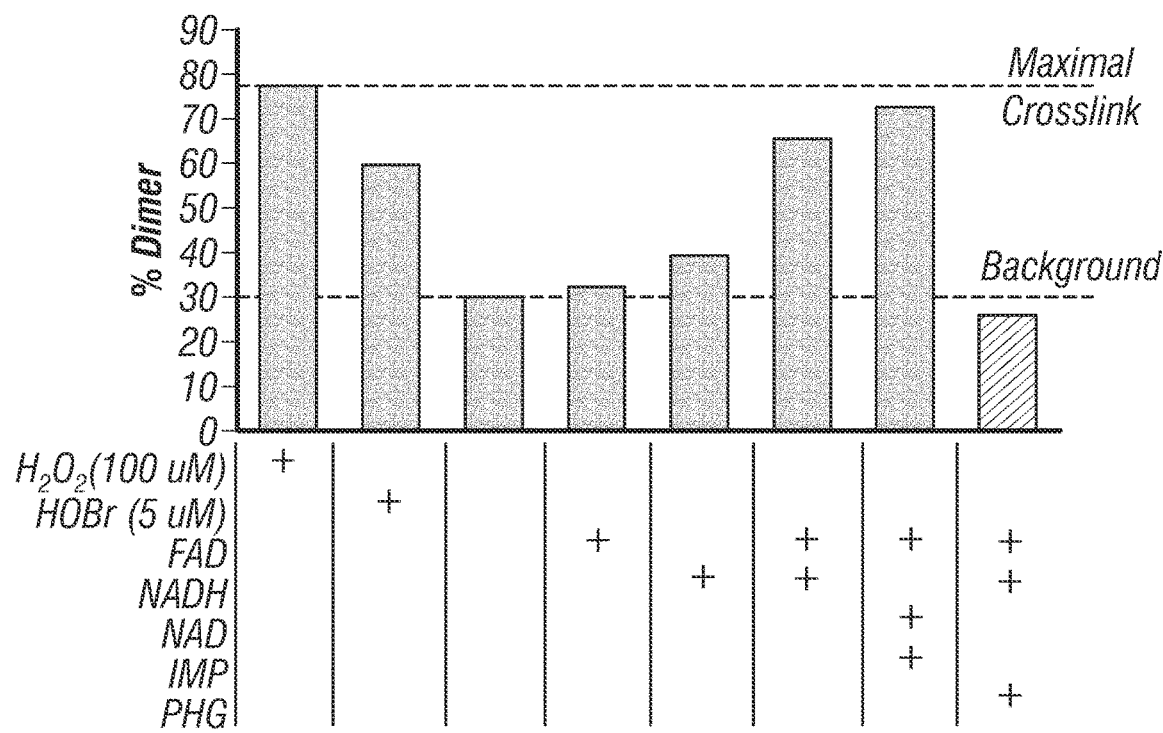
Figure 16D:
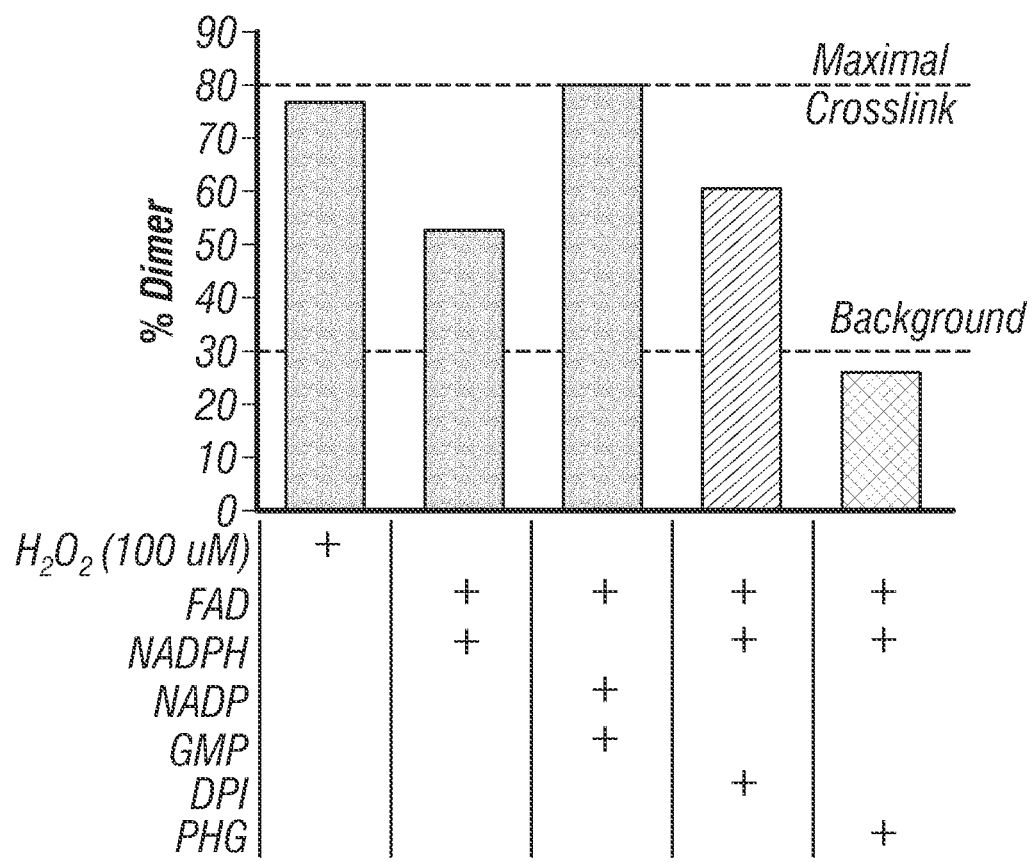

Bromide deficiency may have implications in human health and disease. Patients receiving total parenteral nutrition (TPN) are reported to have low plasma $Br^-$ levels due to nutritional Br-deficiency (Dahlstrom et al., 1986), and end-stage renal disease patients have enhanced $Br^-$ losses as a consequence of dialysis (Miura et al., 2002; Oe et al., 1981; Wallaeys et al., 1986). Since Br has not been considered an essential trace element, systematic investigations on $Br^-$ replacement have not been pursued in these disease states (Nielsen, 1998). Intriguingly, TPN alters intestinal mucosal architecture and function in a manner reminiscent of the mid-gut phenotypes of *Drosophila* Pxn mutants and Br-deficient larvae (Groos et al., 2003). Furthermore, functional Br-deficiency may occur in smokers in spite of normal plasma $Br^-$ levels because of elevated levels of serum $SCN^-$. The inventors have noted that $SCN^-$ is a potent inhibitor of peroxidasin-mediated crosslink formation in cell culture (FIGS. 13A, 13C). Therefore, in some smokers with elevated $SCN^-$ levels (130 μM, 1 pack per day) (Tsuge et al., 2000), reinforcement of collagen IV scaffolds with sulfilimine crosslinks may be substantially reduced. Indeed, smoking has been associated with architectural changes within BMs (Asmussen, 1979; Soltani et al., 2012). Finally, since BM assembly involves Br, tissue development or remodeling may be vulnerable to Br-deficiency. The findings of the inventors provide rationale for investigating the clinical implications of Br-deficiency and the physiologic consequences of mechanically perturbing collagen IV scaffolds.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods, and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Akomeah et al., *Eur. J. Pharm. Sci.*, 21(2-3):337-45, 2004.
Aouacheria et al., *Mol. Biol. Evol.*, 23:2288, 2006.
Baxter and Mitragotri, *J. Control. Release*, 106(3):361-73, 2005.
Borza et al., *J. Biol. Chem.*, 280:27147, 2005.
Bramson et al., *Gene Ther.*, 10(3):251-60, 2003.
Cheng et al., *Free Radic. Biol. Med.*, 45:1682, 2008.
Cope et al., *J. American Chemical Soc.*, 82:4663, 1960.
Cortez et al., *Arch. Biochem. Biophys.*, 254(2):504-8, 1987.
Fox et al., *Cell*, 129:179, 2007.
Gilchrist and Moody, *Chemical Rev.*, 77:409, 1977.
Glass and Duchek, *J. American Chemical Soc.*, 98:965, 1976.
Gould et al., *N. Engl. J. Med.*, 354:1489, 2006.
Gould et al., *Science*, 308:1167, 2005.
Hudson et al., *N. Engl. J. Med.*, 348:2543, 2003.
Hynes, *Cell*, 110:673, 2002.
Kay et al., *J. American Chemical Soc.*, 114:10663, 1992.
Khoshnoodi et al., *J. Biol. Chem.*, 281:6058, 2006.
Khoshnoodi et al., *Microsc. Res. Tech.*, 71:357, 2008.
Kivirikko and Pihlajaniemi, *Adv. Enzymol. Relat. Areas Mol. Biol.*, 72:325, 1998.
Lagerwerf et al., *Rapid Commun. Mass Spectrom.*, 10:1905, 1996.
Lambeth and Swank, *Federation Proc.*, 38:830, 1979.
Licklider et al., *Anal. Chem.*, 74:3076, 2002.
Moser et al., *Science*, 324:895, 2009.
Nelson et al., *Embo J.*, 13:3438, 1994.
Palmer et al., *J. Magnetic Resonance*, 93:151, 1991.
Péterfi et al. *Am. J. Pathol.*, 2009
Reid et al., *J. Proteome Res.*, 3:751, 2004.
Schleucher et al., *J. Biomol. NMR*, 4:301, 1994.
Siebold et al., *Eur. J. Biochem.*, 176:617, 1988.
Strejan et al., *Prog Clin Biol Res.*, 146:429-34, 1984.
Sundaramoorthy et al., *J. Biol. Chem.*, 277:31142, 2002.
Than et al., *Biological Chemistry*, 386:759, 2005.
Than et al., *Proc. Natl. Acad. Sci. USA*, 99:6607, 2002.
Thorner et al., *J. Biol. Chem.*, 271:13821, 1996.
Tuqan et al., *Lasers Med. Sci.*, 20(2):80-6, 2005.
Van Leeuwen and Sangster, *Crit. Rev. Toxicol.*, 18:189, 1987
Vanacore et al., *J. Biol. Chem.*, 279:44723, 2004.
Vanacore et al., *J. Biol. Chem.*, 280:29300, 2005.
Vanacore et al., *J. Biol. Chem.*, 283:22737, 2008.
Vanacore et al., *Science*, 325:1230, 2009
Weber et al., *Eur. J. Biochem.*, 139:401, 1984.
Willker et al., *Magnetic Resonance in Chemistry*, 31:287, 1993.
Yates et al., *Anal. Chem.*, 67:1426, 1995.
Yurchenco and Furthmayr, *Biochemistry*, 23:1839, 1984.
Vanacore et al., *Science* 325, 1230-1234 (2009).
Fessler, L. I. & Fessler, J. H., *J. Biol. Chem.* 257, 9804-9810 (1982).
Nelson et al., *EMBO J.* 13, 3438-3447 (1994).
Alexander, N. M., *J. Biol. Chem.* 234, 1530-1533 (1959).
Weiss et al., *J. Clin. Invest.* 70, 598-607 (1982).
Tang et al., *J. Biol. Chem.* 258, 4331-4338 (1983).
Candi et al., *J. Biol. Chem.* 270, 26382-26390 (1995).
Obinger, C., *Arch. Biochem. Biophys.* 445, 197-198 (2006).
Dypbukt et al., *Free Radic. Biol. Med.* 39, 1468-1477 (2005).
Morin et al., *Proc. Natl. Acad. Sci. USA* 98, 15050-15055 (2001).
Gotenstein et al., *Development* 137, 3603-3613 (2010).
Gupta et al., *J. Cell Biol.* 137, 1185-1196 (1997).
Cheng et al., *Free Radic. Biol. Med.* 45, 1682-1694 (2008).
Coupry et al., *Arch. Ophthalmol.* 128, 483-489 (2010).
Favor et al., *Genetics* 175, 725-736 (2007).
Gould, D. B., Marchant, J. K., Savinova, O. V., Smith, R. S. & John, S. W. Col4a1 mutation causes endoplasmic reticulum stress and genetically modifiable ocular dysgenesis. Hum. Mol. Genet. 16, 798-807 (2007).
Labelle-Dumais, et al., *PLoS Genet.* 7, e1002062 (2011).
Van Agtmael et al., *Hum. Mol. Genet.* 14, 3161-3168 (2005).
Péterfi et al., *Am. J. Pathol.* 175, 725-735 (2009).
Beal et al., *Biochemistry* 48, 11142-11148 (2009).
Peskin et al., *Biochemistry* 48, 10175-10182 (2009).
Armesto et al., *Tetrahedron* 56, 1103-1109 (2000).
Lavine, T. F., *J. Biol. Chem.* 169, 477-491 (1947).
Huwiler et al., *Eur. J. Biochem.* 147, 469-476 (1985).
Blair-Johnson et al., *Biochemistry* 40, 13990-13997 (2001).
Andrews, P. C. & Krinsky, N. I., *J. Biol. Chem.* 257, 13240-13245 (1982).
Taurog, A. & Dorris, M. L., *Arch. Biochem. Biophys.* 296, 239-246 (1992).
Garver et al., *Dev. Comp. Immunol.* 32, 519-531 (2008).
Zamocky et al., *Proteins* 72, 589-605 (2008).
Brownlee, M., *Nature* 414, 813-820 (2001).
Touyz, R. M. & Briones, A. M., *Hypertens. Res.* 34, 5-14 (2011).
Yokoyama, M., *Curr. Opin. Pharmacol.* 4, 110-115 (2004).
Bai et al., *Free Radic. Biol. Med.* 51, 1492-1500 (2011).
Shi et al., *Cardiovasc. Res.* 91, 27-36 (2011).
Brandes, R. P. *Cardiovasc. Res.* 91, 1-2 (2011).
Lau, D. & Baldus, S., *Pharmacol. Ther.* 111, 16-26 (2006).
Kirk, in Biochemistry of the Elemental Halogens and Inorganic Halides. (Springer, 1991), pp. 109-120.
Weiss et al., *Science* 234, 200 (1986).
Denzler et al., *J. Immunol.* 167, 1672 (2001).
Li et al., *Infection and Immunity* 80, 2528 (2012).
Bhave et al., *Nature Chemical Biology* 8, 784 (2012).
Vanacore et al., *Science* 325, 1230 (2009).
Gotenstein et al., *Development* 137, 3603 (2010).
Langeveld et al., *J. Biological Chemistry* 263, 10481 (1988).
Aaij and Borst, *Biochimica et Biophysica Acta (BBA)—Nucleic Acids and Protein Synthesis* 269, 192 (1972).
Joy et al., *Analytical Chemistry* 45, 856 (1973).
Peskin et al., *Biochemistry* 48, 10175 (2009).
Pattison and Davies, *Biochemistry* 43, 4799 (2004).
Liang et al., *BMC Biochemistry* 13, 21 (2012).
Illuminati and Mandolini, *Accounts Chemical Research* 14, 95 (1981).
Ciuffarin and Guaraldi, *J. Organic Chemistry* 35, 2006 (1970).
Chmutova et al., *RUSSIAN JOURNAL OF ORGANIC CHEMISTRY C/C OF ZHURNAL ORGANICHESKOI KHIMII* 35, 56 (1999).
Klopman, *J. American Chemical Society* 90, 223 (1968).
Pearson, *J. Chemical Education* 45, 643 (11968).
Piedade-Guerreiro et al., *J. Radioanalytical and Nuclear Chemistry*, Articles 110, 531 (1987).
Fairbanks and Burch, *Annals Entomological Society America* 63, 1628 (1970).
Pavelka et al., *Physiological Research/Academia Scientiarum Bohemoslovaca* 54, 639 (2005).
Haigo and Bilder, *Science* 331, 1071 (2011).
Bilder and Haigo, *Developmental Cell* 22, 12 (2012).
Frieden, *J. Chemical Education* 62, 917 (1985).

Mertz, The essential trace elements. *Science* 213, 1332 (1981).
Frieden, *Trends Biochemical Sciences* 6, 50 (1981).
Uauy et al., *American J. Clinical Nutrition* 67, 952S (1998).
Olszowy et al., *J. Analytical Toxicology* 22, 225 (May 1, 1998, 1998).
van Leeuwen et al., *CRC Critical Reviews in Toxicology* 18, 189 (1987).
Barratt and Walser, *J. Clinical Investigation* 48, 56 (1969).
Wolf and Eadie, *American J. Physiology* 163, 436 (1950).
Walser and Rahill, *Clinical Science* 30, 191 (1966).
Trautner and Wieth, *Acta Physiologica Scandinavica* 74, 606 (1968).
Canavese et al., *American J. Kidney Diseases* 48, 1018 (2006).
Carney, FIVE CASES OF BROMISM. *The Lancet* 298, 523 (1971).
Fidler et al., *Proc. Natl. Acad. Sci. USA* 111, 331-336, 2014
Pavelka et al., *Physiol. Res.* 54, 639-644, 2005.
Shanbhag and Tripathi, *J. Exp. Biol.* 212, 1731-1744, 2009.
Haigo and Bilder, *Science* 331, 1071-1074, 2011.
Mertz, *Science* 213, 1332-1338, 1981.
Barratt and Walser, *J. Clin. Invest.* 48, 56-66, 1969.
Brodie et al., *J. Biol. Chem.* 130, 555-563, 1939.
Woods et al., *Bull. Environ. Contam. Toxicol.* 23, 179-185, 1979.
Piedade-Guerreiro et al., *J. Radioanal. Nucl. Chem.* 110, 531-537, 1987.
van Logten et al., *Toxicology* 2, 257-267, 1974.
Olszowy et al., *J. Anal. Toxicol.* 22, 225-230, 1998.
van Leeuwen and Sangster, *Crit. Rev. Toxicol.* 18, 189-213, 1987.
Trautner and Wieth, *Acta Physiol. Scand.* 74, 606-615, 1968.
Walser and Rahill, *Clin. Sci.* 30, 191-205, 1966.
Wolf and Eadie, *Am. J. Physiol.* 163, 436-441, 1950.
Anke et al., *Acta Agronomica Hung.* 39, 297-303, 1990.
Dahlstrom et al., *J. Pediatr.* 109, 625-630, 1986.
Miura et al., *Nucl. Instrum. Meth.* B 189, 443-449, 2002.
Oe et al., In Trace Element Metabolism in Man and Animals (Canberra, Australia: TEMA-4 Australian Academy of Science), pp. 526-529, 1981.
Wallaeys et al., *Kidney Int.* 30, 599-604, 1986.
Nielsen, *J. Trace Elem. Exp. Med.* 11, 251-274, 1998.
Groos et al., *J. Surg. Res.* 109, 74-85, 2003.
Tsuge et al., *J. Health Sci.* 46, 343-350, 2000.
Asmussen, *Clin. Cardiol.* 2, 246-256, 1979.
Soltani et al., *Histopathology* 60, 964-970, 2012.

What is claimed is:

1. A method for promoting tissue stability in a target tissue site in a subject suffering from removal or injury of collagen from said target tissue site comprising:
 (a) identifying a subject in need of tissue stabilization; and
 (b) administering to said subject a bromide salt,
 wherein the target concentration of bromide at said target tissue site is between 30 µM and 100 µM following treatment.

2. The method of claim 1, wherein said subject is a non-human animal.

3. The method of claim 1, wherein said subject is a human.

4. The method of claim 1, wherein said bromide salt is administered as a sole active ingredient.

5. The method of claim 1, wherein said bromide salt is administered in combination with a second active agent.

6. The method of claim 5, wherein said second active agent is peroxide, molecular oxygen, or an electron-accepting compound.

7. The method of claim 1, wherein said subject suffers from removal or injury of collagen containing tissues.

8. The method of claim 7, wherein removal or injury involves a medical operation, a trauma, or a disease.

9. The method of claim 8, where the disease is periodontal disease or cataracts.

10. The method of claim 5, wherein said second active agent is an antimicrobial agent.

11. The method of claim 10, wherein the antimicrobial agent is a hypohalous acid or hypohalite compound.

12. The method of claim 1, further comprising reducing the amount of chloride or thiocyanate levels in the blood or at said target tissue site in said subject.

13. The method of claim 1, wherein administering comprises oral, intravenous, intra-arterial, subcutaneous, transdermal or topical administration.

14. The method of claim 1, wherein administering comprises systemic administration or administration to or local/regional to a site of healing.

15. The method of claim 6, wherein the electron accepting compound is selected from the group consisting of flavin adenine dinucleotide (FAD), hypobromous acid, nicotinamide adenine dinucelotide (NAD & NADH), nicotinamide adenine dinucelotide phosphate (NADP & NADPH), inosine monophosphate (IMP), guanosine monophosphate (GMP) and combinations thereof.

16. The method of claim 1, wherein the target concentration of bromide at said target tissue site is 30 µM, 50 µM, 75 µM, or 100 µM.

* * * * *

UNITED STATES PATENT AND TRADEMARK OFFICE
CERTIFICATE OF CORRECTION

PATENT NO. : 10,183,039 B2  
APPLICATION NO. : 14/905457  
DATED : January 22, 2019  
INVENTOR(S) : Billy G. Hudson et al.

Page 1 of 1

It is certified that error appears in the above-identified patent and that said Letters Patent is hereby corrected as shown below:

In the Specification

In Column 1, Lines 10-13, please delete the paragraph and insert:
--This invention was made with government support under grant numbers DK018381, and DK065123, awarded by the National Institutes of Health. The government has certain rights in the invention.--
therefor.

Signed and Sealed this  
Twenty-sixth Day of September, 2023

Katherine Kelly Vidal  
*Director of the United States Patent and Trademark Office*